(12) United States Patent
Gray et al.

(10) Patent No.: US 10,081,639 B2
(45) Date of Patent: Sep. 25, 2018

(54) PYRIMIDO-DIAZEPINONE KINASE SCAFFOLD COMPOUNDS AND METHODS OF TREATING DISORDERS

(71) Applicant: Dana-Farber Cancer Institute, Inc., Boston, MA (US)

(72) Inventors: Nathanael S. Gray, Boston, MA (US); Xianming Deng, Jamaica Plain, MA (US); Nicholas Paul Kwiatkowski, Auburn, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 0 days.

(21) Appl. No.: 15/605,515

(22) Filed: May 25, 2017

(65) Prior Publication Data

US 2017/0260208 A1    Sep. 14, 2017

Related U.S. Application Data

(63) Continuation of application No. 15/231,209, filed on Aug. 8, 2016, now Pat. No. 9,701,683, which is a continuation of application No. 14/994,213, filed on Jan. 13, 2016, now Pat. No. 9,464,091, which is a continuation of application No. 13/143,505, filed as application No. PCT/US2010/000050 on Jan. 6, 2010, now Pat. No. 9,266,890.

(60) Provisional application No. 61/193,901, filed on Jan. 6, 2009.

(51) Int. Cl.
| | |
|---|---|
| *C07D 487/04* | (2006.01) |
| *C07D 487/12* | (2006.01) |
| *C07D 471/14* | (2006.01) |
| *C07D 487/14* | (2006.01) |
| *C07D 491/14* | (2006.01) |
| *C07D 498/04* | (2006.01) |
| *C07D 513/04* | (2006.01) |
| *C07D 495/14* | (2006.01) |

(52) U.S. Cl.
CPC ......... *C07D 513/04* (2013.01); *C07D 471/14* (2013.01); *C07D 487/04* (2013.01); *C07D 487/14* (2013.01); *C07D 495/14* (2013.01); *C07D 498/04* (2013.01)

(58) Field of Classification Search
CPC .. C07D 487/04; C07D 487/12; C07D 471/14; C07D 487/14; C07D 491/14; C07D 495/14; C07D 498/04; C07D 513/04
See application file for complete search history.

(56) References Cited

U.S. PATENT DOCUMENTS

2008/0234255 A1    9/2008    Chen

FOREIGN PATENT DOCUMENTS

| WO | WO-2007095188 A2 | 8/2007 |
| WO | WO-2008003958 A2 | 1/2008 |
| WO | WO-2008113711    | 9/2008 |
| WO | WO-2009067547 A1 | 5/2009 |

OTHER PUBLICATIONS

Notification of Reasons for Refusal (Office Action) dated Feb. 25, 2014, in corresponding Japanese Application No. 2011-544638.

*Primary Examiner* — Bruck Kifle
(74) *Attorney, Agent, or Firm* — Burns & Levinson, LLP; Daniel W. Clarke

(57) ABSTRACT

The present invention relates to novel pyrimido-diazepinone compounds, methods of modulating protein kinases, including MPS1 (TTK), ERK5 (BMK1, MAPK7), polo kinase 1, 2, 3, or 4, Ack1, Ack2, Abl, DCAMKL1, ABL1, Abl mutants, DCAMKL2, ARK5, BRK, MKNK2, FGFR4, TNK1, PLK1, ULK2, PLK4, PRKD1, PRKD2, PRKD3, ROS1, RPS6KA6, TAOK1, TAOK3, TNK2, Bcr-Abl, GAK, cSrc, TPR-Met, Tie2, MET, FGFR3, Aurora, Axl, Bmx, BTK, c-kit, CHK2, Flt3, MST2, p70S6K, PDGFR, PKB, PKC, Raf, ROCK-II, Rsk1, SGK, TrkA, TrkB and TrkC, and the use of such compounds in the treatment of various diseases, disorders or conditions.

6 Claims, 8 Drawing Sheets

DNA Tubulin Phospho H3

| Compound ID | Structure | IC$_{50}$ (nM) on Mps1 Kinase Activity |
|---|---|---|
| I-1 | 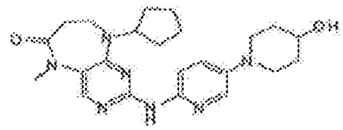 | 890.8 |
| I-6 | 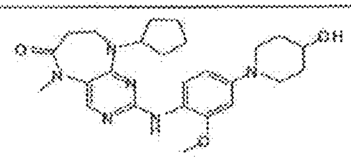 | 342.2 |
| I-9 | 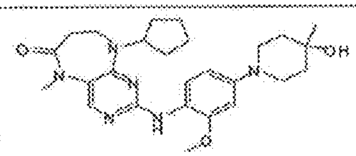 | 254.3 |
| I-10 | 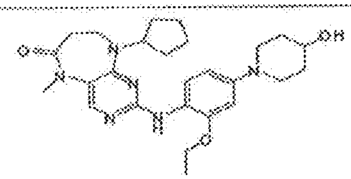 | 144.5 |
| I-11 | 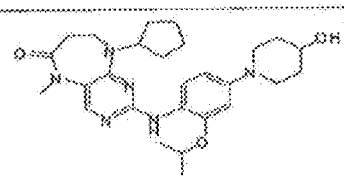 | 604.7 |
| I-13 | 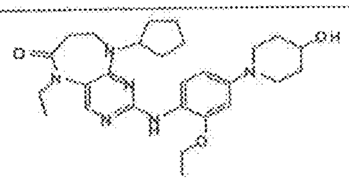 | 1006 |

| Compound ID | Structure | $K_D$ (nM) on Plk1 |
|---|---|---|
| I-1 | 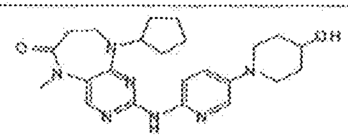 | 49 |
| I-3 | 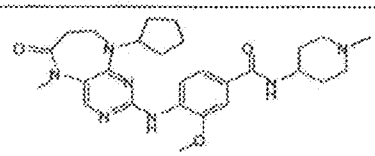 | 0.57 |
| I-6 | 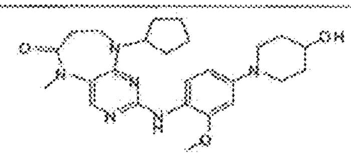 | 19 |
| I-7 | 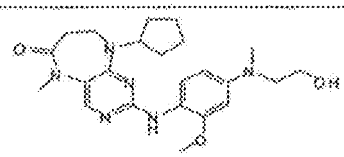 | 36 |
| I-8 | 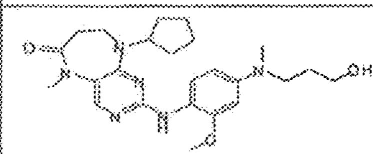 | 35 |
| I-10 | 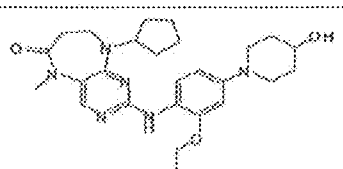 | 47 |

| Compound ID | Structure | Kd of Erk5 (nM) |
|---|---|---|
| I-20 | 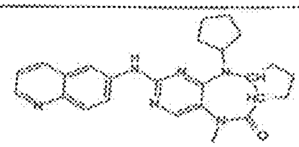 | 550 |
| I-24 | 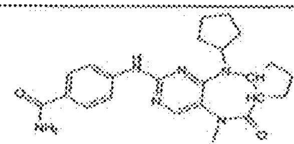 | 320 |
| IV-2 | 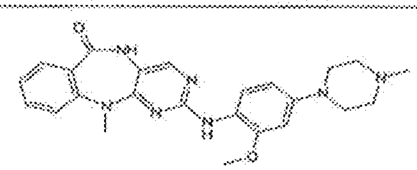 | 670 |
| IV-1 | 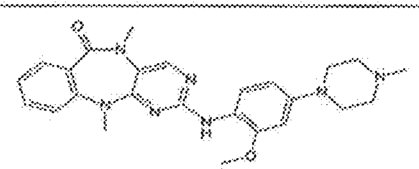 | 19 |
| IV-7 | 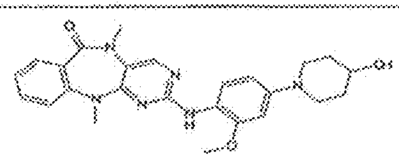 | 57 |
| IV-6 | 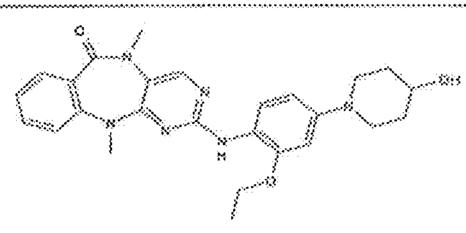 | 80 |
| IV-8 | 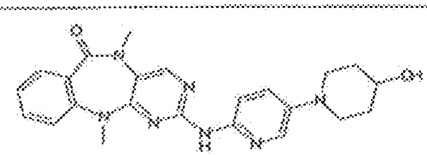 | 50 |

PYRIMIDO-DIAZEPINONE KINASE SCAFFOLD COMPOUNDS AND METHODS OF TREATING DISORDERS

CROSS REFERENCE TO RELATED APPLICATIONS

This application is a continuation of U.S. application Ser. No. 15/231,209, filed on Aug. 8, 2016, which is a continuation of U.S. application Ser. No. 14/994,213, filed on Jan. 13, 2016 (now U.S. Pat. No. 9,464,091, issued on Oct. 11, 2016), which is a continuation of U.S. application Ser. No. 13/143,505, filed on Nov. 1, 2011, (now U.S. Pat. No. 9,266,890, issued on Feb. 23, 2016), which is a 35 U.S.C. § 371 U.S. national stage entry of International Application PCT/US2010/000050 (WO 2010/080712) having an International filing date of Jan. 6, 2010, which claims the benefit of U.S. Provisional Application No. 61/193,901, filed on Jan. 6, 2009. The entire contents of each of the above applications are incorporated herein by reference.

TECHNICAL FIELD

The present invention relates to novel pyrimido-diazepinone compounds which are able to modulate protein kinases, including MPS1 (TTK), ERK5 (BMK1, MAPK7), polo kinase 1, 2, 3, or 4, Ack1, Ack2, Abl, DCAMKL1, ABL1, Abl mutants, DCAMKL2, ARK5, BRK, MKNK2, FGFR4, TNK1, PLK1, ULK2, PLK4, PRKD1, PRKD2, PRKD3, ROS1, RPS6KA6, TAOK1, TAOK3, TNK2, Bcr-Abl, GAK, cSrc, TPR-Met, Tie2, MET, FGFR3, Aurora, Axl, Bmx, BTK, c-kit, CHK2, Flt3, MST2, p70S6K, PDGFR, PKB, PKC, Raf, ROCK-H, Rsk1, SGK, TrkA, TrkB and TrkC, and the use of such compounds in the treatment of various diseases, disorders or conditions.

BACKGROUND OF THE INVENTION

Protein kinases represent a large family of proteins, which play a central role in the regulation of a wide variety of cellular processes and maintaining control over cellular function. Protein kinases constitute a large family of structurally related enzymes that are responsible for the control of a variety of signal transduction processes within the cell (see Hardie, G and Hanks, S. The Protein Kinase Facts Book, I and II, Academic Press, San Diego, Calif.: 1995). Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids etc).

In general, protein kinases mediate intracellular signaling by catalyzing a phosphoryl transfer from a nucleoside triphosphate to a protein acceptor that is involved in a signaling pathway. These phosphorylation events act as molecular on/off switches that can modulate or regulate the target protein biological function.

These phosphorylation events are ultimately triggered in response to a variety of extracellular and other stimuli. Examples of such stimuli include environmental and chemical stress signals (e.g., shock, heat shock, ultraviolet radiation, bacterial endotoxin, and H2O2), cytokines (e.g., interleukin-1 (IL-I) and tumor necrosis factor alpha (TNF-a), and growth factors (e.g., granulocyte macrophage-colony stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, survival and regulation of the cell cycle.

A partial, non-limiting, list of these kinases include: receptor tyrosine kinases such as platelet-derived growth factor receptor kinase (PDGF-R), the nerve growth factor receptor, Trk-A, -B and -C, and the fibroblast growth factor receptor, FGFR3; non-receptor tyrosine kinases such Abl and the fusion kinase BCR-Abl, Lck, Csk, Fes, BTK, Bmx and c-src; and serine/threonine kinases such as Aurora, c-RAF, SGK, MAP kinases (e.g., MKK4, MKK6, etc.) and SAPK2α and SAPK2β. Aberrant kinase activity has been observed in many disease states including benign and malignant proliferative disorders as well as diseases resulting from inappropriate activation of the immune and nervous systems.

The novel compounds of this invention inhibit the activity of one or more protein kinases and are, therefore, expected to be useful in the treatment of kinase-associated diseases.

SUMMARY OF THE INVENTION

In one aspect, the invention provides a compound of formula A:

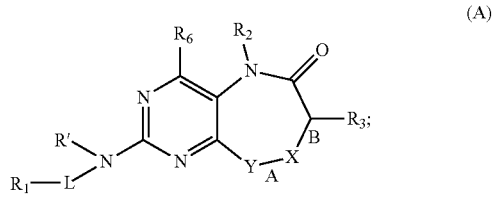

(A)

or a pharmaceutically acceptable salt, ester or prodrug thereof,
wherein,
X is $CHR_4$, $CR_4$, NH, $NR_4$ or N;
Y is $NR_5$, N, S, SO, $SO_2$, O, $CHR_5$, or $CR_5$; wherein at least one of X and Y is NH, $NR_4$, $NR_5$, N, S, SO, $SO_2$, or O;
A is a single bond or double bond;
B is a single bond or double bond, wherein both A and B are not double bonds;
R' is H or alkyl;
L is absent, S, SO, $SO_2$, or CO;
$R_1$ is H, alkyl, alkenyl, alkynyl, each containing 0, 1, 2, or 3 heteroatoms selected from O, S, or N; or $R_1$ is aryl, arylalkyl, heteroaryl, heterocyclic, or carbocyclic; wherein $R_1$ may be optionally substituted;
$R_2$ is hydrogen or optionally substituted alkyl;
$R_3$ is hydrogen, alkyl, alkenyl, aryl, arylalkyl, heteroaryl, heterocyclic, or carbocyclic, each of which may be optionally substituted;
$R_4$ is hydrogen, alkyl, alkenyl, aryl, arylalkyl, heteroaryl, heterocyclic, or carbocyclic, each of which may be optionally substituted;
$R_5$ is hydrogen, alkyl, alkenyl, aryl, arylalkyl, heteroaryl, heterocyclic, or carbocyclic, each of which may be optionally substituted;
or $R_3$ and X, together with the atoms to which they are attached, form a 3-8 membered carbocyclic, aryl, heterocyclic, or heteroaryl; each of which is optionally substituted;

or X and Y, together with the atoms to which they are attached, form a 3-8 membered carbocyclic, aryl, heterocyclic, or heteroaryl; each of which is optionally substituted; and $R_6$ is hydrogen or optionally substituted alkyl.

In another aspect, the invention provides a method of treating a disease in a subject comprising administering to the subject a compound, pharmaceutically acceptable salt, ester or prodrug of formula A.

In another aspect, the invention provides a method of treating a kinase mediated disorder in a subject comprising: administering to the subject identified as in need thereof a compound, pharmaceutically acceptable salt, ester or prodrug of formula A.

In another aspect, the invention provides a method for reducing kinase-dependent cell growth comprising contacting a cell with a kinase inhibitor compound of formula A.

In other aspects, the invention provides a method of inhibiting kinase in a subject identified as in need of such treatment, comprising administering a compound of formula A.

In another aspect, the invention provides a kit comprising a compound capable of inhibiting kinase activity selected from one or more compounds of claim 1, and instructions for use in treating cancer.

In another aspect, the invention provides a pharmaceutical composition comprising a compound of formula A, or a pharmaceutically acceptable ester, salt, or prodrug thereof, together with a pharmaceutically acceptable carrier.

In one aspect, the invention provides a method of synthesizing a compound of formula A.

DETAILED DESCRIPTION OF THE INVENTION

Definitions

Figure 1:
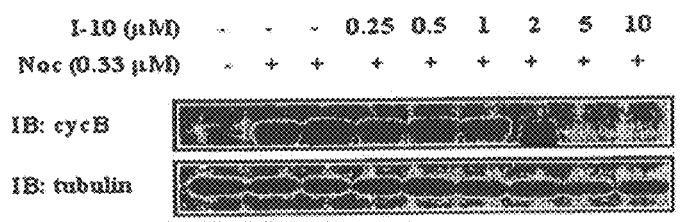
FIG. 1. Mps1 inhibitor I-10 induces escape from mitosis. Hela cells were arrested in mitosis using the following protocol. Cells were treated with thymidine (2.5 mM) for 24 hours. Cells were released into medium containing nocodazole (0.33 µM). After 16 hrs. cells were treated with I-10 a range of concentrations (0.25, 0.5, 1, 2, 5 and 10 uM) shown above for 2 hrs. Cells were harvested and the levels of cyclin B (a marker for mitosis) were determined by immunoblot. High cyclin B levels indicated mitotic cells, while low cyclin B levels indicate cells have exited nocodazole-induced mitotic arrest.

Listed below are definitions of various terms used to describe this invention. These definitions apply to the terms as they are used throughout this specification and claims, unless otherwise limited in specific instances, either individually or as part of a larger group.

The term "alkyl," as used herein, refers to saturated, straight- or branched-chain hydrocarbon radicals containing, in certain embodiments, between one and six, or one and eight carbon atoms, respectively. Examples of $C_1$-$C_6$ alkyl radicals include, but are not limited to, methyl, ethyl, propyl, isopropyl, n-butyl, tert-butyl, neopentyl, n-hexyl radicals; and examples of $C_1$-$C_8$ alkyl radicals include, but are not limited to, methyl, ethyl, propyl, isopropyl, n-butyl, tert-butyl, neopentyl, n-hexyl, heptyl, octyl radicals.

The term "alkenyl," as used herein, denotes a monovalent group derived from a hydrocarbon moiety containing, in certain embodiments, from two to six, or two to eight carbon atoms having at least one carbon-carbon double bond. The double bond may or may not be the point of attachment to another group. Alkenyl groups include, but are not limited to, for example, ethenyl, propenyl, butenyl, 1-methyl-2-buten-1-yl, heptenyl, octenyl and the like.

The term "alkynyl," as used herein, denotes a monovalent group derived from a hydrocarbon moiety containing, in certain embodiments, from two to six, or two to eight carbon atoms having at least one carbon-carbon triple bond. The alkynyl group may or may not be the point of attachment to another group. Representative alkynyl groups include, but are not limited to, for example, ethynyl, 1-propynyl, 1-butynyl, heptynyl, octynyl and the like.

The term "alkoxy" refers to an —O-alkyl radical.

The term "aryl," as used herein, refers to a mono- or poly-cyclic carbocyclic ring system having one or more aromatic rings, fused or non-fused, including, but not limited to, phenyl, naphthyl, tetrahydronaphthyl, indanyl, idenyl and the like.

The term "aralkyl," as used herein, refers to an alkyl residue attached to an aryl ring. Examples include, but are not limited to, benzyl, phenethyl and the like.

The term "cycloalkyl," as used herein, denotes a monovalent group derived from a monocyclic or polycyclic saturated or partially unsaturated carbocyclic ring compound. Examples of $C_3$-$C_8$-cycloalkyl include, but not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo [2.2.1] heptyl, and bicyclo [2.2.2] octyl. Also contemplated are a monovalent group derived from a monocyclic or polycyclic carbocyclic ring compound having at least one carbon-carbon double bond by the removal of a single hydrogen atom. Examples of such groups include, but are not limited to, cyclopropenyl, cyclobutenyl, cyclopentenyl, cyclohexenyl, cycloheptenyl, cyclooctenyl, and the like.

The term "heteroaryl," as used herein, refers to a mono- or poly-cyclic (e.g., bi-, or tri-cyclic or more) fused or non-fused, radical or ring system having at least one aromatic ring, having from five to ten ring atoms of which one ring atoms is selected from S, O and N; zero, one or two ring atoms are additional heteroatoms independently selected from S, O and N; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "heteroaralkyl," as used herein, refers to an alkyl residue attached to a heteroaryl ring. Examples include, but are not limited to, pyridinylmethyl, pyrimidinylethyl and the like.

The term "heterocycloalkyl," as used herein, refers to a non-aromatic 3-, 4-, 5-, 6- or 7-membered ring or a bi- or tri-cyclic group fused of non-fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, and (v) any of the above rings may be fused to a benzene ring. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "alkylamino" refers to a group having the structure —NH($C_1$-$C_{12}$ alkyl) where $C_1$-$C_{12}$ alkyl is as previously defined.

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates. Examples of aliphatic carbonyls include, but are not limited to, acetyl, propionyl, 2-fluoroacetyl, butyryl, 2-hydroxy acetyl, and the like.

In accordance with the invention, any of the aryls, substituted aryls, heteroaryls and substituted heteroaryls described herein, can be any aromatic group. Aromatic groups can be substituted or unsubstituted.

The terms "halo" and "halogen," as used herein, refer to an atom selected from fluorine, chlorine, bromine and iodine.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. The terms "optionally substituted", "optionally substituted alkyl," "optionally substituted "optionally substituted alkenyl," "optionally substituted alkynyl", "optionally substituted cycloalkyl," "optionally substituted cycloalkenyl," "optionally substituted aryl", "optionally substituted heteroaryl," "optionally substituted aralkyl", "optionally substituted heteroaralkyl," "optionally substituted heterocycloalkyl," and any other optionally substituted group as used herein, refer to groups that are substituted or unsubstituted by independent replacement of one, two, or three or more of the hydrogen atoms thereon with substituents including, but not limited to:

—F, —Cl, —Br, —I,

—OH, protected hydroxy,

—$NO_2$, —CN,

—$NH_2$, protected amino, —NH—$C_1$-$C_{12}$-alkyl, —NH—$C_2$-$C_{12}$-alkenyl, —NH—$C_2$-$C_{12}$-alkenyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkenyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkenyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_{12}$-alkenyl, —CONH—$C_2$-$C_{12}$-alkenyl, —CONH—$C_3$-$C_{12}$-cycloalkyl, —CONH-aryl, —CONH-heteroaryl, —CONH-heterocycloalkyl, —$OCO_2$—$C_1$-$C_{12}$-alkyl, —$OCO_2$—$C_2$-$C_{12}$-alkenyl, —$OCO_2$—$C_2$-$C_{12}$-alkenyl, —$OCO_2$—$C_3$-$C_{12}$-cycloalkyl, —$OCO_2$-aryl, —$OCO_2$-heteroaryl, —$OCO_2$-heterocycloalkyl, —$OCONH_2$, —OCONH—$C_1$-$C_{12}$-alkyl, —OCONH—$C_2$-$C_{12}$-alkenyl, —OCONH—$C_2$-$C_{12}$-alkenyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_{12}$-alkenyl, —NHC(O)—$C_2$-$C_{12}$-alkenyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_{12}$-alkenyl, —$NHCO_2$—$C_2$-$C_{12}$-alkenyl, —$NHCO_2$—$C_3$-$C_{12}$-cycloalkyl, —$NHCO_2$-aryl, —$NHCO_2$-heteroaryl, —$NHCO_2$-heterocycloalkyl, —$NHC(O)NH_2$, —NHC(O)NH—$C_1$-$C_{12}$-alkyl, —NHC(O)NH—$C_2$-$C_{12}$-alkenyl, —NHC(O)NH—$C_2$-$C_{12}$-alkenyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)$NH_2$, —NHC(S)NH—$C_1$-$C_{12}$-alkyl, —NHC(S)NH—$C_2$-$C_{12}$-alkenyl, —NHC(S)NH—$C_2$-$C_{12}$-alkenyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)$NH_2$, —NHC(NH)NH—$C_1$-$C_{12}$-alkyl, —NHC(NH)NH—$C_2$-$C_{12}$-alkenyl, —NHC(NH)NH—$C_2$-$C_{12}$-alkenyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_{12}$-alkenyl, —NHC(NH)—$C_2$-$C_{12}$-alkenyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_{12}$-alkenyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_{12}$-alkenyl, —S(O)—$C_2$-$C_{12}$-alkenyl, —S(O)—$C_3$-$C_{12}$-cycloalkyl, —S(O)-aryl, —S(O)-heteroaryl, —S(O)-heterocycloalkyl-$SO_2NH_2$, —$SO_2$NH—$C_1$-$C_{12}$-alkyl, —$SO_2$NH—$C_2$-$C_{12}$-alkenyl, —$SO_2$NH—$C_2$-$C_{12}$-alkenyl, —$SO_2$NH—$C_3$-$C_{12}$-cycloalkyl, —$SO_2$NH-aryl, —$SO_2$NH-heteroaryl, —$SO_2$NH-heterocycloalkyl, —NHSO$_2$—C$_1$-C$_{12}$-alkyl, —NHSO$_2$—C$_2$-C$_{12}$-alkenyl, —NHSO$_2$—C$_2$-C$_{12}$-alkenyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_{12}$-alkenyl, —S—C$_2$-C$_{12}$-alkenyl, —S—C$_3$-C$_{12}$-cycloalkyl, —S-aryl, —S-heteroaryl, —S-heterocycloalkyl, or methylthiomethyl.

It is understood that the aryls, heteroaryls, alkyls, and the like can be further substituted.

The term "cancer" includes, but is not limited to, the following cancers: epidermoid Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal; rectum, Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma] hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, undifferentiated thyroid cancer, multiple endocrine neoplasia type 2A, multiple endocrine neoplasia type 2B, familial medullary thyroid cancer, pheochromocytoma, paraganglioma; and Adrenal glands: neuroblastoma. Thus, the term "cancerous cell" as provided herein, includes a cell afflicted by any one of the above-identified conditions.

The term "Kinase Panel" is a list of kinases comprising MPS1 (TTK), ERK5 (BMK1, MAPK7), polo kinase 1, 2, 3, or 4, Ack1, Ack2, Abl, DCAMKL1, ABL1, Abl mutants, DCAMKL2, ARK5, BRK, MKNK2, FGFR4, TNK1, PLK1, ULK2, PLK4, PRKD1, PRKD2, PRKD3, ROS1, RPS6KA6, TAOK1, TAOK3, TNK2, Bcr-Abl, GAK, cSrc, TPR-Met, Tie2, MET, FGFR3, Aurora, Axl, Bmx, BTK, c-kit, CHK2, Flt3, MST2, p70S6K, PDGFR, PKB, PKC, Raf, ROCK-H, Rsk1, SGK, TrkA, TrkB, TrkC, AAK1, ABL1, ABL1(E255K), ABL1(F317I), ABL1(F317L), ABL1 (H396P), ABL1(M351T), ABL1(Q252H), ABL1(T315I), ABL1(Y253F), ABL2, ACVR1, ACVR1B, ACVR2A, ACVR2B, ACVRL1, ADCK3, ADCK4, AKT1, AKT2, AKT3, ALK, AMPK-alpha1, AMPK-alpha2, ANKK1, ARK5, ASK1, ASK2, AURKA, AURKB, AURKC, AXL, BIKE, BLK, BMPR1A, BMPR1B, BMPR2, BMX, BRAF, BRAF(V600E), BRK, BRSK1, BRSK2, BTK, CAMK1, CAMK1D, CAMK1G, CAMK2A, CAMK2D, CAMK2G, CAMK4, CAMKK1, CAMKK2, CDC2L1, CDC2L2, CDK11, CDK2, CDK3, CDK5, CDK7, CDK8, CDK9, CDKL2, CDKL3, CDKL5, CHECK1, CHEK2, CIT, CLK1, CLK2, CLK3, CLK4, CSF1R, CSK, CSNK1A1L, CSNK1D, CSNK1E, CSNK1G1, CSNK1G3, CSNK2A1, CSNK2A2, CTK, DAPK1, DAPK2, DAPK3, DCAMKL1, DCAMKL2, DCAMKL3, DDR1, DDR2, DLK, DMPK, DMPK2, DRAK1, DRAK2, DYRK1A, DYRK1B, DYRK2, EGFR, EGFR (E746-A750DEL), EGFR (G719C), EGFR (G719S), EGFR(L747-E749del, A750P), EGFR(L747-S752del, P753 S), EGFR(L747-T751del, Sins), EGFR (L858R), EGFR(L858R,T790M), EGFR(L861Q), EGFR (S752-I759del), EPHA1, EPHA2, EPHA3, EPHA4, EPHA5, EPHA6, EPHA7, EPHA8, EPHB1, EPHB2, EPHB3, EPHB4, EPHB6, ERBB2, ERBB3, ERBB4, ERK1, ERK2, ERK3, ERK4, ERK5, ERK8, ERN1, FAK, FER, FES, FGFR1, FGFR2, FGFR3, FGFR3(G697C), FGFR4, FGR, FLT1, FLT3, FLT3(D835H), FLT3(D835Y), FLT3 (ITD), FLT3(K663Q), FLT3(N841I), FLT4, FRK, FYN, GAK, GCN2(Kin.Dom.2,S808G), GRK1, GRK4, GRK7, GSK3A, GSK3B, HCK, HIPK1, HIPK2, HIPK3, HIPK4, HPK1, HUNK, ICK, IGF1R, IKK-ALPHA, IKK-BETA, IKK-EPSILON, INSR, INSRR, IRAK1, IRAK3, ITK, JAK1(JH1domain-catalytic), JAK1(JH2domain-pseudokinase), JAK2(JH1domain-catalytic), JAK3(JH1domain-catalytic), JNK1, JNK2, JNK3, KIT, KIT(D816V), KIT(L576P), KIT(V559D), KIT(V559D,T670I), KIT(V559D,V654A), LATS1, LATS2, LCK, LIMK1, LIMK2, LKB1, LOK, LTK, LYN, LZK, MAK, MAP3K1, MAP2K15, MAP3K2, MAP3K3, MAP3K4, MAP4K2, MAP4K3, MAP4K5, MAPKAPK2, MAPKAPK5, MARK1, MARK2, MARK3, MARK4, MAST1, MEK1, MEK2, MEK3, MEK4, MEK6, MELK, MERTK, MET, MET(M1250T), MET(Y1235D), MINK, MKNK1, MKNK2, MLCK, MLK1, MLK2, MLK3, MRCKA, MRCKB, MST1, MST1R, MST2, MST3, MST4, MUSK, MYLK, MYLK2, MYO3A, MYO3B, NDR1, NDR2, NEK1, NEK2, NEK5, NEK6, NEK7, NEK9, NIM1, NLK, OSR1, p38-alpha, p38-beta, p38-delta, p38-gamma, PAK1, PAK2, PAK3, PAK4, PAK6, PAK7, PCTK1, PCTK2, PCTK3, PDGFRA, PDGFRB, PDPK1, PFTAIRE2, PFTK1, PHKG1, PHKG2, PIK3C2B, PIK3C2G, PIK3CA, PIK3CA (C420R), PIK3CA(E542K), PIK3CA(E545A), PIK3CA (E545K), PIK3CA(H1047L), PIK3CA(H1047Y), PIK3CA (M1043I), PIK3CA(Q546K), PIK3CB, PIK3CD, PIK3CG, PIK4CB, PIM1, PIM2, PIM3, PIP5K1A, PIP5K2B, PKAC-ALPHA, PKAC-BETA, PKMYT1, PKN1, PKN2, PLK1, PLK2, PLK3, PLK4, PRKCD, PRKCE, PRKCH, PRKCQ, PRKD1, PRKD3, PRKG1, PRKG2, PRKR, PRKX, PRP4, PYK2, QSK, RAF1, RET, RET(M918T), RET(V804L), RET(V804M), RIOK1, RIOK2, RIOK3, RIPK1, RIPK2, RIPK4, ROCK1, ROCK2, ROS1, RPS6KA1(Kin.Dom.1-N-terminal), RPS6KA1(Kin.Dom.2-C-terminal), RPS6KA2 (Kin.Dom. 1-N-terminal), RPS6KA2(Kin.Dom.2-C-terminal), RPS6KA3(Kin.Dom.1-N-terminal), RPS6KA4 (Kin.Dom.1-N-terminal), RPS6KA4(Kin.Dom.2-C-terminal), RPS6KA5(Kin.Dom.1-N-terminal), RPS6KA5 (Kin.Dom.2-C-terminal), RPS6KA6(Kin.Dom. 1-N-terminal), RPS6KA6(Kin.Dom.2-C-terminal), SBK1, SgK085, SgK110, SIK, SIK2, SLK, SNARK, SRC, SRMS, SRPK1, SRPK2, SRPK3, STK16, STK33, STK39, SYK, TAK1, TAO1, TAOK2, TAOK3, TBK1, TEC, TESK1, TGFBR1, TGFBR2, TIE1, TIE2, TLK1, TLK2, TNIK, TNK1, TNK2, TNNI3K, TRKA, TRKB, TRKC, TSSK1B, TTK, TXK, TYK2(JH1domain-catalytic), TYK2 (JH2domain-pseudokinase), TYRO3, ULK1, ULK2, ULK3, VEGFR2, WEE1, WEE2, YANK2, YANK3, YES, YSK1, YSK4, ZAK and ZAP70. Compounds of the invention are screened against the kinase panel (wild type and/or mutation thereof) and inhibit the activity of at least one of said panel members.

Mutant forms of a kinase means single or multiple amino acid changes from the wild-type sequence.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

Treat", "treating" and "treatment" refer to a method of alleviating or abating a disease and/or its attendant symptoms.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to afford any compound delineated by the formulae of the instant invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38(1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

This invention also encompasses pharmaceutical compositions containing, and methods of treating disorders through administering, pharmaceutically acceptable prodrugs of compounds of the invention. For example, compounds of the invention having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes 4-hydroxyproline, hydroxyysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxy carbonyls, as outlined in Advanced Drug Delivery Reviews, 1996, 19, 1 15. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

Compounds of the Invention

In one aspect, the invention provides a compound of formula A:

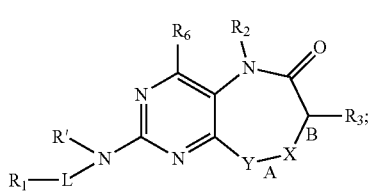

(A)

or a pharmaceutically acceptable salt, ester or prodrug thereof,
wherein,
X is $CHR_4$, $CR_4$, NH, $NR_4$ or N;
Y is $NR_5$, N, S, SO, $SO_2$, O, $CHR_5$, or $CR_5$; wherein at least one of X and Y is NH, $NR_4$, $NR_5$, N, S, SO, $SO_2$, or O;
A is a single bond or double bond;
B is a single bond or double bond, wherein both A and B are not double bonds;
R' is H or alkyl;
L is absent, S, SO, $SO_2$, or CO;
$R_1$ is H, alkyl, alkenyl, alkynyl, each containing 0, 1, 2, or 3 heteroatoms selected from O, S, or N; or $R_1$ is aryl, arylalkyl, heteroaryl, heterocyclic, or carbocyclic; wherein $R_1$ may be optionally substituted;

$R_2$ is hydrogen or optionally substituted alkyl;
$R_3$ is hydrogen, alkyl, alkenyl, aryl, arylalkyl, heteroaryl, heterocyclic, or carbocyclic, each of which may be optionally substituted;
$R_4$ is hydrogen, alkyl, alkenyl, aryl, arylalkyl, heteroaryl, heterocyclic, or carbocyclic, each of which may be optionally substituted;
$R_5$ is hydrogen, alkyl, alkenyl, aryl, arylalkyl, heteroaryl, heterocyclic, or carbocyclic, each of which may be optionally substituted;
or $R_3$ and X, together with the atoms to which they are attached, form a 3-8 membered carbocyclic, aryl, heterocyclic, or heteroaryl; each of which is optionally substituted;
or X and Y, together with the atoms to which they are attached, form a 3-8 membered carbocyclic, aryl, heterocyclic, or heteroaryl; each of which is optionally substituted; and
$R_6$ is hydrogen or optionally substituted alkyl.

In certain embodiments, the invention provides a compound wherein X is $CR_4$ or $CHR_4$, and Y is $NR_5$.

In other embodiments, the invention provides a compound wherein $R_4$ is hydrogen, alkyl, aryl, heteroaryl, heterocyclic, or carbocyclic, each of which may be optionally substituted; and $R_5$ is hydrogen, alkyl, aryl, heteroaryl, heterocyclic, or carbocyclic, each of which may be optionally substituted.

In certain embodiments, the invention provides a compound wherein X and Y, together with the atoms to which they are attached, form a 3-8 membered cycloalkyl, aryl, heterocycloalkyl, or heteroaryl; each of which is optionally substituted.

In other embodiments, the invention provides a compound wherein $R_3$ and X, together with the atoms to which they are attached, form a 3-8 membered cycloalkyl, aryl, heterocycloalkyl, or heteroaryl; each of which is optionally substituted.

In some embodiments, the invention provides a compound wherein X is N and Y is $CR_5$.

In a further embodiment, $R_5$ is alkyl, aryl, heteroaryl, heterocyclic, or carbocyclic, each of which may be optionally substituted.

In a first embodiment, the invention provides a compound of B:

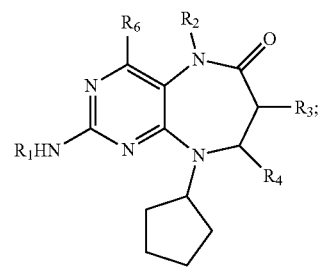

(B)

or a pharmaceutically acceptable salt, ester or prodrug thereof,
wherein,
$R_1$ is aryl, or heteroaryl, wherein $R_1$ may be optionally substituted;
$R_2$ is hydrogen or optionally substituted alkyl;
$R_3$ is hydrogen or methyl;
$R_4$ is hydrogen or methyl; and
$R_6$ is hydrogen.

In one embodiment, $R_1$ is phenyl or pyridyl, each of which may be optionally substituted.

In a further embodiment, $R_1$ is substituted with 0-4 substituents, selected from $N(R_A)(R_A)$, $C(O)NH(R_A)$, alkoxy, and heterocyclic, each of which may be further substituted; wherein each $R_A$ is independently selected from alkyl, and heterocyclic.

In another further embodiment, $R_1$ is substituted with 0-4 substituents, selected from alkoxy,

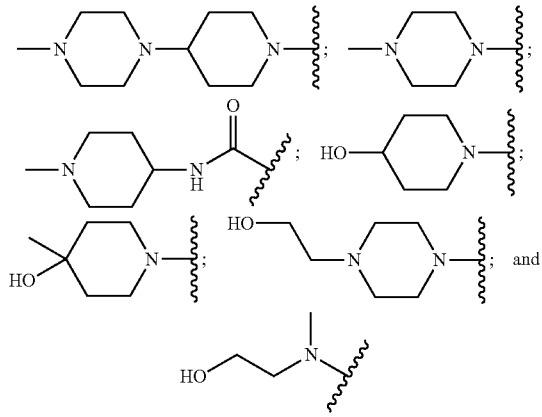

In a second embodiment, the invention provides a compound of formula C:

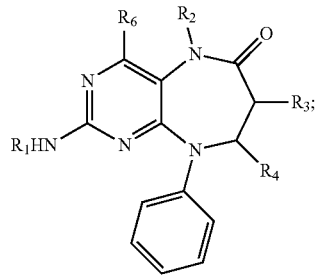
(C)

or a pharmaceutically acceptable salt, ester or prodrug thereof,
wherein,
$R_1$ is aryl, heteroaryl, which may be optionally substituted;
$R_2$ is hydrogen or methyl;
$R_3$ is hydrogen;
$R_4$ is hydrogen; and
$R_6$ is hydrogen.

In certain embodiments, $R_1$ is phenyl or pyridyl, each of which may be optionally substituted.

In a further embodiment, $R_1$ is substituted with 0-4 substituents, selected from alkoxy, or heterocyclic, which may be further substituted.

In certain embodiments, $R_1$ is substituted with 0-4 substituents, selected from alkoxy,

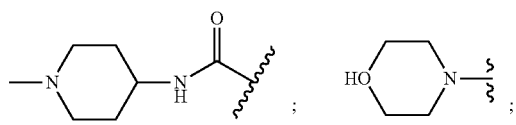

-continued

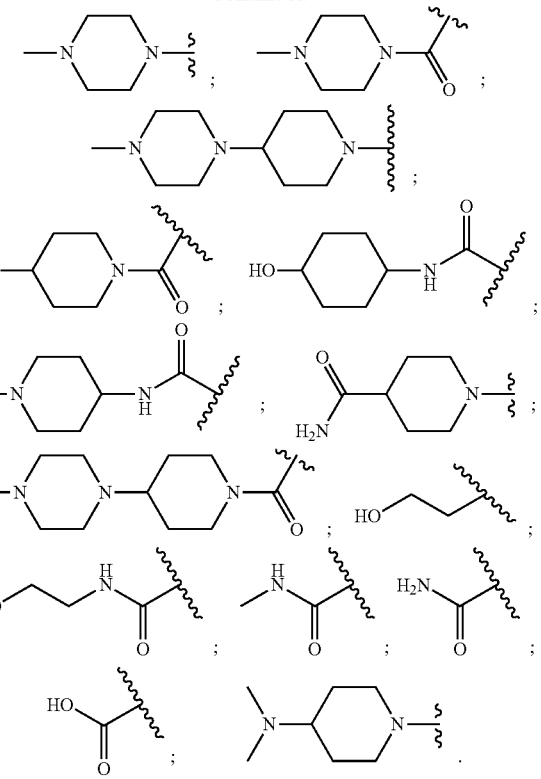

In a third embodiment, the invention provides a compound of formula D:

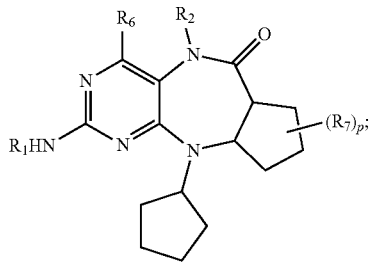
(D)

or a pharmaceutically acceptable salt, ester or prodrug thereof,
wherein,
$R_1$ is alkyl, aryl, heteroaryl, heterocyclic, or carbocyclic, wherein $R_1$ may be optionally substituted;
$R_2$ is hydrogen or optionally substituted alkyl;
$R_6$ is hydrogen or optionally substituted alkyl;
each $R_7$ is independently alkyl, alkenyl, aryl, arylalkyl, heteroaryl, heterocyclic, carbocyclic, alkoxy, NH(alkyl), NH(aryl), N(alkyl)(alkyl), or N(alkyl)(aryl), each of which may be optionally substituted; hal, nitro, or cyano; and
p is 0-6.

In one embodiment, $R_1$ is methyl, ethyl, propyl, isopropyl, butyl, s-butyl, t-butyl, pentyl, hexyl, cyclohexyl, piperidinyl, pyrrolidino, phenyl, 1-naphthyl, 2-naphthyl, pyridyl, pyrimidinyl, pyrazinyl, pyridizinyl, quinolinyl, thienyl, thiazolyl, oxazolyl, isoxazolyl, pyrrolyl, furanyl, isoquinolinyl, imiazolyl, or triazolyl, each of which may be optionally substituted.

In a further embodiment, $R_1$ is alkyl, phenyl, cyclohexyl, piperidinyl, quinolinyl, or pyridyl, each of which may be optionally substituted.

In certain embodiments, $R_1$ is substituted with 0-4 substituents, selected from hal, nitro, cyano, hydroxyl, amino, $NH(R_A)$, $N(R_A)(R_A)$, $CO_2H$, $C(O)R_A$, $C(O)OR_A$, $C(O)NH_2$, $C(O)NH(R_A)$, $C(O)N(R_A)(R_A)$, alkyl, aryl, arylalkyl, alkoxy, heteroaryl, heterocyclic, and carbocyclic, each of which may be further substituted; wherein each $R_A$ is independently selected from alkyl, carbocyclic, aryl, heteroaryl, and heterocyclic.

In certain embodiments, $R_1$ is substituted with 0-4 substituents, selected from alkyl, alkoxy, hydroxyl,

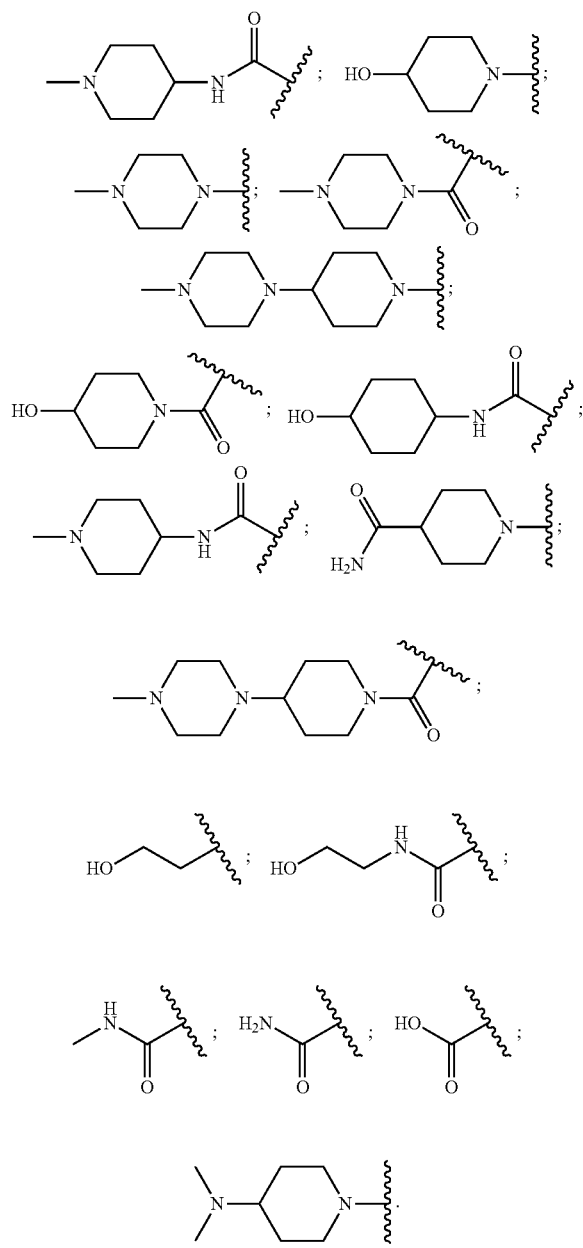

In a fourth embodiment, the invention provides a compound of formula E:

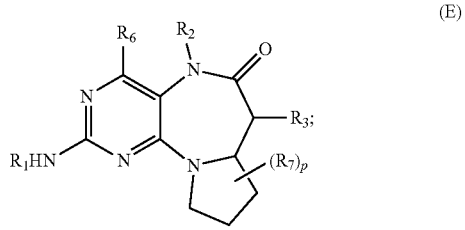

or a pharmaceutically acceptable salt, ester or prodrug thereof, wherein, $R_1$ is alkyl, aryl, heteroaryl, heterocyclic, or carbocyclic, wherein $R_1$ may be optionally substituted;

$R_2$ is hydrogen or optionally substituted alkyl;

$R_3$ is hydrogen or optionally substituted alkyl;

$R_6$ is hydrogen or optionally substituted alkyl;

each $R_7$ is independently alkyl, alkenyl, aryl, arylalkyl, heteroaryl, heterocyclic, carbocyclic, alkoxy, NH(alkyl), NH(aryl), N(alkyl)(alkyl), or N(alkyl)(aryl), each of which may be optionally substituted; hal, nitro, or cyano; and p is 0-6.

In certain embodiments, $R_1$ is methyl, ethyl, propyl, iso-propyl, butyl, s-butyl, t-butyl, pentyl, hexyl, cyclohexyl, piperidinyl, pyrrolidino, phenyl, 1-naphthyl, 2-naphthyl, pyridyl, pyrimidinyl, pyrazinyl, pyridizinyl, quinolinyl, thienyl, thiazolyl, oxazolyl, isoxazolyl, pyrrolyl, furanyl, isoquinolinyl, imiazolyl, or triazolyl, each of which may be optionally substituted.

In a further embodiment, $R_1$ is phenyl or pyridyl, each of which may be optionally substituted.

In another further embodiment, $R_1$ is substituted with 0-4 substituents, selected from hal, nitro, cyano, hydroxyl, amino, $NH(R_A)$, $N(R_A)(R_A)$, $CO_2H$, $C(O)R_A$, $C(O)OR_A$, $C(O)NH_2$, $C(O)NH(R_A)$, $C(O)N(R_A)(R_A)$, alkyl, aryl, arylalkyl, alkoxy, heteroaryl, heterocyclic, and carbocyclic, each of which may be further substituted; wherein each $R_A$ is independently selected from alkyl, carbocyclic, aryl, heteroaryl, and heterocyclic.

In certain embodiments, $R_1$ is substituted with 0-4 substituents, selected from alkoxy,

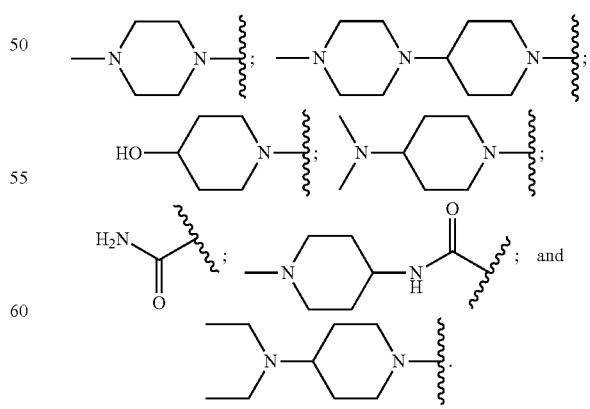

In a fifth embodiment, the invention provides a compound of formula F:

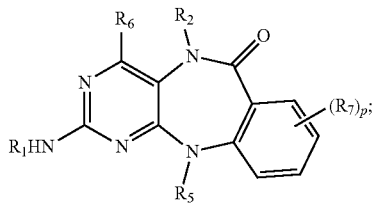

(F)

or a pharmaceutically acceptable salt, ester or prodrug thereof, wherein, $R_1$ is alkyl, aryl, heteroaryl, heterocyclic, or carbocyclic, wherein $R_1$ may be optionally substituted;

$R_2$ is hydrogen or optionally substituted alkyl;

$R_5$ is hydrogen, optionally substituted alkyl, optionally substituted aralkyl, or optionally substituted carbocyclic; and $R_6$ is hydrogen or optionally substituted alkyl;

each $R_7$ is independently alkyl, alkenyl, aryl, arylalkyl, heteroaryl, heterocyclic, carbocyclic, alkoxy, NH(alkyl), NH(aryl), N(alkyl)(alkyl), or N(alkyl)(aryl), each of which may be optionally substituted; hal, nitro, or cyano; and p is 0-4.

In certain embodiments, $R_1$ is methyl, ethyl, propyl, iso-propyl, butyl, s-butyl, t-butyl, pentyl, hexyl, cyclohexyl, piperidinyl, pyrrolidino, phenyl, 1-naphthyl, 2-naphthyl, pyridyl, pyrimidinyl, pyrazinyl, pyridizinyl, quinolinyl, thienyl, thiazolyl, oxazolyl, isoxazolyl, pyrrolyl, furanyl, isoquinolinyl, imiazolyl, or triazolyl, each of which may be optionally substituted.

In a further embodiment, $R_1$ is phenyl or pyridyl, each of which may be optionally substituted.

In another embodiment, $R_1$ is substituted with 0-4 substituents, selected from hal, nitro, cyano, hydroxyl, amino, NH($R_A$), N($R_A$)($R_A$), $CO_2H$, C(O)$R_A$, C(O)O$R_A$, C(O)$NH_2$, C(O)NH($R_A$), C(O)N($R_A$)($R_A$), alkyl, aryl, arylalkyl, alkoxy, heteroaryl, heterocyclic, and carbocyclic, each of which may be further substituted; wherein each $R_A$ is independently selected from alkyl, carbocyclic, aryl, heteroaryl, and heterocyclic.

In certain embodiments, $R_1$ is substituted with 0-4 substituents, selected from alkoxy, $CO_2Me$,

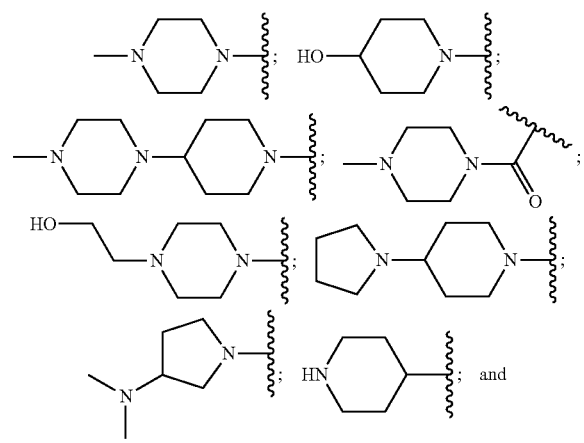

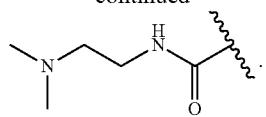

In a sixth embodiment, the invention provides a compound of formula F-I:

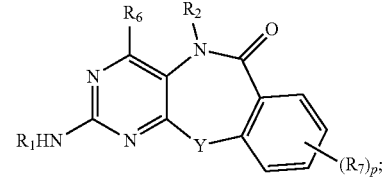

(F-I)

or a pharmaceutically acceptable salt, ester or prodrug thereof, wherein,

Y is S, SO, $SO_2$, or O;

$R_1$ is alkyl, aryl, heteroaryl, heterocyclic, or carbocyclic, wherein $R_1$ may be optionally substituted;

$R_2$ is hydrogen or optionally substituted alkyl;

$R_6$ is hydrogen or optionally substituted alkyl;

each $R_7$ is independently alkyl, alkenyl, aryl, arylalkyl, heteroaryl, heterocyclic, carbocyclic, alkoxy, NH(alkyl), NH(aryl), N(alkyl)(alkyl), or N(alkyl)(aryl), each of which may be optionally substituted; hal, nitro, or cyano; and p is 0-4.

In one embodiment, $R_1$ is methyl, ethyl, propyl, isopropyl, butyl, s-butyl, t-butyl, pentyl, hexyl, cyclohexyl, piperidinyl, pyrrolidino, phenyl, 1-naphthyl, 2-naphthyl, pyridyl, pyrimidinyl, pyrazinyl, pyridizinyl, quinolinyl, thienyl, thiazolyl, oxazolyl, isoxazolyl, pyrrolyl, furanyl, isoquinolinyl, imiazolyl, or triazolyl, each of which may be optionally substituted.

In a further embodiment, $R_1$ is phenyl or pyridyl, each of which may be optionally substituted.

In another embodiment, $R_1$ is substituted with 0-4 substituents, selected from hal, nitro, cyano, hydroxyl, amino, NH($R_A$), N($R_A$)($R_A$), $CO_2H$, C(O)$R_A$, C(O)O$R_A$, C(O)$NH_2$, C(O)NH($R_A$), C(O)N($R_A$)($R_A$), alkyl, aryl, arylalkyl, alkoxy, heteroaryl, heterocyclic, and carbocyclic, each of which may be further substituted;

wherein each $R_A$ is independently selected from alkyl, carbocyclic, aryl, heteroaryl, and heterocyclic.

In a further embodiment, $R_1$ is substituted with 0-4 substituents, selected from alkoxy, $CO_2Me$,

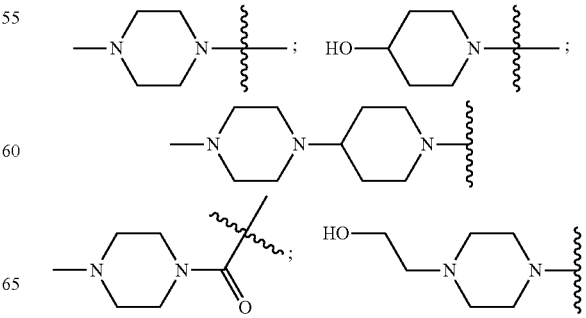

-continued

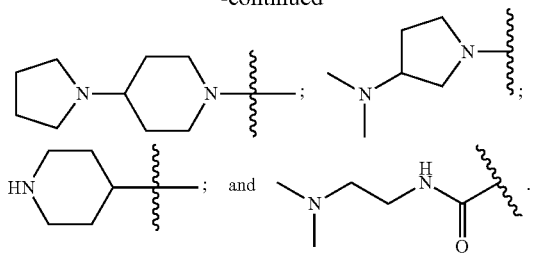

In a seventh embodiment, the invention provides a compound of formula G:

(G)

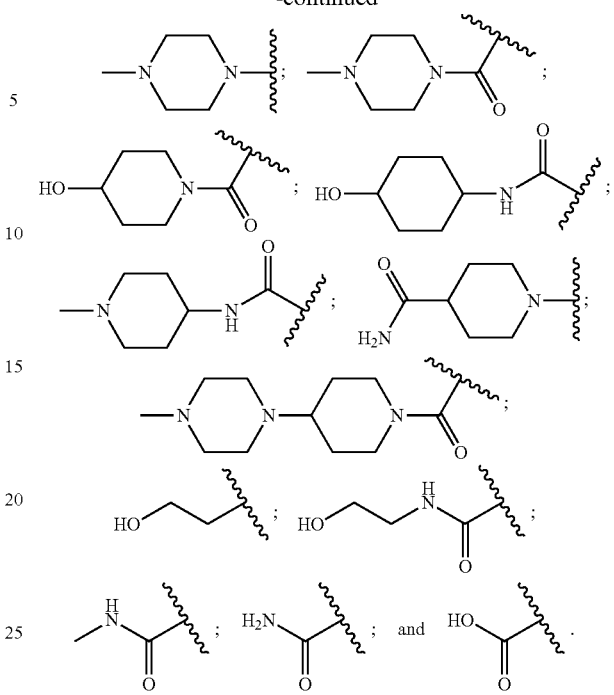

or a pharmaceutically acceptable salt, ester or prodrug thereof,
wherein, $R_1$ is alkyl, alkenyl, alkynyl, each containing 0, 1, 2, or 3 heteroatoms selected from O, S, or N; or $R_1$ is aryl, arylalkyl, heteroaryl, heterocyclic, or carbocyclic, wherein $R_1$ may be optionally substituted;

$R_2$ is hydrogen or optionally substituted alkyl;

$R_3$ is hydrogen, alkyl, alkenyl, aryl, arylalkyl, heteroaryl, heterocyclic, or carbocyclic, each of which may be optionally substituted;

$R_5$ is hydrogen, alkyl, alkenyl, aryl, arylalkyl, heteroaryl, heterocyclic, or carbocyclic, each of which may be optionally substituted; and $R_6$ is hydrogen or optionally substituted alkyl.

In one embodiment, $R_1$ is methyl, ethyl, propyl, isopropyl, butyl, s-butyl, t-butyl, pentyl, hexyl, cyclohexyl, piperidinyl, pyrrolidino, phenyl, 1-naphthyl, 2-naphthyl, pyridyl, pyrimidinyl, pyrazinyl, pyridizinyl, quinolinyl, thienyl, thiazolyl, oxazolyl, isoxazolyl, pyrrolyl, furanyl, isoquinolinyl, imiazolyl, or triazolyl, each of which may be optionally substituted.

In a further embodiment, $R_1$ is optionally substituted phenyl.

In another embodiment, $R_1$ is substituted with 0-4 substituents, selected from hal, nitro, cyano, hydroxyl, amino, $NH(R_A)$, $N(R_A)(R_A)$, $CO_2H$, $C(O)R_A$, $C(O)NH_2$, $C(O)NH(R_A)$, $C(O)N(R_A)(R_A)$, alkyl, aryl, arylalkyl, alkoxy, heteroaryl, heterocyclic, and carbocyclic, each of which may be further substituted; wherein each $R_A$ is independently selected from alkyl, carbocyclic, aryl, heteroaryl, and heterocyclic.

In certain embodiments, $R_1$ is substituted with 0-4 substituents, selected from alkoxy, hydroxyl,

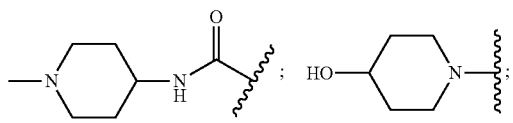

In another embodiment, $R_5$ is optionally substituted phenyl or optionally substituted cyclopentyl.

Representative compounds of the invention include, but are not limited to, the following compounds of Tables 1-5, which follow the examples.

The synthesis of the compounds of the invention can be found in the Examples below.

Another embodiment is a method of making a compound of any of the formulae herein using any one, or combination of, reactions delineated herein. The method can include the use of one or more intermediates or chemical reagents delineated herein.

Another aspect is an isotopically labeled compound of any of the formulae delineated herein. Such compounds have one or more isotope atoms which may or may not be radioactive (e.g., $^3H$, $^2H$, $^{14}C$, $^{13}C$, $^{35}S$, $^{32}P$, $^{125}I$, and $^{131}I$) introduced into the compound. Such compounds are useful for drug metabolism studies and diagnostics, as well as therapeutic applications.

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base.

Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", 3rd edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

In addition, some of the compounds of this invention have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms, and other stereoisomeric forms that may be defined, in terms of absolute stereochemistry, as (R)- or (S)-, or as (D)- or (L)- for amino acids. All such isomeric forms of these compounds are expressly included in the present invention. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). The compounds of this invention may also be represented in multiple tautomeric forms, in such instances, the invention expressly includes all tautomeric forms of the compounds described herein (e.g., alkylation of a ring system may result in alkylation at multiple sites, the invention expressly includes all such reaction products). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion. All such isomeric forms of such compounds are expressly included in the present invention. All crystal forms of the compounds described herein are expressly included in the present invention.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present invention. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds of this invention may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The compounds of the invention are defined herein by their chemical structures and/or chemical names. Where a compound is referred to by both a chemical structure and a chemical name, and the chemical structure and chemical name conflict, the chemical structure is determinative of the compound's identity.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

Methods of the Invention

In another aspect, the invention provides a method of treating a disease in a subject comprising administering to the subject a compound, pharmaceutically acceptable salt, ester or prodrug of formula A.

In one embodiment, the invention provides a method wherein the disease is mediated by a kinase selected from a MAP kinase, a mitotic spindle kinase, and a polo kinase.

In another embodiment, the invention provides a method wherein the disease is mediated by a kinase selected from MPS1, ERK5, BMK1, MAPK7, polo kinase 1, 2, 3, or 4, Ack1, Ack2, Abl, DCAMKL1, ABL1, Abl mutants, DCAMKL2, ARK5, BRK, MKNK2, FGFR4, TNK1, PLK1, ULK2, PLK4, PRKD1, PRKD2, PRKD3, ROS1, RPS6KA6, TAOK1, TAOK3, TNK2, Bcr-Abl, GAK, cSrc, TPR-Met, Tie2, MET, FGFR3, Aurora, Axl, Bmx, BTK, c-kit, CHK2, Flt3, MST2, p70S6K, PDGFR, PKB, PKC, Raf, ROCK-H, Rsk1, SGK, TrkA, TrkB and TrkC. In a further embodiment, the kinase is ERK-5, MPS1, or BMK-1.

In another embodiment, the invention provides a method wherein the disease is cancer or a proliferation disease.

In a further embodiment, the disease is lung, colon, breast, prostate, liver, pancreas, brain, kidney, ovaries, stomach, skin, and bone cancers, gastric, breast, pancreatic cancer, glioma, and hepatocellular carcinoma, papillary renal carcinoma, head and neck squamous cell carcinoma, leukemias, lymphomas, myelomas, and solid tumors.

In another embodiment, the disease is inflammation, arthritis, rheumatoid arthritis, spondylarthropathies, gouty arthritis, osteoarthritis, juvenile arthritis, and other arthritic conditions, systemic lupus erthematosus (SLE), skin-related conditions, psoriasis, eczema, burns, dermatitis, neuroinflammation, allergy, pain, neuropathic pain, fever, pulmonary disorders, lung inflammation, adult respiratory distress syndrome, pulmonary sarcoisosis, asthma, silicosis, chronic pulmonary inflammatory disease, and chronic obstructive pulmonary disease (COPD), cardiovascular disease, arteriosclerosis, myocardial infarction (including post-myocardial infarction indications), thrombosis, congestive heart failure, cardiac reperfusion injury, as well as complications associated with hypertension and/or heart failure such as vascular organ damage, restenosis, cardiomyopathy, stroke including ischemic and hemorrhagic stroke, reperfusion injury, renal reperfusion injury, ischemia including stroke and brain ischemia, and ischemia resulting from cardiac/coronary bypass, neurodegenerative disorders, liver disease and nephritis, gastrointestinal conditions, inflammatory bowel disease, Crohn's disease, gastritis, irritable bowel syndrome, ulcerative colitis, ulcerative diseases, gastric ulcers, viral and bacterial infections, sepsis, septic shock, gram negative sepsis, malaria, meningitis, HIV infection, opportunistic infections, cachexia secondary to infection or malignancy, cachexia secondary to acquired immune deficiency syndrome (AIDS), AIDS, ARC (AIDS related complex), pneumonia, herpes virus, myalgias due to infection, influenza, autoimmune disease, graft vs. host reaction and allograft rejections, treatment of bone resorption diseases, osteoporosis, multiple sclerosis, cancer, leukemia, lymphoma, colorectal cancer, brain cancer, bone cancer, epithelial call-derived neoplasia (epithelial carcinoma), basal cell carcinoma, adenocarcinoma, gastrointestinal cancer, lip cancer, mouth cancer, esophageal cancer, small bowel cancer, stomach cancer, colon cancer, liver cancer, bladder cancer, pancreas cancer, ovarian cancer, cervical cancer, lung cancer, breast cancer, skin cancer, squamus cell and/or basal cell cancers, prostate cancer, renal cell carcinoma, and other known cancers that affect epithelial cells throughout the body, chronic myelogenous leukemia (CML), acute myeloid leukemia (AML) and acute promyelocytic leukemia (APL), angiogenesis including neoplasia, metastasis, central nervous system disorders, central nervous system disorders having an inflammatory or apoptotic component, Alzheimer's disease, Parkinson's disease, Huntington's disease, amyotrophic lateral sclerosis, spinal cord injury, and peripheral neuropathy, Canine B-Cell Lymphoma.

In a further embodiment, the disease is inflammation, arthritis, rheumatoid arthritis, spondylarthropathies, gouty arthritis, osteoarthritis, juvenile arthritis, and other arthritic conditions, systemic lupus erthematosus (SLE), skin-related conditions, psoriasis, eczema, dermatitis, pain, pulmonary disorders, lung inflammation, adult respiratory distress syndrome, pulmonary sarcoisosis, asthma, chronic pulmonary inflammatory disease, and chronic obstructive pulmonary disease (COPD), cardiovascular disease, arteriosclerosis, myocardial infarction (including post-myocardial infarction indications), congestive heart failure, cardiac reperfusion injury, inflammatory bowel disease, Crohn's disease, gastritis, irritable bowel syndrome, leukemia, lymphoma.

In another aspect, the invention provides a method of treating a kinase mediated disorder in a subject comprising: administering to the subject identified as in need thereof a compound, pharmaceutically acceptable salt, ester or prodrug of formula A.

In one embodiment, the compound is an inhibitor of MPS1, ERK5, BMK1, MAPK7, polo kinase 1, 2, 3, or 4, Ack1, Ack2, Abl, DCAMKL1, ABL1, Abl mutants, DCAMKL2, ARK5, BRK, MKNK2, FGFR4, TNK1, PLK1, ULK2, PLK4, PRKD1, PRKD2, PRKD3, ROS1, RPS6KA6, TAOK1, TAOK3, TNK2, Bcr-Abl, GAK, cSrc, TPR-Met, Tie2, MET, FGFR3, Aurora, Axl, Bmx, BTK, c-kit, CHK2, Flt3, MST2, p70S6K, PDGFR, PKB, PKC, Raf, ROCK-H, Rsk1, SGK, TrkA, TrkB or TrkC. In a further embodiment, the compound is an inhibitor of ERK-5, MPS1, or BMK-1.

In certain embodiments, the subject is administered an additional therapeutic agent.

In a further embodiment, the compound and the additional therapeutic agent are administered simultaneously or sequentially.

In another aspect, the invention provides a method for reducing kinase-dependent cell growth comprising contacting a cell with a kinase inhibitor compound of formula A.

In other aspects, the invention provides a method of inhibiting kinase in a subject identified as in need of such treatment, comprising administering a compound of formula A.

In certain embodiments, the invention provides a method wherein the subject is a human.

In other embodiments, the invention provides a method wherein the kinase inhibitor has a Ki for inhibiting kinase less than about 1 micromolar.

In one embodiment, the invention provides a method of synthesizing a compound of formula A.

Another aspect of this invention provides compounds or compositions that are inhibitors of protein kinases, and thus are useful for the treatment of the diseases, disorders, and conditions, along with other uses described herein. In certain embodiments, these compositions optionally further comprise one or more additional therapeutic agents.

The present invention provides compounds and compositions that are useful as inhibitors of protein kinases. In certain embodiments, the invention provides compounds and compositions that are useful as inhibitors of protein kinases selected from AAK1, ABL1, ABL1(E255K), ABL1 (F317I), ABL1(F317L), ABL1(H396P), ABL1(M351T), ABL1(Q252H), ABL1(T315I), ABL1(Y253F), ABL2, ACVR1, ACVR1B, ACVR2A, ACVR2B, ACVRL1, ADCK3, ADCK4, AKT1, AKT2, AKT3, ALK, AMPK-alpha1, AMPK-alpha2, ANKK1, ARK5, ASK1, ASK2, AURKA, AURKB, AURKC, AXL, BIKE, BLK, BMPR1A, BMPR1B, BMPR2, BMX, BRAF, BRAF(V600E), BRK, BRSK1, BRSK2, BTK, CAMK1, CAMK1D, CAMK1G, CAMK2A, CAMK2D, CAMK2G, CAMK4, CAMKK1, CAMKK2, CDC2L1, CDC2L2, CDK11, CDK2, CDK3, CDK5, CDK7, CDK8, CDK9, CDKL2, CDKL3, CDKL5, CHECK1, CHEK2, CIT, CLK1, CLK2, CLK3, CLK4, CSF1R, CSK, CSNK1A1L, CSNK1D, CSNK1E, CSNK1G1, CSNK1G3, CSNK2A1, CSNK2A2, CTK, DAPK1, DAPK2, DAPK3, DCAMKL1, DCAMKL2, DCAMKL3, DDR1, DDR2, DLK, DMPK, DMPK2, DRAK1, DRAK2, DYRK1A, DYRK1B, DYRK2, EGFR, EGFR (E746-A750DEL), EGFR (G719C), EGFR (G719S), EGFR(L747-E749del, A750P), EGFR(L747-S752del, P753 S), EGFR(L747-T751del, Sins), EGFR(L858R), EGFR (L858R,T790M), EGFR(L861Q), EGFR(S752-I759del), EPHA1, EPHA2, EPHA3, EPHA4, EPHA5, EPHA6, EPHA7, EPHA8, EPHB1, EPHB2, EPHB3, EPHB4, EPHB6, ERBB2, ERBB3, ERBB4, ERK1, ERK2, ERK3, ERK4, ERK5, ERK8, ERN1, FAK, FER, FES, FGFR1, FGFR2, FGFR3, FGFR3(G697C), FGFR4, FGR, FLT1, FLT3, FLT3(D835H), FLT3(D835Y), FLT3(ITD), FLT3 (K663Q), FLT3(N841I), FLT4, FRK, FYN, GAK, GCN2 (Kin.Dom.2,S808G), GRK1, GRK4, GRK7, GSK3A, GSK3B, HCK, HIPK1, HIPK2, HIPK3, HIPK4, HPK1, HUNK, ICK, IGF1R, IKK-ALPHA, IKK-BETA, IKK-EPSILON, INSR, INSRR, IRAK1, IRAK3, ITK, JAK1 (JH1domain-catalytic), JAK1(JH2domain-pseudokinase), JAK2(JH1domain-catalytic), JAK3(JH1domain-catalytic), JNK1, JNK2, JNK3, KIT, KIT(D816V), KIT(L576P), KIT (V559D), KIT(V559D,T670I), KIT(V559D,V654A), LATS1, LATS2, LCK, LIMK1, LIMK2, LKB1, LOK, LTK, LYN, LZK, MAK, MAP3K1, MAP2K15, MAP3K2, MAP3K3, MAP3K4, MAP4K2, MAP4K3, MAP4K5, MAPKAPK2, MAPKAPK5, MARK1, MARK2, MARK3, MARK4, MAST1, MEK1, MEK2, MEK3, MEK4, MEK6, MELK, MERTK, MET, MET(M1250T), MET(Y1235D), MINK, MKNK1, MKNK2, MLCK, MLK1, MLK2, MLK3, MRCKA, MRCKB, MST1, MST1R, MST2, MST3, MST4, MUSK, MYLK, MYLK2, MYO3A, MYO3B, NDR1, NDR2, NEK1, NEK2, NEK5, NEK6, NEK7, NEK9, NIM1, NLK, OSR1, p38-alpha, p38-beta, p38-delta, p38-gamma, PAK1, PAK2, PAK3, PAK4, PAK6, PAK7, PCTK1, PCTK2, PCTK3, PDGFRA, PDGFRB, PDPK1, PFTAIRE2, PFTK1, PHKG1, PHKG2, PIK3C2B, PIK3C2G, PIK3CA, PIK3CA (C420R), PIK3CA(E542K), PIK3CA(E545A), PIK3CA (E545K), PIK3CA(H1047L), PIK3CA(H1047Y), PIK3CA (M1043I), PIK3CA(Q546K), PIK3CB, PIK3CD, PIK3CG, PIK4CB, PIM1, PIM2, PIM3, PIP5K1A, PIP5K2B, PKAC-ALPHA, PKAC-BETA, PKMYT1, PKN1, PKN2, PLK1, PLK2, PLK3, PLK4, PRKCD, PRKCE, PRKCH, PRKCQ, PRKD1, PRKG1, PRKG2, PRKR, PRKX, PRP4, PYK2, QSK, RAF1, RET, RET(M918T), RET(V804L), RET(V804M), RIOK1, RIOK2, RIOK3, RIPK1, RIPK2, RIPK4, ROCK1, ROCK2, ROS1, RPS6KA1(Kin.Dom.1-N-terminal), RPS6KA1(Kin.Dom.2-C-terminal), RPS6KA2 (Kin.Dom. 1-N-terminal), RPS6KA2(Kin.Dom.2-C-terminal), RPS6KA3(Kin.Dom.1-N-terminal), RPS6KA4 (Kin.Dom.1-N-terminal), RPS6KA4(Kin.Dom.2-C-terminal), RPS6KA5(Kin.Dom.1-N-terminal), RPS6KA5 (Kin.Dom.2-C-terminal), RPS6KA6(Kin.Dom. 1-N-terminal), RPS6KA6(Kin.Dom.2-C-terminal), SBK1, SgK085, SgK110, SIK, SIK2, SLK, SNARK, SRC, SRMS, SRPK1, SRPK2, SRPK3, STK16, STK33, STK39, SYK, TAK1, TAO1, TAOK2, TAOK3, TBK1, TEC, TESK1, TGFBR1, TGFBR2, TIE1, TIE2, TLK1, TLK2, TNIK, TNK1, TNK2, TNNI3K, TRKA, TRKB, TRKC, TSSK1B, TTK, TXK, TYK2(JH1domain-catalytic), TYK2 (JH2domain-pseudokinase), TYRO3, ULK1, ULK2, ULK3, VEGFR2, WEE1, WEE2, YANK2, YANK3, YES, YSK1, YSK4, ZAK and ZAP70.

In some embodiments, the present invention provides compounds and compositions that are useful as inhibitors of protein kinases selected from MPS1, ERK5, BMK1, MAPK7, polo kinase 1, 2, 3, or 4, Ack1, Ack2, Abl, DCAMKL1, ABL1, Abl mutants, DCAMKL2, ARK5, BRK, MKNK2, FGFR4, TNK1, PLK1, ULK2, PLK4, PRKD1, PRKD2, PRKD3, ROS1, RPS6KA6, TAOK1, TAOK3, TNK2, Bcr-Abl, GAK, cSrc, TPR-Met, Tie2, MET, FGFR3, Aurora, Axl, Bmx, BTK, c-kit, CHK2, Flt3, MST2, p70S6K, PDGFR, PKB, PKC, Raf, ROCK-H, Rsk1, SGK, TrkA, TrkB and TrkC.

As inhibitors of protein kinases, the compounds and compositions of this invention are particularly useful for treating or lessening the severity of a disease, condition, or disorder where a protein kinase is implicated in the disease, condition, or disorder. In one aspect, the present invention provides a method for treating or lessening the severity of a disease, condition, or disorder where a protein kinase is implicated in the disease state. In another aspect, the present invention provides a method for treating or lessening the severity of a kinase disease, condition, or disorder where inhibition of enzymatic activity is implicated in the treatment of the disease. In another aspect, this invention provides a method for treating or lessening the severity of a disease, condition, or disorder with compounds that inhibit enzymatic activity by binding to the protein kinase. Another aspect provides a method for treating or lessening the severity of a kinase disease, condition, or disorder by inhibiting enzymatic activity of the kinase with a protein kinase inhibitor.

In some embodiments, said method is used to treat or prevent a condition selected from autoimmune diseases, inflammatory diseases, proliferative and hyperproliferative diseases, immunologically-mediated diseases, bone diseases, metabolic diseases, neurological and neurodegenerative diseases, cardiovascular diseases, hormone related diseases, allergies, asthma, and Alzheimer's disease. In other embodiments, said condition is selected from a proliferative disorder and a neurodegenerative disorder.

One aspect of this invention provides compounds that are useful for the treatment of diseases, disorders, and conditions characterized by excessive or abonormal cell proliferation. Such diseases include, a proliferative or hyperproliferative disease, and a neurodegenerative disease. Examples of proliferative and hyperproliferative diseases include, without limitation, cancer. The term "cancer" includes, but is not limited to, the following cancers: breast; ovary; cervix; prostate; testis, genitourinary tract; esophagus; larynx, glioblastoma; neuroblastoma; stomach; skin, keratoacanthoma; lung, epidermoid carcinoma, large cell carcinoma, small cell carcinoma, lung adenocarcinoma; bone; colon; colorectal; adenoma; pancreas, adenocarcinoma; thyroid, follicular carcinoma, undifferentiated carcinoma, papillary carcinoma; seminoma; melanoma; sarcoma; bladder carcinoma; liver carcinoma and biliary passages; kidney carcinoma; myeloid disorders; lymphoid disorders, Hodgkin's, hairy cells; buccal cavity and pharynx (oral), lip, tongue, mouth, pharynx; small intestine; colon-rectum, large intestine, rectum, brain and central nervous system; chronic myeloid leukemia (CML), and leukemia. The term "cancer" includes, but is not limited to, the following cancers: myeloma, lymphoma, or a cancer selected from gastric, renal, or and the following cancers: head and neck, oropharangeal, non-small cell lung cancer (NSCLC), endometrial, hepatocarcinoma, Non-Hodgkins lymphoma, and pulmonary.

In some embodiments, the compounds of this invention are useful for treating cancer, such as colorectal, thyroid, breast, and lung cancer; and myeloproliferative disorders, such as polycythemia vera, thrombocythemia, myeloid metaplasia with myelofibrosis, chronic myelogenous leukemia, chronic myelomonocytic leukemia, hypereosinophilic syndrome, juvenile myelomonocytic leukemia, and systemic mast cell disease.

In some embodiments, the compounds of this invention are useful for treating hematopoietic disorders, in particular, acute-myelogenous leukemia (AMLi), chronic-myelogenous leukemia (CML), acute-prornyelocytic leukemia, and acute lymphocytic leukemia (ALL).

Examples of neurodegenerative diseases include, without limitation, Alzheimer's disease.

Another aspect of this invention provides a method for the treatment or lessening the severity of a disease selected from a proliferative or hyperproliferative disease, or a neurodegenerative disease, comprising administering an effective amount of a compound, or a pharmaceutically acceptable composition comprising a compound, to a subject in need thereof.

The present invention provides compounds, compositions and methods for the treatment of kinase related disease, particularly MPS1, ERK5, BMK1, MAPK7, polo kinase 1, 2, 3, or 4, Ack1, Ack2, Abl, DCAMKL1, ABL1, Abl mutants, DCAMKL2, ARK5, BRK, MKNK2, FGFR4, TNK1, PLK1, ULK2, PLK4, PRKD1, PRKD2, PRKD3, ROS1, RPS6KA6, TAOK1, TAOK3, TNK2, Bcr-Abl, GAK, cSrc, TPR-Met, Tie2, MET, FGFR3, Aurora, Axl, Bmx, BTK, c-kit, CHK2, Flt3, MST2, p70S6K, PDGFR, PKB, PKC, Raf, ROCK-H, Rsk1, SGK, TrkA, TrkB and TrkC kinase related diseases.

Compounds of the invention modulate the activity of kinases and, as such, are useful for treating diseases or disorders in which kinases, contribute to the pathology and/or symptomology of the disease. Examples of kinases that are inhibited by the compounds and compositions described herein and against which the methods described herein are useful include, but are not limited to, MPS1, ERK5, BMK1, MAPK7, polo kinase 1, 2, 3, or 4, Ack1, Ack2, Abl, DCAMKL1, ABL1, Abl mutants, DCAMKL2, ARK5, BRK, MKNK2, FGFR4, TNK1, PLK1, ULK2, PLK4, PRKD1, PRKD2, PRKD3, ROS1, RPS6KA6, TAOK1, TAOK3, TNK2, Bcr-Abl, GAK, cSrc, TPR-Met, Tie2, MET, FGFR3, Aurora, Axl, Bmx, BTK, c-kit, CHK2, Flt3, MST2, p70S6K, PDGFR, PKB, PKC, Raf, ROCK-H, Rsk1, SGK, TrkA, TrkB and TrkC kinases.

As inhibitors of protein kinases, the compounds and compositions of this invention are also useful in biological samples. One aspect of the invention relates to inhibiting protein kinase activity in a biological sample, which method comprises contacting said biological sample with a compound of the invention or a composition comprising said compound. The term "biological sample", as used herein, means an in vitro or an ex vivo sample, including, without limitation, cell cultures or extracts thereof; biopsied material obtained from a mammal or extracts thereof; and blood, saliva, urine, feces, semen, tears, or other body fluids or extracts thereof. Inhibition of protein kinase activity in a biological sample is useful for a variety of purposes that are known to one of skill in the art. Examples of such purposes include, but are not limited to, blood transfusion, organtransplantation, and biological specimen storage.

Another aspect of this invention relates to the study of protein kinases in biological and pathological phenomena; the study of intracellular signal transduction pathways mediated by such protein kinases; and the comparative evaluation of new protein kinase inhibitors. Examples of such uses include, but are not limited to, biological assays such as enzyme assays and cell-based assays.

The activity of the compounds as protein kinase inhibitors may be assayed in vitro, in vivo or in a cell line. In vitro assays include assays that determine inhibition of either the kinase activity or ATPase activity of the activated kinase. Alternate in vitro assays quantitate the ability of the inhibitor to bind to the protein kinase and may be measured either by radiolabelling the inhibitor prior to binding, isolating the inhibitor/kinase complex and determining the amount of radiolabel bound, or by running a competition experiment where new inhibitors are incubated with the kinase bound to known radioligands. Detailed conditions for assaying a compound utilized in this invention as an inhibitor of various kinases are set forth in the Examples below.

In accordance with the foregoing, the present invention further provides a method for preventing or treating any of the diseases or disorders described above in a subject in need of such treatment, which method comprises administering to said subject a therapeutically effective amount of a compound of the invention or a pharmaceutically acceptable salt thereof. For any of the above uses, the required dosage will vary depending on the mode of administration, the particular condition to be treated and the effect desired.

Pharmaceutical Compositions

In another aspect, the invention provides a pharmaceutical composition comprising a compound of formula A, or a pharmaceutically acceptable ester, salt, or prodrug thereof, together with a pharmaceutically acceptable carrier.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Compounds of the invention can be administered in therapeutically effective amounts in combination with one or more therapeutic agents (pharmaceutical combinations). For example, synergistic effects can occur with other immunomodulatory or anti-inflammatory substances, for example when used in combination with cyclosporin, rapamycin, or ascomycin, or immunosuppressant analogues thereof, for example cyclosporin A (CsA), cyclosporin G, FK-506, rapamycin, or comparable compounds, corticosteroids, cyclophosphamide, azathioprine, methotrexate, brequinar, leflunomide, mizoribine, mycophenolic acid, mycophenolate mofetil, 15-deoxyspergualin, immunosuppressant antibodies, especially monoclonal antibodies for leukocyte receptors, for example MHC, CD2, CD3, CD4, CD7, CD25, CD28, B7, CD45, CD58 or their ligands, or other immunomodulatory compounds, such as CTLA41g. Where the compounds of the invention are administered in conjunction with other therapies, dosages of the co-administered compounds will of course vary depending on the type of co-drug employed, on the specific drug employed, on the condition being treated and so forth.

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, disorders are treated or prevented in a subject, such as a human or other animal, by administering to the subject a therapeutically effective amount of a compound of the invention, in such amounts and for such time as is necessary to achieve the desired result. The term "therapeutically effective amount" of a compound of the invention, as used herein, means a sufficient amount of the compound so as to decrease the symptoms of a disorder in a subject. As is well understood in the medical arts a therapeutically effective amount of a compound of this invention will be at a reasonable benefit/risk ratio applicable to any medical treatment.

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

In certain embodiments, a therapeutic amount or dose of the compounds of the present invention may range from about 0.1 mg/Kg to about 500 mg/Kg, alternatively from about 1 to about 50 mg/Kg. In general, treatment regimens according to the present invention comprise administration to a patient in need of such treatment from about 10 mg to about 1000 mg of the compound(s) of this invention per day in single or multiple doses. Therapeutic amounts or doses will also vary depending on route of administration, as well as the possibility of co-usage with other agents.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present invention will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The invention also provides for a pharmaceutical combinations, e.g. a kit, comprising a) a first agent which is a compound of the invention as disclosed herein, in free form or in pharmaceutically acceptable salt form, and b) at least one co-agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of the invention and a co-agent, are both administered to a patient simultaneously in the form of a single entity or dosage. The term "non-fixed combination" means that the active ingredients, e.g. a compound of the invention and a co-agent, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active ingredients.

In certain embodiments, these compositions optionally further comprise one or more additional therapeutic agents. For example, chemotherapeutic agents or other antiproliferative agents may be combined with the compounds of this invention to treat proliferative diseases and cancer. Examples of known chemotherapeutic agents include, but are not limited to, Gleevec™, adriamycin, dexamethasone, vincristine, cyclophosphamide, fluorouracil, topotecan, taxol, interferons, and platinum derivatives.

Other examples of agents the compounds of this invention may also be combined with include, without limitation: treatments for Alzheimer's Disease such as Aricept18 and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-I RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and antiparkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, antileukemic agents, and growth factors; and agents for treating immunodeficiency disorders such as gamma globulin. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxy-propylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes, oils such as peanut oil, cottonseed oil; safflower oil; sesame oil; olive oil; corn oil and soybean oil; glycols; such a propylene glycol or polyethylene glycol; esters such as ethyl oleate and ethyl laurate, agar; buffering agents such as magnesium hydroxide and aluminum hydroxide; alginic acid; pyrogen-free water, isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The protein kinase inhibitors or pharmaceutical salts thereof may be formulated into pharmaceutical compositions for administration to animals or humans. These pharmaceutical compositions, which comprise an amount of the protein inhibitor effective to treat or prevent a protein kinase-mediated condition and a pharmaceutically acceptable carrier, are another embodiment of the present invention.

In another aspect, the invention provides a kit comprising a compound capable of inhibiting kinase activity selected from one or more compounds of formula A, and instructions for use in treating cancer.

EXAMPLES

The compounds and processes of the present invention will be better understood in connection with the following examples, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

Synthesis of Compounds of Formula I

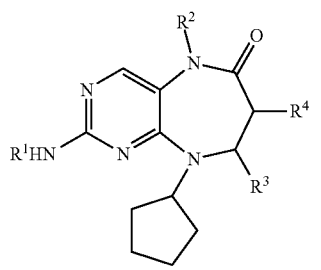

-continued

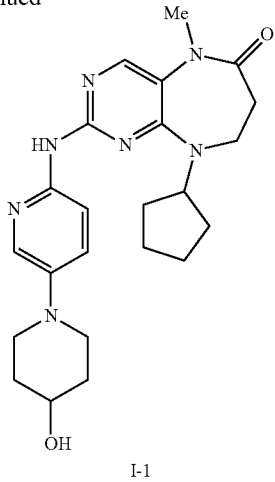

I-1

To a stirred solution of methyl 3-(cyclopentylamino)propanoate (6.0 g, 35.0 mmol) and potassium carbonate (7.3 g, 52.6 mmol) in 150 mL of acetone was slowly added 2,4-dichloro-5-nitropyrimidine (6.8 g, 35.0 mmol, dissolved in 50 mL acetone) at 0° C. The reaction mixture was stirred and allowed to approach room temperature over a period of 12-16 hours. After the reaction was complete as monitored by reverse phase analytical liquid-chromatography electrospray mass spectrometry (LC-MS), the solvent was removed in vacuo. The resulting slurry was then diluted in water and brine and extracted with dichloromethane. The combined organic layers were dried over anhydrous sodium sulfate and concentrated. The residue was purified by silica-gel chromatography with dichloromethane:methanol (100:1 v/v) to give the title compound I-1-a (8.0 g, 69%), MS (ESI) m/z 329 (M+H)+.

A mixture of compound I-1-a (7.2 g, 21.9 mmol) and iron power (2.5 g, 43.8 mmol) in 200 mL of acetic acid was heated at 50° C. After the reaction was complete, as monitored by LC-MS, the solvent was removed in vacuo. The residue was then purified by silica-gel chromatography with dichloromethane:methanol (20:1 v/v) to give the title compound I-1-b (2.5 g, 42%), MS (ESI) m/z 267 (M+H)+.

To a stirred solution of compound I-1-b (276 mg, 1.0 mmol) and MeI (71 µL, 1.1 mmol) in 10 mL of dimethyl acetamide (DMA) was added NaH (50 mg, 60% suspension in mineral oil) at −10° C. and the reaction was gradually warmed to 0° C. After the reaction was complete as monitored by LC-MS, the solution was poured into ice-water and extracted with ethyl acetate. The combined organic layers were washed with brine, dried over anhydrous sodium sulfate, and concentrated in vacuo. The residue was purified by silica-gel chromatography with dichloromethane:methanol (50:1 v/v) to give the title compound I-1-c (252 mg, 90%), MS (ESI) m/z 281 (M+H)+.

A mixture of I-1-c (26 mg, 0.09 mmol), 1-(6-aminopyridin-3-yl)piperidin-4-ol (22 mg, 0.12 mmol), X-Phos (4.0 mg), Pd$_2$(dba)$_3$ (5.0 mg) and K$_2$CO$_3$ (38.4 mg, 0.28 mmol) in 1.5 mL of t-BuOH was heated at 100° C. in a seal tube for 8 h. The reaction was then filtered through celite, eluted with dichloromethane, and concentrated in vacuo. The residue was then purified by reverse-phase prep-HPLC using a water (0.05% TFA)/acetonitrile (0.05% TFA) gradient to afford the title compound I-1 as the TFA salt (37 mg, 70%). $^1$H NMR (600 MHz, DMSO-d$_6$) δ 9.00 (s, br, 1H), 8.03 (s, 1H), 7.97 (d, J=9.02 Hz, 1H), 7.94 (d, J=2.95 Hz, 1H), 7.38 (dd, J=9.09, 2.87 Hz, 1H), 4.77 (p, J=8.34, 8.34, 8.32, 8.32 Hz, 1H), 4.67 (d, J=4.20 Hz, 1H), 3.63-3.58 (m, 3H), 3.44 (td, J=9.91, 4.15, 4.15 Hz, 2H), 3.16 (s, 3H), 2.79 (ddd, J=12.57, 10.08, 2.89 Hz, 2H), 2.58-2.55 (m, 2H), 1.97-1.89 (m, 2H), 1.86-1.80 (m, 2H), 1.73-1.64 (m, 2H), 1.62-1.55 (m, 4H), 1.53-1.46 (m, 2H). MS (ESI) m/z 438 (M+H)+.

Compounds (I-2-I-40) were synthesized using the above procedure.

I-20: $^1$H NMR (400 MHz, CDCl$_3$) δ 1.57-2.01 (m, 6H), 2.10-2.30 (m, 2H), 2.41 (t, J=12 Hz, 2H), 3.10-3.20 (m, 3H), 3.34 (s, 3H), 3.93-3.97 (m, 2H), 4.63 (t, J=8 Hz, 2H), 7.73 (s, 1H), 7.77-7.80 (m, 1H), 8.14 (s, 1H), 8.36 (d, J=8 Hz, 1H), 8.48 (d, J=12 Hz, 1H), 8.60 (d, J=8 Hz, 1H), 9.13 (d, J=8 Hz, 1H), 12.36 (bs, 1H).

I-21: $^1$H NMR (400 MHz, DMSO) δ 1.00-1.10 (m, 4H), 1.20-1.25 (m, 2H), 1.30-1.56 (m, 7H), 1.90-2.00 (m, 3H), 2.90-3.00 (m, 1H), 3.16 (s, 3H), 7.48-7.50 (m, 1H), 7.65-7.73 (m, 2H), 7.82 (d, J=8 Hz, 1H), 8.18 (s, 1H), 8.40 (d, J=8 Hz, 1H), 8.88 (bs, 1H), 9.35 (s, 1H).

I-22: $^1$H NMR (400 MHz, CDCl$_3$) δ 1.43-1.49 (m, 4H), 1.57-1.66 (m, 4H), 1.76-1.90 (m, 4H), 2.10-2.20 (m, 2H), 2.34 (t, J=12 Hz, 2H), 2.60-2.80 (m, 2H), 2.85 (s, 3H), 3.08-3.10 (m, 2H), 3.29 (s, 3H), 3.49 (s, 1H), 3.50-3.60 (m, 2H), 3.85-3.87 (m, 1H), 3.90 (s, 3H), 4.11-4.16 (m, 1H), 6.98 (d, J=8 Hz, 1H), 7.04 (s, 1H), 7.72-7.75 (m, 2H), 10.41 (bs, 1H).

I-23: $^1$H NMR (400 MHz, CD$_3$OD) δ 1.53-1.67 (m, 8H), 1.75-1.79 (m, 2H), 1.87-1.96 (m, 4H), 2.17-2.21 (m, 2H), 3.10-3.20 (m, 1H), 3.30 (s, 3H), 3.97 (s, 3H), 4.02-4.06 (m, 1H), 7.67-7.69 (m, 2H), 7.99-8.01 (m, 1H), 8.05 (s, 1H).

I-24: $^1$H NMR (400 MHz, CDCl$_3$) δ 1.59-1.98 (m, 11H), 2.10-2.20 (m, 2H), 2.36 (t, J=12 Hz, 1H), 3.09-3.15 (m, 1H), 3.29 (s, 3H), 3.89-3.92 (m, 1H), 4.50-4.60 (m, 1H), 6.00 (bs, 2H), 7.65 (s, 1H), 7.69 (d, J=8 Hz, 2H), 7.80 (d, J=8 Hz, 2H), 11.7 (bs, 1H).

I-26: $^1$H NMR (400 MHz, CDCl$_3$) δ 1.51-2.13 (m, 14H), 2.95-3.01 (m, 1H), 3.24 (s, 3H), 3.50-3.58 (m, 2H), 3.81-3.84 (m, 2H), 3.89-4.03 (m, 2H), 5.23 (bs, 1H), 5.30 (bs, 1H), 7.87 (s, 1H).

I-27: $^1$H NMR (400 MHz, CDCl$_3$) δ 1.15-1.25 (m, 1H), 1.43-1.67 (m, 7H), 1.77-1.91 (m, 4H), 2.10-2.20 (m, 1H), 2.36 (t, J=12 Hz, 1H), 3.10-3.11 (m, 1H), 3.29 (s, 3H), 3.83-3.89 (m, 1H), 3.92 (s, 3H), 4.16-4.21 (m, 1H), 7.30 (d, J=8 Hz, 1H), 7.73 (s, 1H), 7.46 (s, 1H), 7.71 (d, J=8 Hz, 1H), 10.37 (bs, 1H).

I-30: $^1$H NMR (400 MHz, CDCl$_3$) δ 0.86-0.88 (m, 1H), 1.25-1.29 (m, 3H), 1.54-1.70 (m, 7H), 1.81-1.99 (m, 10H), 2.17-2.22 (m, 3H), 2.36 (t, J=12 Hz, 3H), 3.10 (m, 1H), 3.27 (s, 3H), 3.85-3.91 (m, 1H), 4.30-4.34 (m, 1H), 5.30 (s, 1H), 7.48 (s, 1H).

I-34: $^1$H NMR (400 MHz, CDCl$_3$) δ 1.19-1.27 (m, 4H), 1.50-1.92 (m, 8H), 2.10-2.17 (m, 1H), 2.30-2.40 (m, 1H), 2.88 (s, 3H), 3.08-3.10 (m, 3H), 3.26 (s, 3H), 3.32-3.44 (m, 2H), 3.59-3.75 (m, 4H), 3.81 (s, 3H), 3.88-3.92 (m, 2H), 6.47 (s, 1H), 6.48 (d, J=12 Hz, 1H), 7.31 (d, 1H), 7.60 (s, 1H), 10.51 (bs, 1H).

I-35: $^1$H NMR (400 MHz, CDCl$_3$) δ 1.39-1.44 (m, 4H), 1.56-1.92 (m, 7H), 2.10-2.20 (m, 1H), 2.37 (t, J=12 Hz, 1H), 3.04 (d, J=4 Hz, 3H), 3.10 (t, J=4 Hz, 3H), 3.29 (s, 3H), 3.82-3.84 (m, 1H), 3.91 (s, 3H), 4.12-4.19 (m, 1H), 6.26 (bs, 1H), 7.25 (d, J=8 Hz, 1H), 7.43 (s, 1H), 7.62 (d, J=8 Hz, 1H), 7.71 (s, 1H), 10.47 (bs, 1H).

I-37: $^1$H NMR (400 MHz, CDCl$_3$) δ 1.50-1.70 (m, 6H), 1.80-2.01 (m, 6H), 2.10-2.30 (m, 1H), 2.39 (t, J=12 Hz, 1H), 2.90 (s, 3H), 2.20-2.30 (m, 1H), 3.39 (s, 3H), 3.90-4.00 (m, 1H), 4.30-4.50 (m, 2H), 7.40 (bs, 2H), 7.78 (d, J=8 Hz, 1H), 7.82 (s, 1H), 8.10 (d, J=8 Hz, 1H), 8.70 (s, 1H).

Example 2

Synthesis of Compounds of Formula II

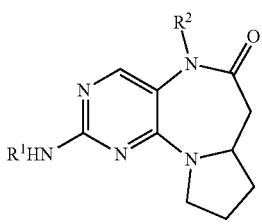

Scheme 2

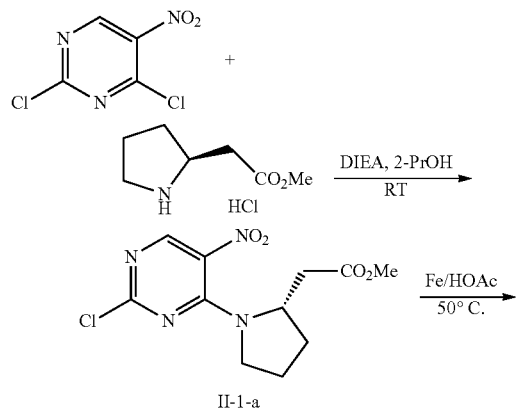

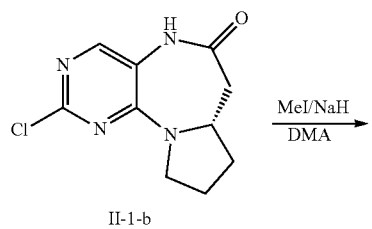

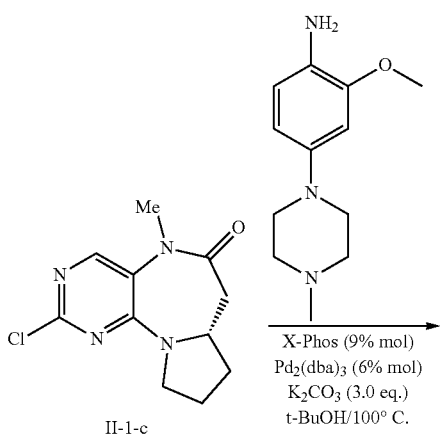

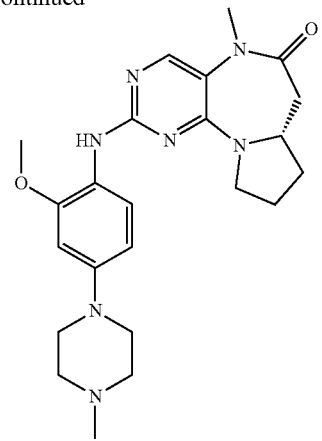

To a stirred solution of (S)-methyl 2-(pyrrolidin-2-yl)acetate hydrochloride (467 mg, 2.6 mmol) and DIEA (1.36 mL, 7.8 mmol) in of 2-PrOH (12 mL) was added 2,4-dichloro-5-nitropyrimidine (756.5 mg, 3.9 mmol) in one portion at room temperature. Then the reaction was stirred at RT. After the reaction was complete as monitored by LC-MS, the resulting mixture was diluted with ethyl acetate and washed with water and brine, the organic layer was dried over anhydrous sodium sulfate and concentrated in vacuo. The residue was purified by silica-gel column chromatography with ethyl acetate and hexane (1/10, v/v) to give the title compound II-1-a (391 mg, 50%), MS (ESI) m/z 301 $(M+H)^+$.

A mixture of compound II-1-a (390 mg, 1.3 mmol) and iron power (728 mg, 13.0 mmol) in acetic acid (18 mL) was heated at 50° C. After the reaction was complete, the mixture was concentrated in vacuo. Then the residue was purified by silica-gel column chromatography with methanol and dichloromethane (1/25, v/v) to give the title compound II-1-b (212 mg, 68%), MS (ESI) m/z 239 $(M+H)^+$.

To a stirred solution of compound II-1-b (95 mg, 0.4 mmol) and MeI (37 µL, 0.6 mmol) in dimethyl acetamide (DMA, 4.0 mL) was added NaH (32 mgs, 60% suspension in mineral oil) at −10° C. and the reaction was gradually warmed up to 0° C. After the reaction was complete as monitored by LC-MS, the solution was poured into ice-water and extracted with ethyl acetate. The organic layer was washed with brine and dried over anhydrous sodium sulfate. The solvent was removed in vacuo and the crude product II-1-c was used in next step without further purification. MS (ESI) m/z 253 $(M+H)^+$.

A mixture of II-1-c (30 mg, 0.12 mmol), 2-methoxy-4-(4-methylpiperazin-1-yl)benzenamine (26.5 mg, 0.12 mmol), X-Phos (5.1 mg), $Pd_2(dba)_3$ (6.6 mg) and $K_2CO_3$ (49.8 mg, 0.36 mmol) in t-BuOH (1.5 mL) was heated at 100° C. in a seal tube for 4 h. Then the reaction was filtered through celite and eluted with dichloromethane. The solvent was removed in vacuo and the residue was purified by reverse-phase prep-HPLC using a water (0.05% TFA)/acetonitrile (0.05% TFA) gradient to afford the title compound II-1 as TFA salt (19 mg). $^1$H NMR (600 MHz, CD$_3$OD) δ 7.76 (s, 1H), 7.62 (s, br, 1H), 6.77 (d, J=2.4 Hz, 1H), 6.67 (dd, J=2.4, 8.4 Hz, 1H), 4.08-4.06 (m, 1H), 3.95-3.85 (m, 6H), 3.77 (dd, J=8.4, 12.6 Hz, 1H), 3.65-3.60 (m, 2H), 3.40-3.25 (m, 5H), 3.15-3.05 (m, 2H), 2.98 (s, 3H), 2.90 (dd, J=10.8, 14.4 Hz, 1H), 2.75 (d, J=15 Hz, 1H), 2.31-2.27 (m, 1H), 2.09-2.06 (m, 1H), 1.98-1.93 (m, 1H), 1.75-1.72 (m, 1H). MS (ESI) m/z 438 (M+H)⁺

Compounds (II-2-II-7) were synthesized using the above procedure.

Example 3

Synthesis of Compounds of Formula III

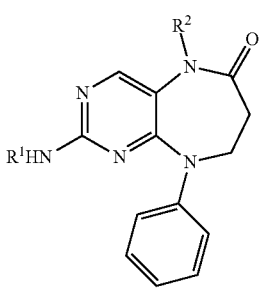

Scheme 3

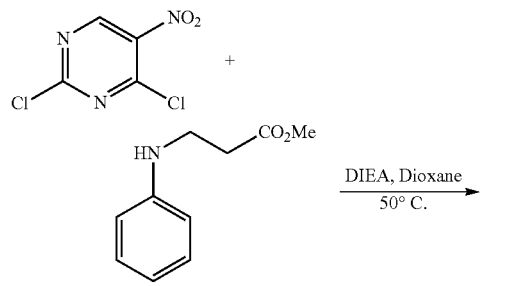

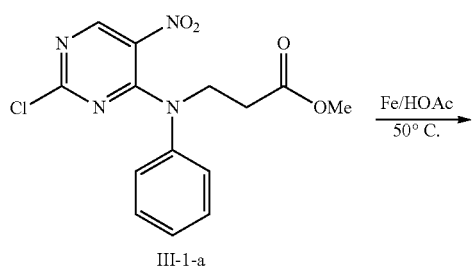

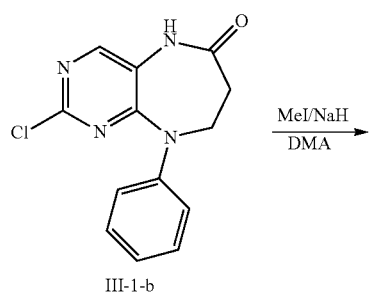

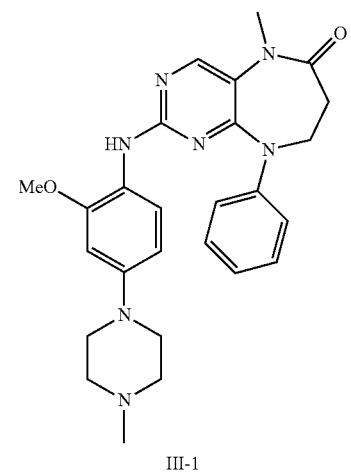

A mixture of methyl 3-(phenylamino)propanoate (1.42 g, 7.93 mmol), DIEA (2.76 mL, 15.86 mmol) and 2,4-dichloro-5-nitropyrimidine (2.30 g, 11.90 mmol) in dioxane (40 mL) was heated at 50° C. for 1 h. After the reaction was complete as monitored by TLC, the reaction solution was concentrated in vacuo and the residue was purified by silica-gel column chromatography with ethyl acetae and hexane (1/20, v/v) to give the title compound III-1-a (2.5 g, 91%), MS (ESI) m/z 337 (M+H)⁺.

A mixture of compound III-1-a (2.5 g, 7.4 mmol) and iron power (4.16 g, 74.0 mmol) in 100 mL of acetic acid was heated at 50° C. for 12 h. After the reaction was complete as monitored by LC-MS, the mixture was concentrated in vacuo. Then the residue was poured into ice-water and the solid precipitated. The precipitate was filtered, washed with water and air dried to give the title compound II-1-b (1.75 g, 86%), MS (ESI) m/z 275 (M+H)⁺.

To a stirred suspension of compound III-1-b (549.4 mg, 2.0 mmol) and MeI (0.19 mL, 3.0 mmol) in 25.0 mL of dimethyl acetamide (DMA) was added NaH (240 mg, 60% suspension in mineral oil) at −10° C. and the reaction was gradually warmed to 0° C. After the reaction was complete, the solution was poured into ice-water and extracted with ethyl acetate. The organic layer was washed with brine and dried over anhydrous sodium sulfate. Concentrated and the crude product III-1-c was used in next step without further purification. MS (ESI) m/z 289 (M+H)⁺.

A mixture of III-1-c (29 mg, 0.1 mmol), 2-methoxy-4-(4-methylpiperazin-1-yl)benzenamine (22 mg, 0.1 mmol), X-Phos (4.3 mg), Pd$_2$(dba)$_3$ (5.5 mg) and K$_2$CO$_3$ (41.5 mg, 0.3 mmol) in 1.2 mL of t-BuOH was heated at 100° C. in a seal tube for 4 h. Then the reaction was filtered through celite and eluted with dichloromethane. Concentrated and the residue was purified by reverse-phase prep-HPLC using a water (0.05% TFA)/acetonitrile (0.05% TFA) gradient to afford the title compound III-1 as TFA salt (14 mg). $^1$H NMR (600 MHz, CD$_3$OD) δ 8.03 (s, br, 1H), 7.56-7.53 (m, 2H), 7.50-7.47 (m, 1H), 7.36 (d, J=7.2 Hz, 2H), 6.94 (d, J=8.4 Hz, 1H), 6.62 (s, 1H), 6.08 (s, br, 1H), 4.17 (t, J=5.4 Hz, 2H), 3.84 (s, 3H), 3.78-3.72 (m, 2H), 3.63-3.58 (m, 2H), 3.35 (s, 3H), 3.28-3.22 (m, 2H), 3.06 (t, J=4.8 Hz, 2H), 3.04-2.98 (m, 2H), 2.97 (s, 3H). MS (ESI) m/z 474 (M+H)$^+$.

Compounds (III-2-III-5) were synthesized using the above procedure.

Example 4

Synthesis of Compounds of Formula IV

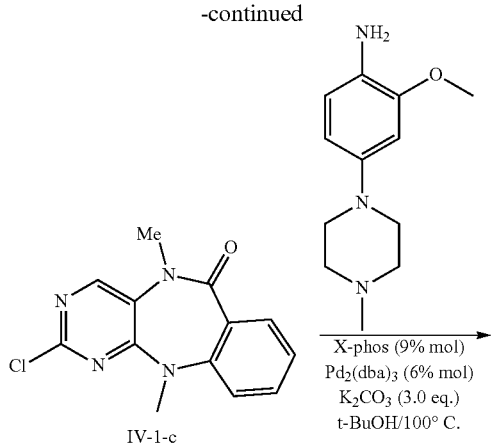

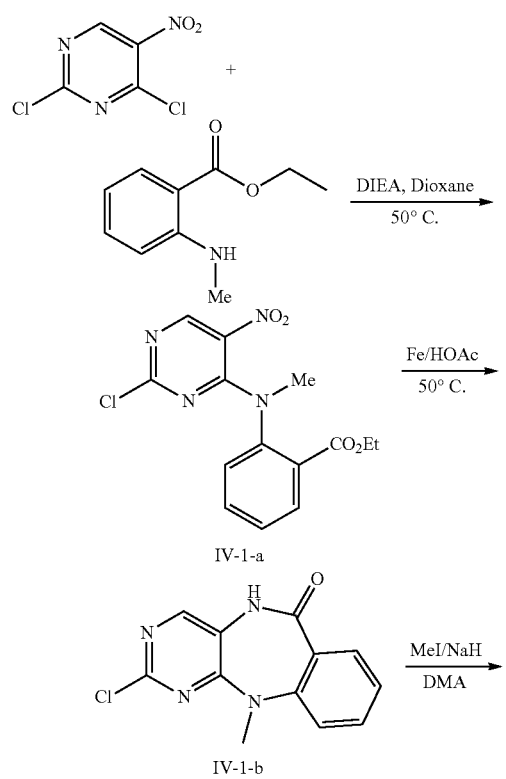

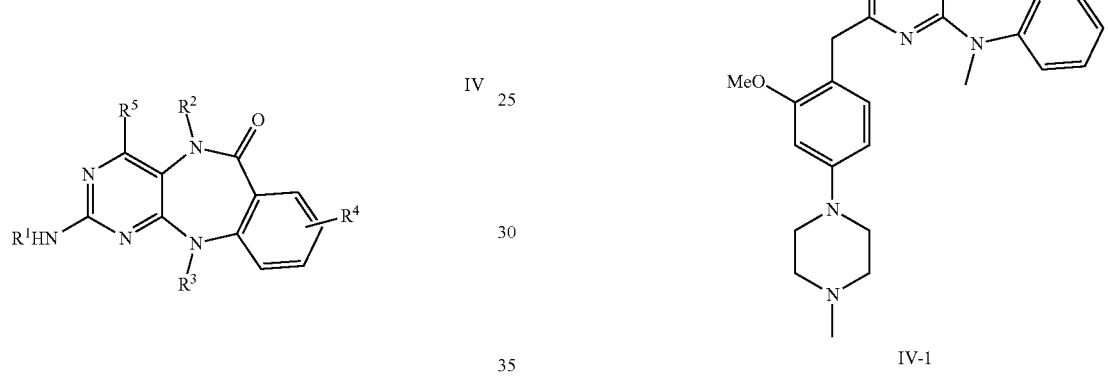

A mixture of ethyl 2-(methylamino)benzoate (1.44 g, 8.0 mmol), DIEA (2.8 mL, 16.0 mmol) and 2,4-dichloro-5-nitropyrimidine (2.30 g, 12.0 mmol) in 40 mL of dioxane was heated at 50° C. for 6 h. After the reaction was complete as monitored by TLC, the reaction solution was concentrated and the residue was purified by silica-gel column chromatography with ethyl acetae and hexane (1/20, v/v) to give the title compound IV-1-a (2.51 g, 93%), MS (ESI) m/z 337 (M+H)$^+$.

A mixture of compound IV-1-a (2.35 g, 6.98 mmol) and iron power (3.9 g, 69.8 mmol) in 100 mL of acetic acid was heated at 50° C. for 9 h. After the reaction was complete as monitored by LC-MS, the mixture was concentrated. Then the residue was poured into ice-water and the solid precipitated. The precipitate was filtered, washed with water and dried by air to give the title compound IV-1-b (1.55 g, 85%), MS (ESI) m/z 261 (M+H)$^+$.

To a stirred suspension of compound IV-1-b (688 mg, 2.64 mmol) and MeI (0.25 mL, 4.0 mmol) in 40.0 mL of dimethyl acetamide (DMA) was added NaH (360 mg, 60% suspension in mineral oil) at −10° C. and the reaction was gradually warmed up to 0° C. After the reaction was complete as monitored by LC-MS, the solution was poured into ice-water and the solid precipitated. The precipitate was filtered, washed with water and air dried to give the title compound IV-1-c (563 mg, 77%), MS (ESI) m/z 275 (M+H)$^+$.

A mixture of IV-1-c (28 mg, 0.1 mmol), 2-methoxy-4-(4-methylpiperazin-1-yl)benzenamine (22 mg, 0.1 mmol), X-Phos (4.3 mg), Pd$_2$(dba)$_3$ (5.5 mg) and K$_2$CO$_3$ (41.5 mg, 0.3 mmol) in 1.2 mL of t-BuOH was heated at 100° C. in a seal tube for 4 h. Then the reaction was filtered through celite and eluted with dichloromethane. The dichloromethane was removed in vacuo and the resulting crude product was purified by reverse-phase prep-HPLC using a water (0.05% TFA)/acetonitrile (0.05% TFA) gradient to afford the title compound IV-1 as TFA salt (20 mg). $^1$H NMR (600 MHz, CD$_3$OD) δ 8.1 (s, 1H), 7.78 (dd, J=1.2, 7.8 Hz, 1H), 7.71 (d, J=7.2 Hz, 1H), 7.57-7.54 (m, 1H), 7.28-7.23 (m, 2H), 6.76 (d, J=2.4 Hz, 1H), 6.67 (dd, J=1.2, 8.4 Hz, 1H), 3.92-3.86 (m, 5H), 3.66-3.60 (m, 2H), 3.46 (s, 3H), 3.45 (s, 3H), 3.28-3.24 (m, 2H), 3.14-3.06 (m, 2H), 2.97 (s, 3H). MS (ESI) m/z 460 (M+H)$^+$.

Compounds (IV-2-IV-30) were synthesized using the above procedure.

Example 4.2

Synthesis of Compounds of Formula IV-II

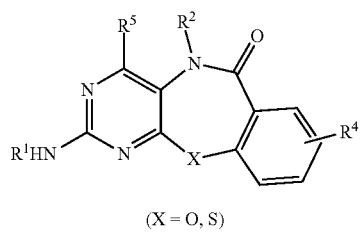

(X = O, S)

Scheme 4.2

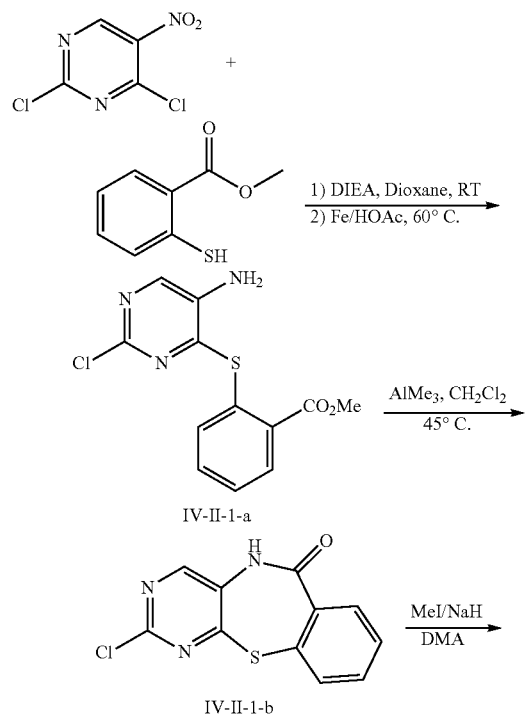

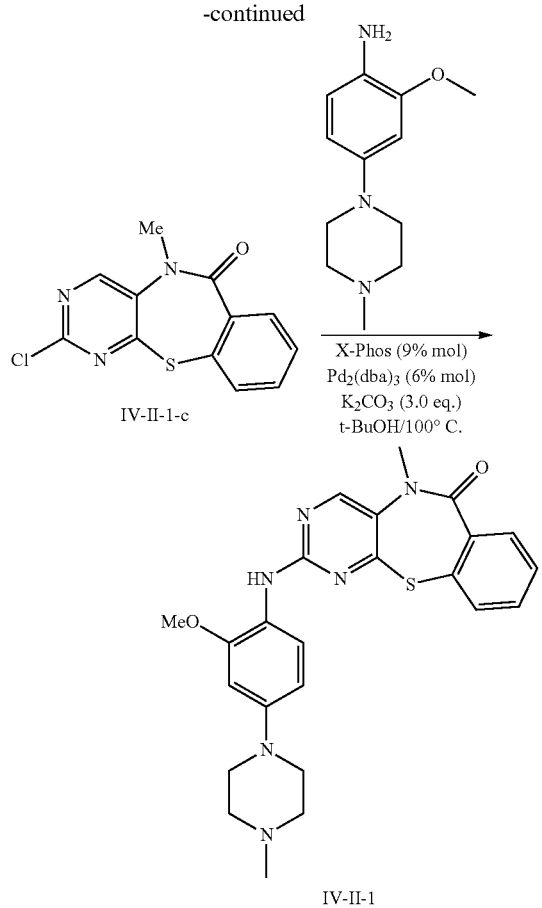

Example of Synthesis of Compound IV-II-1

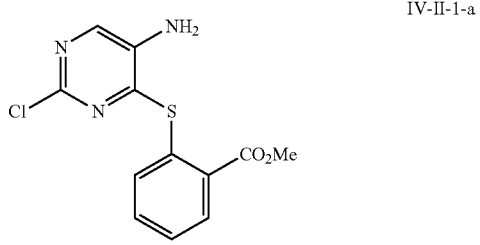 [SMILES: COC(=O)c1ccccc1Sc1nc(Cl)ncc1N]

To a stirred solution of 2,4-dichloro-5-nitropyrimidine (2.91 g, 15.0 mmol) and DIEA (3.5 mL, 20.0 mmol) in 45 mL of dioxane was added methyl 2-mercaptobenzoate (1.68 g, 10.0 mmol) in 15 mL of dioxane at RT. After the reaction was complete as monitored by TLC, the reaction was diluted with ethyl acetate and washed brine. The organic layer was dried over anhydrous Na$_2$SO$_4$ and then the solvent was removed in vacuo. The residue was dissolved in 120 mL of acetic acid and 5.6 g of iron powder was added. The resulting mixture was heated at 60° C. for 7 h. After the reaction was complete as monitored by LC-MS, the mixture was concentrated. Then the residue was poured into ice-water and the solid precipitated. The precipitate was filtered, washed with water and dried by air to give the title compound IV-II-1-a (2.51 g, 85%), MS (ESI) m/z 297 (M+H)$^+$.

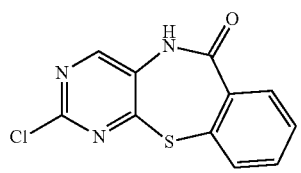

IV-II-1-b

To a stirred solution of compound IV-II-1-a (2.22 g, 7.5 mmol) in 75 mL of dichloromethane was added trimethylaluminum solution (2.0 M in toluene, 6.0 mL) at 0° C. After 15 minutes, the ice-bath was removed and the reaction was stirred at RT for 1 h. Then the mixture was reflux at 45° C. until the reaction was complete as monitored by LC-MS. The reaction was cooled down and quenched by 1 N HCl aqueous solution at 0° C. After removing the organic solvent, the residue was poured into ice-water and the solid precipitated. The precipitate was filtered, washed with water and dried by air to give the title compound IV-II-1-b (1.74 g, 88%), MS (ESI) m/z 264 (M+H)+.

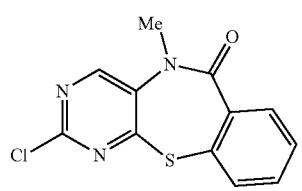

IV-II-1-c

To a stirred suspension of compound IV-II-1-b (394.5 mg, 1.5 mmol) and MeI (0.11 mL, 1.8 mmol) in 15.0 mL of dimethyl acetamide (DMA) was added NaH (120 mg, 60% suspension in mineral oil) at −10° C. and the reaction was gradually warmed up to 0° C. After the reaction was complete as monitored by LC-MS, the solution was poured into ice-water and the solid precipitated. The precipitate was filtered, washed with water and air dried to give the title compound IV-II-1-c (321 mg, 77%), MS (ESI) m/z 278 (M+H)+.

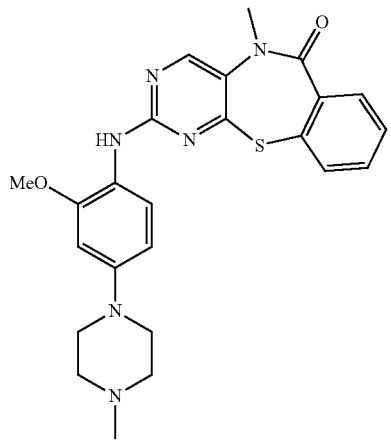

IV-II-1

A mixture of IV-II-1-c (28 mg, 0.1 mmol), 2-methoxy-4-(4-methylpiperazin-1-yl)benzenamine (22 mg, 0.1 mmol), X-Phos (4.3 mg), Pd$_2$(dba)$_3$ (5.5 mg) and K$_2$CO$_3$ (41.5 mg, 0.3 mmol) in 1.2 mL of t-BuOH was heated at 100° C. in a seal tube for 4 h. Then the reaction was filtered through celite and eluted with dichloromethane. The dichloromethane was removed in vacuo and the resulting crude product was purified by preparative TLC with 3.5 N ammonia methanol solution and dichloromethane (1/25, v/v) to give the title compound IV-1 (8 mg). $^1$H NMR (600 MHz, CDCl$_3$) δ 8.32 (s, 1H), 8.18 (d, J=8.4 Hz, 1H), 7.80 (dd, J=1.8, 7.8 Hz, 1H), 7.61 (s, 1H), 7.51 (dd, J=1.8, 7.8 Hz, 1H), 7.40-7.34 (m, 2H), 6.54 (dd, J=1.8, 8.4 Hz, 1H), 6.52 (d, J=1.8 Hz, 1H), 3.85 (s, 3H), 3.55 (s, 3H), 3.23 (s, br, 4H), 2.69 (s, br, 4H), 2.43 (s, 3H). MS (ESI) m/z 463 (M+H)+.

TABLE 1

Compounds of the invention

| Compound ID | Structure | Spectroscopy |
|---|---|---|
| I-1 | 9-cyclopentyl-2-(5-(4-hydroxypiperidin-1-yl)pyridin-2-ylamino)-5-methyl-8,9-dihydro-5H-pyrimido[4,5-b][1,4]diazepin-6(7H)-one | MS (ESI) m/z 438 (M + H)+ |

TABLE 1-continued

Compounds of the invention

| Compound ID | Structure | Spectroscopy |
|---|---|---|
| I-2 | 4-(9-cyclopentyl-6-oxo-6,7,8,9-tetrahydro-5H-pyrimido[4,5-b][1,4]diazepin-2-ylamino)-3-methoxy-N-(1-methylpiperidin-4-yl)benzamide | MS (ESI) m/z 494 (M + H)+ |
| I-3 | 4-(9-cyclopentyl-5-methyl-6-oxo-6,7,8,9-tetrahydro-5H-pyrimido[4,5-b][1,4]diazepin-2-ylamino)-3-methoxy-N-(1-methylpiperidin-4-yl)benzamide | MS (ESI) m/z 508 (M + H)+ |
| I-4 | 4-(9-cyclopentyl-5,8-dimethyl-6-oxo-6,7,8,9-tetrahydro-5H-pyrimido[4,5-b][1,4]diazepin-2-ylamino)-3-methoxy-N-(1-methylpiperidin-4-yl)benzamide | MS (ESI) m/z 522 (M + H)+ |
| I-5 | 4-(9-cyclopentyl-5,7-dimethyl-6-oxo-6,7,8,9-tetrahydro-5H-pyrimido[4,5-b][1,4]diazepin-2-ylamino)-3-methoxy-N-(1-methylpiperidin-4-yl)benzamide | MS (ESI) m/z 522 (M + H)+ |

TABLE 1-continued

Compounds of the invention

| Compound ID | Structure | Spectroscopy |
|---|---|---|
| I-6 | 9-cyclopentyl-2-(4-(4-hydroxypiperidin-1-yl)-2-methoxyphenylamino)-5-methyl-8,9-dihydro-5H-pyrimido[4,5-b][1,4]diazepin-6(7H)-one | MS (ESI) m/z 467 (M + H)⁺ |
| I-7 | 9-cyclopentyl-2-(4-((2-hydroxyethyl)(methyl)amino)-2-methoxyphenylamino)-5-methyl-8,9-dihydro-5H-pyrimido[4,5-b][1,4]diazepin-6(7H)-one | MS (ESI) m/z 441 (M + H)⁺ |
| I-8 | 9-cyclopentyl-2-(4-((3-hydroxypropyl)(methyl)amino)-2-methoxyphenylamino)-5-methyl-8,9-dihydro-5H-pyrimido[4,5-b][1,4]diazepin-6(7H)-one | MS (ESI) m/z 455 (M + H)⁺ |
| I-9 | 9-cyclopentyl-2-(4-(4-hydroxy-4-methylpiperidin-1-yl)-2-methoxyphenylamino)-5-methyl-8,9-dihydro-5H-pyrimido[4,5-b][1,4]diazepin-6(7H)-one | MS (ESI) m/z 481 (M + H)⁺ |

TABLE 1-continued

Compounds of the invention

| Compound ID | Structure | Spectroscopy |
|---|---|---|
| I-10 | 9-cyclopentyl-2-(2-ethoxy-4-(4-hydroxypiperidin-1-yl)phenylamino)-5-methyl-8,9-dihydro-5H-pyrimido[4,5-b][1,4]diazepin-6(7H)-one | MS (ESI) m/z 481 (M + H)+ |
| I-11 | 9-cyclopentyl-2-(4-(4-hydroxypiperidin-1-yl)-2-isopropoxyphenylamino)-5-methyl-8,9-dihydro-5H-pyrimido[4,5-b][1,4]diazepin-6(7H)-one | MS (ESI) m/z 495 (M + H)+ |
| I-12 | 9-cyclopentyl-2-(4-(4-(2-hydroxyethyl)piperazin-1-yl)-2-methoxyphenylamino)-5-methyl-8,9-dihydro-5H-pyrimido[4,5-b][1,4]diazepin-6(7H)-one | MS (ESI) m/z 496 (M + H)+ |
| I-13 | 9-cyclopentyl-2-(2-ethoxy-4-(4-hydroxypiperidin-1-yl)phenylamino)-5-ethyl-8,9-dihydro-5H-pyrimido[4,5-b][1,4]diazepin-6(7H)-one | MS (ESI) m/z 495 (M + H)+ |

TABLE 1-continued

Compounds of the invention

| Compound ID | Structure | Spectroscopy |
|---|---|---|
| I-14 | 9-cyclopentyl-5-ethyl-2-(4-(4-hydroxypiperidin-1-yl)-2-isopropoxyphenylamino)-8,9-dihydro-5H-pyrimido[4,5-b][1,4]diazepin-6(7H)-one | MS (ESI) m/z 509 (M + H)+ |
| I-15 | 9-cyclopentyl-5-ethyl-2-(5-(4-hydroxypiperidin-1-yl)pyridin-2-ylamino)-8,9-dihydro-5H-pyrimido[4,5-b][1,4]diazepin-6(7H)-one | MS (ESI) m/z 452 (M + H)+ |
| I-16 | 9-cyclopentyl-2-(2-methoxy-4-(4-(4-methylpiperazin-1-yl)piperidin-1-yl)phenylamino)-5,8-dimethyl-8,9-dihydro-5H-pyrimido[4,5-b][1,4]diazepin-6(7H)-one | MS (ESI) m/z 563 (M + H)+ |
| I-17 | 9-cyclopentyl-2-(2-methoxy-4-(4-(4-methylpiperazin-1-yl)piperidin-1-yl)phenylamino)-8-methyl-8,9-dihydro-5H-pyrimido[4,5-b][1,4]diazepin-6(7H)-one | MS (ESI) m/z 549 (M + H)+ |

TABLE 1-continued

Compounds of the invention

| Compound ID | Structure | Spectroscopy |
|---|---|---|
| I-18 | 9-cyclopentyl-2-(2-methoxy-4-(4-methylpiperazin-1-yl)phenylamino)-5,8-dimethyl-8,9-dihydro-5H-pyrimido[4,5-b][1,4]diazepin-6(7H)-one | MS (ESI) m/z 480 (M + H)+ |
| I-19 | 9-cyclopentyl-2-(2-methoxy-4-(4-methylpiperazin-1-yl)phenylamino)-8-methyl-8,9-dihydro-5H-pyrimido[4,5-b][1,4]diazepin-6(7H)-one | MS (ESI) m/z 466 (M + H)+ |
| I-20 | 10-cyclopentyl-5-methyl-2-(quinolin-6-ylamino)-6a,7,8,9,9a,10-hexahydrocyclopenta[e]pyrimido[5,4-b][1,4]diazepin-6(5H)-one | MS (ESI) m/z 429 (M + H)+. |
| I-21 | 10-cyclopentyl-5-methyl-2-(quinolin-5-ylamino)-6a,7,8,9,9a,10-hexahydrocyclopenta[e]pyrimido[5,4-b][1,4]diazepin-6(5H)-one | MS (ESI) m/z 429 (M + H)+. |

TABLE 1-continued

Compounds of the invention

| Compound ID | Structure | Spectroscopy |
|---|---|---|
| I-22 | 10-cyclopentyl-2-(2-methoxy-4-(4-methylpiperazine-1-carbonyl)phenylamino)-5-methyl-6a,7,8,9,9a,10-hexahydrocyclopenta[e]pyrimido[5,4-b][1,4]diazepin-6(5H)-one | MS (ESI) m/z 534 (M + H)+. |
| I-23 | 4-(10-cyclopentyl-5-methyl-6-oxo-5,6,6a,7,8,9,9a,10-octahydrocyclopenta[e]pyrimido[5,4-b][1,4]diazepin-2-ylamino)-3-methoxybenzoic acid | MS (ESI) m/z 452 (M + H)+. |
| I-24 | 4-(10-cyclopentyl-5-methyl-6-oxo-5,6,6a,7,8,9,9a,10-octahydrocyclopenta[e]pyrimido[5,4-b][1,4]diazepin-2-ylamino)benzamide | MS (ESI) m/z 421 (M + H)+. |
| I-25 | 10-cyclopentyl-2-(4-(4-hydroxypiperidine-1-carbonyl)-2-methoxyphenylamino)-5-methyl-6a,7,8,9,9a,10-hexahydrocyclopenta[e]pyrimido[5,4-b][1,4]diazepin-6(5H)-one | MS (ESI) m/z 535 (M + H)+. |

TABLE 1-continued

Compounds of the invention

| Compound ID | Structure | Spectroscopy |
|---|---|---|
| I-26 | 10-cyclopentyl-2-(2-hydroxyethylamino)-5-methyl-6a,7,8,9,9a,10-hexahydrocyclopenta[e]pyrimido[5,4-b][1,4]diazepin-6(5H)-one | MS (ESI) m/z 346 (M + H)+. |
| I-27 | 4-(10-cyclopentyl-5-methyl-6-oxo-5,6,6a,7,8,9,9a,10-octahydrocyclopenta[e]pyrimido[5,4-b][1,4]diazepin-2-ylamino)-3-methoxybenzamide | MS (ESI) m/z 451 (M + H)+. |
| I-28 | 4-(10-cyclopentyl-5-methyl-6-oxo-5,6,6a,7,8,9,9a,10-octahydrocyclopenta[e]pyrimido[5,4-b][1,4]diazepin-2-ylamino)-N-(4-hydroxycyclohexyl)-3-methoxybenzamide | MS (ESI) m/z 549 (M + H)+. |
| I-29 | 4-(10-cyclopentyl-5-methyl-6-oxo-5,6,6a,7,8,9,9a,10-octahydrocyclopenta[e]pyrimido[5,4-b][1,4]diazepin-2-ylamino)-3-methoxy-N-(1-methylpiperidin-4-yl)benzamide | MS (ESI) m/z 548 (M + H)+ |

TABLE 1-continued

Compounds of the invention

| Compound ID | Structure | Spectroscopy |
|---|---|---|
| I-30 | 10-cyclopentyl-2-(4-hydroxycyclohexylamino)-5-methyl-6a,7,8,9,9a,10-hexahydrocyclopenta[e]pyrimido[5,4-b][1,4]diazepin-6(5H)-one | MS (ESI) m/z 400 (M + H)$^+$. |
| I-31 | 10-cyclopentyl-5-methyl-2-(1-methylpiperidin-4-ylamino)-6a,7,8,9,9a,10-hexahydrocyclopenta[e]pyrimido[5,4-b][1,4]diazepin-6(5H)-one | MS (ESI) m/z 399 (M + H)$^+$. |
| I-32 | 4-(10-cyclopentyl-5-methyl-6-oxo-5,6,6a,7,8,9,9a,10-octahydrocyclopenta[e]pyrimido[5,4-b][1,4]diazepin-2-ylamino)-N-(2-hydroxyethyl)-3-methoxybenzamide | MS (ESI) m/z 495 (M + H)$^+$. |
| I-33 | 10-cyclopentyl-2-(4-(4-hydroxypiperidin-1-yl)-2-methoxyphenylamino)-5-methyl-6a,7,8,9,9a,10-hexahydrocyclopenta[e]pyrimido[5,4-b][1,4]diazepin-6(5H)-one | MS (ESI) m/z 507 (M + H)$^+$. |

TABLE 1-continued

Compounds of the invention

| Compound ID | Structure | Spectroscopy |
|---|---|---|
| I-34 | 10-cyclopentyl-2-(2-methoxy-4-(4-methylpiperazin-1-yl)phenylamino)-5-methyl-6a,7,8,9,9a,10-hexahydrocyclopenta[e]pyrimido[5,4-b][1,4]diazepin-6(5H)-one | MS (ESI) m/z 506 (M + H)+. |
| I-35 | 4-(10-cyclopentyl-5-methyl-6-oxo-5,6,6a,7,8,9,9a,10-octahydrocyclopenta[e]pyrimido[5,4-b][1,4]diazepin-2-ylamino)-3-methoxy-N-methyl-benzamide | MS (ESI) m/z 465 (M + H)+. |
| I-36 | 10-cyclopentyl-2-(2-methoxy-4-(4-(4-methylpiperazin-1-yl)piperidin-1-yl)phenylamino)-5-methyl-6a,7,8,9,9a,10-hexahydrocyclopenta[e]pyrimido[5,4-b][1,4]diazepin-6(5H)-one | MS (ESI) m/z 589 (M + H)+. |
| I-37 | 6-(10-cyclopentyl-5-methyl-6-oxo-5,6,6a,7,8,9,9a,10-octahydrocyclopenta[e]pyrimido[5,4-b][1,4]diazepin-2-ylamino)-N-methylnicotinamide | MS (ESI) m/z 436 (M + H)+. |

TABLE 1-continued

Compounds of the invention

| Compound ID | Structure | Spectroscopy |
|---|---|---|
| I-38 | 1-(4-(10-cyclopentyl-5-methyl-6-oxo-5,6,6a,7,8,9,9a,10-octahydrocyclopenta[e]pyrimido[5,4-b][1,4]diazepin-2-ylamino)-3-methoxyphenyl)piperidine-4-carboxamide | MS (ESI) m/z 534 (M + H)+ |
| I-39 | 10-cyclopentyl-2-(2-isopropoxy-4-(4-(4-methylpiperazin-1-yl)piperidine-1-carbonyl)phenylamino)-5-methyl-6a,7,8,9,9a,10-hexahydrocyclopenta[e]pyrimido[5,4-b][1,4]diazepin-6(5H)-one | MS (ESI) m/z 645 (M + H)+ |
| I-40 | 6-(10-cyclopentyl-5-methyl-6-oxo-5,6,6a,7,8,9,9a,10-octahydrocyclopenta[e]pyrimido[5,4-b][1,4]diazepin-2-ylamino)-N-(1-methylpiperidin-4-yl)nicotinamide | MS (ESI) m/z 519 (M + H)+ |

TABLE 2

Compounds of the invention

| Compound ID | Structure | Spectroscopy |
|---|---|---|
| II-1 | 2-(2-methoxy-4-(4-methylpiperazin-1-yl)phenylamino)-5-methyl-7a,8,9,10-tetrahydro-5H-pyrimido[5,4-b]pyrrolo[1,2-d][1,4]diazepin-6(7H)-one | MS (ESI) m/z 438 (M + H)+ |
| II-2 | 2-(2-methoxy-4-(4-methylpiperazin-1-yl)phenylamino)-7a,8,9,10-tetrahydro-5H-pyrimido[5,4-b]pyrrolo[1,2-d][1,4]diazepin-6(7H)-one | MS (ESI) m/z 424 (M + H)+ |
| II-3 | 2-(2-methoxy-4-(4-(4-methylpiperazin-1-yl)piperidin-1-yl)phenylamino)-5-methyl-7a,8,9,10-tetrahydro-5H-pyrimido[5,4-b]pyrrolo[1,2-d][1,4]diazepin-6(7H)-one | MS (ESI) m/z 521 (M + H)+ |
| II-4 | 2-(4-(4-hydroxypiperidin-1-yl)-2-isopropoxyphenylamino)-5-methyl-7a,8,9,10-tetrahydro-5H-pyrimido[5,4-b]pyrrolo[1,2-d][1,4]diazepin-6(7H)-one | MS (ESI) m/z 461 (M + H)+ |

TABLE 2-continued

Compounds of the invention

| Compound ID | Structure | Spectroscopy |
|---|---|---|
| II-5 | 2-(5-(4-hydroxypiperidin-1-yl)pyridin-2-ylamino)-5-methyl-7a,8,9,10-tetrahydro-5H-pyrimido[5,4-b]pyrrolo[1,2-d][1,4]diazepin-6(7H)-one | MS (ESI) m/z 410 (M + H)+ |
| II-6 | 2-(2-ethoxy-4-(4-hydroxypiperidin-1-yl)phenylamino)-5-methyl-7a,8,9,10-tetrahydro-5H-pyrimido[5,4-b]pyrrolo[1,2-d][1,4]diazepin-6(7H)-one | MS (ESI) m/z 453 (M + H)+ |
| II-7 | 2-(4-(4-(diethylamino)piperidin-1-yl)-2-isopropoxyphenylamino)-5-methyl-7a,8,9,10-tetrahydro-5H-pyrimido[5,4-b]pyrrolo[1,2-d][1,4]diazepin-6(7H)-one | MS (ESI) m/z 522 (M + H)+ |
| II-8 | 4-(10-cyclopentyl-5-methyl-6-oxo-5,6,6a,7,8,9,9a,10-octahydrocyclopenta[e]pyrimido[5,4-b][1,4]diazepin-2-ylamino)-3-methoxy-N-(1-methylpiperidin-4-yl)benzamide | |

TABLE 2-continued

Compounds of the invention

| Compound ID | Structure | Spectroscopy |
|---|---|---|
| II-9 | 4-(10-cyclopentyl-5-methyl-6-oxo-5,6,6a,7,8,9,9a,10-octahydrocyclo penta[e]pyrimido[5,4-b][1,4]diazepin-2-ylamino)-3-methoxybenzamide | |
| II-10 | 2-(4-(4-(dimethylamino)piperidin-1-yl)-2-isopropoxyphenylamino)-5-methyl-7a,8,9,10-tetrahydro-5H-pyrimido[5,4-b]pyrrolo[1,2-d][1,4]diazepin-6(7H)-one | |

TABLE 3

Compounds of the invention

| Compound ID | Structure | Spectroscopy |
|---|---|---|
| III-1 | 2-(2-methoxy-4-(4-methylpiperazin-1-yl)phenylamino)-5-methyl-9-phenyl-8,9-dihydro-5H-pyrimido[4,5-b][1,4]diazepin-6(7H)-one | MS (ESI) m/z 474 (M + H)$^+$. |

TABLE 3-continued

Compounds of the invention

| Compound ID | Structure | Spectroscopy |
|---|---|---|
| III-2 | 2-(2-methoxy-4-(4-methylpiperazin-1-yl)phenylamino)-9-phenyl-8,9-dihydro-5H-pyrimido[4,5-b][1,4]diazepin-6(7H)-one | MS (ESI) m/z 460 (M + H)$^+$ |
| III-3 | 2-(5-(4-hydroxypiperidin-1-yl)pyridin-2-ylamino)-5-methyl-9-phenyl-8,9-dihydro-5H-pyrimido[4,5-b][1,4]diazepin-6(7H)-one | MS (ESI) m/z 446 (M + H)$^+$ |
| III-4 | 2-(4-(4-hydroxypiperidin-1-yl)-2-isopropoxyphenylamino)-5-methyl-9-phenyl-8,9-dihydro-5H-pyrimido[4,5-b][1,4]diazepin-6(7H)-one | MS (ESI) m/z 503 (M + H)$^+$ |
| III-5 | 2-(2-ethoxy-4-(4-hydroxypiperidin-1-yl)phenylamino)-5-methyl-9-phenyl-8,9-dihydro-5H-pyrimido[4,5-b][1,4]diazepin-6(7H)-one | MS (ESI) m/z 489 (M + H)$^+$ |

TABLE 4

Compounds of the invention

| Compound ID | Structure | Spectroscopy |
|---|---|---|
| IV-1 | 2-(2-methoxy-4-(4-methylpiperazin-1-yl)phenylamino)-5,11-dimethyl-5H-benzo[e]pyrimido[5,4-b][1,4]diazepin-6(11H)-one | MS (ESI) m/z 460 (M + H)+. |
| IV-2 | 2-(2-methoxy-4-(4-methylpiperazin-1-yl)phenylamino)-11-methyl-5H-benzo[e]pyrimido[5,4-b][1,4]diazepin-6(11H)-one | MS (ESI) m/z 446 (M + H)+. |
| IV-3 | 2-(4-(4-hydroxypiperidin-1-yl)-2-isopropoxyphenylamino)-5,11-dimethyl-5H-benzo[e]pyrimido[5,4-b][1,4]diazepin-6(11H)-one | MS (ESI) m/z 489 (M + H)+. |
| IV-4 | 2-(2-methoxy-4-(4-(4-methylpiperazin-1-yl)piperidin-1-yl)phenylamino)-5,11-dimethyl-5H-benzo[e]pyrimido[5,4-b][1,4]diazepin-6(11H)-one | MS (ESI) m/z 543 (M + H)+. |

TABLE 4-continued

Compounds of the invention

| Compound ID | Structure | Spectroscopy |
|---|---|---|
| IV-5 | 2-(5-(4-hydroxypiperidin-1-yl)pyridin-2-ylamino)-5,11-dimethyl-5H-benzo[e]pyrimido[5,4-b][1,4]diazepin-6(11H)-one | MS (ESI) m/z 432 (M + H)$^+$. |
| IV-6 | 2-(2-ethoxy-4-(4-hydroxypiperidin-1-yl)phenylamino)-5,11-dimethyl-5H-benzo[e]pyrimido[5,4-b][1,4]diazepin-6(11H)-one | MS (ESI) m/z 475 (M + H)$^+$. |
| IV-7 | 2-(4-(4-hydroxypiperidin-1-yl)-2-methoxyphenylamino)-5,11-dimethyl-5H-benzo[e]pyrimido[5,4-b][1,4]diazepin-6(11H)-one | MS (ESI) m/z 461 (M + H)$^+$. |
| IV-8 | 5-ethyl-2-(5-(4-hydroxypiperidin-1-yl)pyridin-2-ylamino)-11-methyl-5H-benzo[e]pyrimido[5,4-b][1,4]diazepin-6(11H)-one | MS (ESI) m/z 446 (M + H)$^+$. |

TABLE 4-continued

Compounds of the invention

| Compound ID | Structure | Spectroscopy |
|---|---|---|
| IV-9 | 5-ethyl-2-(4-(4-hydroxypiperidin-1-yl)-2-methoxyphenylamino)-11-methyl-5H-benzo[e]pyrimido[5,4-b][1,4]diazepin-6(11H)-one | MS (ESI) m/z 475 (M + H)$^+$. |
| IV-10 | 2-(2-ethoxy-4-(4-methylpiperazin-1-yl)phenylamino)-11-methyl-5H-benzo[e]pyrimido[5,4-b][1,4]diazepin-6(11H)-one | MS (ESI) m/z 460 (M + H)$^+$. |
| IV-11 | 2-(2-isopropoxy-4-(4-methylpiperazin-1-yl)phenylamino)-11-methyl-5H-benzo[e]pyrimido[5,4-b][1,4]diazepin-6(11H)-one | MS (ESI) m/z 474 (M + H)$^+$. |
| IV-12 | 11-ethyl-2-(2-methoxy-4-(4-methylpiperazin-1-yl)phenylamino)-5-methyl-5H-benzo[e]pyrimido[5,4-b][1,4]diazepin-6(11H)-one | MS (ESI) m/z 474 (M + H)$^+$. |

TABLE 4-continued

Compounds of the invention

| Compound ID | Structure | Spectroscopy |
|---|---|---|
| IV-13 | 11-ethyl-2-(2-methoxy-4-(4-methyl piperazin-1-yl)phenylamino)-5H-benzo[e]pyrimido[5,4-b][1,4]diazepin-6(11H)-one | MS (ESI) m/z 460 (M + H)+. |
| IV-14 | 2-(2-methoxy-4-(4-methylpiperazin-1-yl)phenylamino)-4,5,11-trimethyl-5H-benzo[e]pyrimido[5,4-b][1,4]diazepin-6(11H)-one | MS (ESI) m/z 474 (M + H)+. |
| IV-15 | 2-(2-methoxy-4-(4-methylpiperazin-1-yl)phenylamino)-4,11-dimethyl-5H-benzo[e]pyrimido[5,4-b][1,4]diazepin-6(11H)-one | MS (ESI) m/z 460 (M + H)+. |
| IV-16 | 11-isopropyl-2-(2-methoxy-4-(4-methylpiperazin-1-yl)phenylamino)-5H-benzo[e]pyrimido[5,4-b][1,4]diazepin-6(11H)-one | MS (ESI) m/z 474 (M + H)+. |

TABLE 4-continued

Compounds of the invention

| Compound ID | Structure | Spectroscopy |
|---|---|---|
| IV-17 | 11-isopropyl-2-(2-methoxy-4-(4-methylpiperazin-1-yl)phenylamino)-5-methyl-5H-benzo[e]pyrimido[5,4-b][1,4]diazepin-6(11H)-one | MS (ESI) m/z 488 (M + H)+. |
| IV-18 | 11-cyclopentyl-2-(2-methoxy-4-(4-methylpiperazin-1-yl)phenylamino)-5-methyl-5H-benzo[e]pyrimido[5,4-b][1,4]diazepin-6(11H)-one | MS (ESI) m/z 514 (M + H)+. |
| IV-19 | 11-cyclopentyl-2-(2-methoxy-4-(4-methylpiperazin-1-yl)phenylamino)-5H-benzo[e]pyrimido[5,4-b][1,4]diazepin-6(11H)-one | MS (ESI) m/z 500 (M + H)+. |
| IV-20 | 9-flouro-2-(2-methoxy-4-(4-methylpiperazin-1-yl)phenylamino)-5,11-dimethyl-5H-benzo[e]pyrimido[5,4-b][1,4]diazepin-6(11H)-one | MS (ESI) m/z 478 (M + H)+. |

TABLE 4-continued

Compounds of the invention

| Compound ID | Structure | Spectroscopy |
|---|---|---|
| IV-21 | 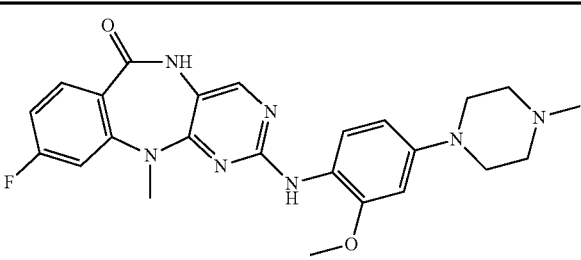<br>9-fluoro-2-(2-methoxy-4-(4-methylpiperazin-1-yl)phenylamino)-11-methyl-5H-benzo[e]pyrimido[5,4-b][1,4]diazepin-6(11H)-one | MS (ESI) m/z 464 (M + H)+. |
| IV-22 | 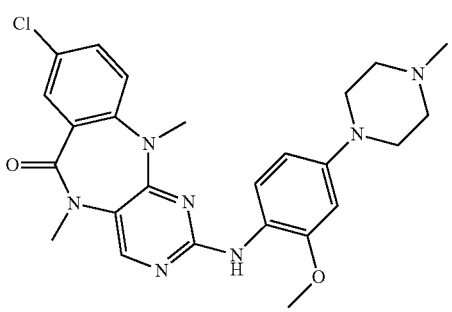<br>8-chloro-2-(2-methoxy-4-(4-methylpiperazin-1-yl)phenylamino)-5,11-dimethyl-5H-benzo[e]primido[5,4][1,4]diazepin-6(11H)-one | MS (ESI) m/z 495 (M + H)+. |
| IV-23 | 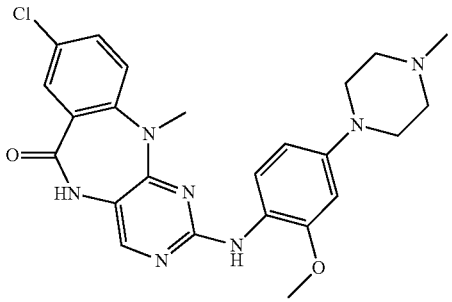<br>8-chloro-2-(2-methoxy-4-(4-methyl piperazin-1-yl)phenylamino)-11-methyl-5H-benzo[e]pyrimido[5,4-b][1,4]diazepin-6(11H)-one | MS (ESI) m/z 481 (M + H)+. |
| IV-24 | 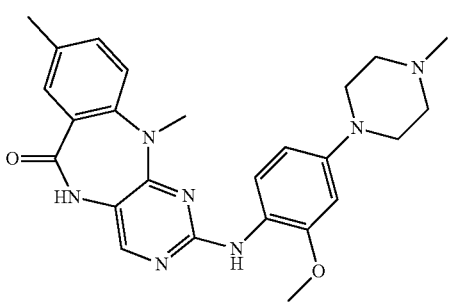<br>2-(2-methoxy-4-(4-methylpiperazin-1-yl)phenylamino)-8,11-dimethyl-5H-benzo[e]pyrimido[5,4-b][1,4]diazepin-6(11H)-one | MS (ESI) m/z 460 (M + H)+. |

TABLE 4-continued

Compounds of the invention

| Compound ID | Structure | Spectroscopy |
|---|---|---|
| IV-25 | 2-(2-methoxy-4-(4-methylpiperazin-1-yl)phenylamino)-5,8,11-trimethyl-5H-benzo[e]pyrimido[5,4-b][1,4]diazepin-6(11H)-one | MS (ESI) m/z 474 (M + H)+. |
| IV-26 | 2-(2-methoxy-4-(4-methylpiperazin-1-yl)phenylamino)-5,11-dimethyl-5H-pyrido[3,4-e]pyrimido[5,4-b][1,4]diazepin-6(11H)-one | MS (ESI) m/z 461 (M + H)+. |
| IV-27 | 2-(2-methoxy-4-(4-methylpiperazin-1-yl)phenylamino)-11-methyl-5H-pyrido[3,4-e]pyrimido[5,4-b][1,4]diazepin-6(11H)-one | MS (ESI) m/z 447 (M + H)+. |
| IV-28 | methyl 4-(5,11-dimethyl-6-oxo-6,11-dihydro-5H-benzo[e]pyrimido[5,4-b][1,4]diazepin-2-ylamino)-3-methoxybenzoate | MS (ESI) m/z 420 (M + H)+. |

TABLE 4-continued

Compounds of the invention

| Compound ID | Structure | Spectroscopy |
|---|---|---|
| IV-29 | 2-(2-methoxy-4-(4-methylpiperazine-1-carbonyl)phenylamino)-5,11-dimethyl-5H-benzo[e]pyrimido[5,4-b][1,4]diazepin-6(11H)-one | MS (ESI) m/z 488 (M + H)+. |
| IV-30 | 4-(5,11-dimethyl-6-oxo-6,11-dihydro-5H-benzo[e]pyrimido[5,4-b][1,4]diazepin-2-ylamino)-N-(2-(dimethylamino)ethyl)-3-methoxybenzamide | MS (ESI) m/z 476 (M + H)+. |
| IV-31 | 9-chloro-2-(2-methoxy-4-(4-methylpiperazin-1-yl)phenylamino)-5,11-dimethyl-5H-benzo[e]pyrimido[5,4][1,4]diazepin-6(1H)-one | MS (ESI) m/z 494 (M + H)+ |
| IV-32 | 11-benzyl-2-(2-methoxy-4-(4-methylpiperazin-1-yl)phenylamino)-5-methyl-5H-benzo[e]pyrimido[5,4-b][1,4]diazepin-6(11H)-one | MS (ESI) m/z 536 (M + H)+ |

TABLE 4-continued

Compounds of the invention

| Compound ID | Structure | Spectroscopy |
|---|---|---|
| IV-33 | 11-benzyl-2-(2-methoxy-4-(4-methylpiperazin-1-yl)phenylamino)-5H-benzo[e]pyrimido[5,4-b][1,4]diazepin-6(11H)-one | MS (ESI) m/z 522 (M + H)$^+$ |
| IV-34 | 4-(5,11-dimethyl-6-oxo-6,11-dihydro-5H-benzo[e]pyrimido[5,4-b][1,4]diazepin-2-ylamino)-3-methoxybenzoic acid | MS (ESI) m/z 406 (M + H)$^+$ |
| IV-35 | methyl 4-(5,11-dimethyl-6-oxo-6,11-dihydro-5H-benzo[e]pyrimido[5,4-b][1,4]diazepin-2-ylamino)-3-methoxybenzoate | MS (ESI) m/z 420 (M + H)$^+$ |
| IV-36 | 3-(5,11-dimethyl-6-oxo-6,11-dihydro-5H-benzo[e]pyrimido[5,4-b][1,4]diazepin-2-ylamino)-4-methoxybenzoic acid | MS (ESI) m/z 406 (M + H)$^+$ |

TABLE 4-continued

Compounds of the invention

| Compound ID | Structure | Spectroscopy |
|---|---|---|
| IV-37 | 2-(2-methoxy-4-(4-(pyrrolidin-1-yl)piperidin-1-carbonyl)phenylamino)-5,11-dimethyl-5H-benzo[e]pyrimido[5,4-b][1,4]diazepin-6(11H)-one | MS (ESI) m/z 542 (M + H)⁺ |
| IV-38 | 2-(2-methoxy-4-(4-(4-methylpiperazin-1-yl)piperidine-1-carbonyl)phenylamino)-5,11-dimethyl-5H-benzo[e]pyrimido[5,4-b][1,4]diazepin-6(11H)-one | MS (ESI) m/z 571 (M + H)⁺ |
| IV-39 | 2-(4-(3-(dimethylamino)pyrrolidine-1-carbonyl)-2-methoxyphenylamino)-5,11-dimethyl-5H-benzo[e]pyrimido[5,4-b][1,4]diazepin-6(11H)-one | MS (ESI) m/z 502 (M + H)⁺ |
| IV-40 | 4-(5,11-dimethyl-6-oxo-6,11-dihydro-5H-benzo[e]pyrimido[5,4-b][1,4]diazepin-2-ylamino)-3-methoxy-N-(1-methylpiperidin-4-yl)benzamide | MS (ESI) m/z 502 (M + H)⁺ |

TABLE 4-continued

Compounds of the invention

| Compound ID | Structure | Spectroscopy |
|---|---|---|
| IV-41 | 3-(5,11-dimethyl-6-oxo-6,11-dihydro-5H-benzo[e]pyrimido[5,4-b][1,4]diazepin-2-ylamino)-4-methoxy-N-(1-methylpiperidin-4-yl)benzamide | MS (ESI) m/z 502 (M + H)+ |
| IV-42 | 2-(2-methoxy-5-(4-(4-methylpiperazin-1-yl)piperidine-1-carbonyl)phenylamino)-5,11-dimethyl-5H-benzo[e]pyrimido[5,4-b][1,4]diazepin-6(11H)-one | MS (ESI) m/z 571 (M + H)+ |
| IV-43 | 2-(5-(3-(dimethylamino)pyrrolidine-1-carbonyl)-2-methoxyphenylamino)-5,11-dimethyl-5H-benzo[e]pyrimido[5,4-b][1,4]diazepin-6(11H)-one | MS (ESI) m/z 502 (M + H)+ |

TABLE 4-continued

Compounds of the invention

| Compound ID | Structure | Spectroscopy |
|---|---|---|
| IV-44 | 3-(5,11-dimethyl-6-oxo-6,11-dihydro-5H-benzo[e]pyrimido[5,4-b][1,4]diazepin-2-ylamino)-N-(2-(dimethylamino)ethyl)-4-methoxybenzamide | MS (ESI) m/z 476 (M + H)+ |
| IV-45 | 2-(4-(4-(2-hydroxyethyl)piperazine-1-carbonyl)-2-methoxyphenylamino)-5,11-dimethyl-5H-benzo[e]pyrimido[5,4-b][1,4]diazepin-6(11H)-one | MS (ESI) m/z 518 (M + H)+ |
| IV-46 | 2-(2-methoxy-4-(4-methylpiperazin-1-yl)phenylamino)-5-methyl-5H-benzo[e]pyrimido[5,4-b][1,4]diazepin-6(11H)-one | MS (ESI) m/z 446 (M + H)+ |
| IV-47 | 2-(2-methoxy-4-(4-methylpiperazin-1-yl)phenylamino)-5H-benzo[e]pyrimido[5,4-b][1,4]diazepin-6(11H)-one | MS (ESI) m/z 432 (M + H)+ |

TABLE 4-continued

Compounds of the invention

| Compound ID | Structure | Spectroscopy |
|---|---|---|
| IV-II-1 | 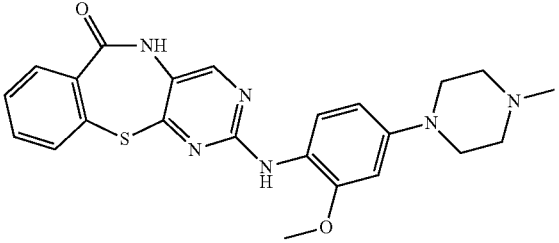<br>2-(2-methoxy-4-(4-methylpiperazin-1-yl)phenylamino)-5-methylbenzo[f]pyrimido[4,5-b][1,4]thiazepin-6(5H)-one | $^{1}$H NMR (600 MHz, CDCl$_3$) δ 8.32 (s, 1H), 8.18 (d, J = 8.4 Hz, 1H), 7.80 (dd, J = 1.8, 7.8 Hz, 1H), 7.61 (s, 1H), 7.51 (dd, J = 1.8, 7.8 Hz, 1H), 7.40-7.34 (m, 2H), 6.54 (dd, J = 1.8, 8.4 Hz, 1H), 6.52 (d, J = 1.8 Hz, 1H), 3.85 (s, 3H), 3.55 (s, 3H), 3.23 (s, br, 4H), 2.69 (s, br, 4H), 2.43 (s, 3H).<br>MS (ESI) m/z 463 (M + H)$^{+}$ |
| IV-II-2 | 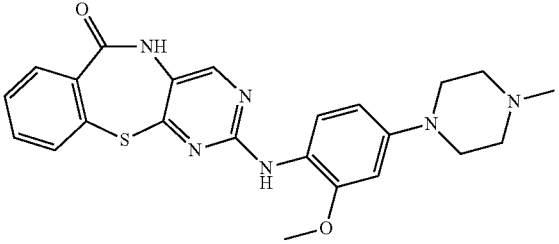<br>2-(2-methoxy-4-(4-methylpiperazin-1-yl)phenylamino)benzo[f]pyrimido[4,5-b][1,4]thiazepin-6(5H)-one | MS (ESI) m/z 449 (M + H)$^{+}$ |
| IV-II-3 | 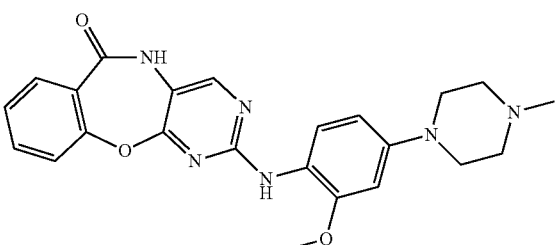<br>2-(2-methoxy-4-(4-methylpiperazin-1-yl)phenylamino)benzo[f]pyrimido[4,5-b][1,4]oxazepin-6(5H)-one | MS (ESI) m/z 433 (M + H)$^{+}$ |
| IV-II-4 | 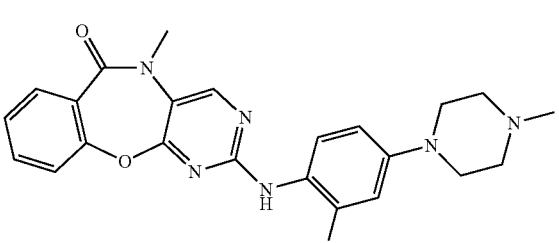<br>2-(2-methoxy-4-(4-methylpiperazin-1-yl)phenylamino)-5-methylbenzo[f]pyrimido[4,5-b][1,4]oxazepin-6(5H)-one | MS (ESI) m/z 447 (M + H)$^{+}$ |

TABLE 4-continued

Compounds of the invention

| Compound ID | Structure | Spectroscopy |
|---|---|---|
| VII-1 | 2-(2-methoxy-4-(4-methylpiperazin-1-yl)phenylamino)-5-methyl-9-phenyl-5H-pyrimido[5,4-e][1,4]diazepin-6(7H)-one | |
| VII-2 | 3-methoxy-4-(5-methyl-6-oxo-9-phenyl-6,7-dihydro-5H-pyrimido[5,4-e][1,4]diazepin-2-ylamino)-N-(1-methylpiperidin-4-yl)benzamide | |
| VII-3 | 4-(9-cyclopentyl-7-ethyl-5-methyl-6-oxo-6,7-dihydro-5H-pyrimido[5,4-e][1,4]diazepin-2-ylamino)-3-hydroxy-N-(1-methylpiperidin-4-yl)benzamide | |
| VII-4 | 4-(7-ethyl-5-methyl-6-oxo-9-phenyl-6,7-dihydro-5H-pyrimido[5,4-e][1,4]diazepin-2-ylamino)-3-methoxy-N-(1-methylpiperidin-4-yl)benzamide | |

TABLE 4-continued
Compounds of the invention
| Compound ID | Structure | Spectroscopy |
|---|---|---|
| VII-5 | 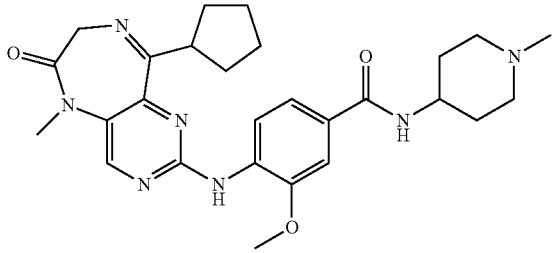 [SMILES: COc1cc(C(=O)NC2CCN(C)CC2)ccc1Nc1ncc2c(n1)N(C1CCCC1)CCC(=O)N2C]<br>4-(9-cyclopentyl-5-methyl-6-oxo-6,7-dihydro-5H-pyrimido[5,4-e][1,4]diazepin-2-ylamino)-3-methoxy-N-(1-methylpiperidin-4-yl)benzamide | |
TABLE 5
Compounds of the Invention
| Compound ID | Structure | Spectroscopy |
|---|---|---|
| V-1 | 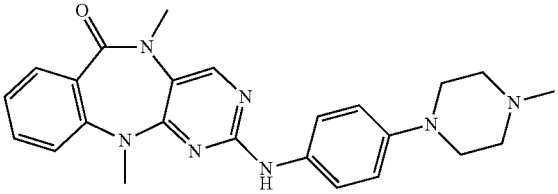 [SMILES: CN1CCN(c2ccc(Nc3ncc4c(n3)N(C)c3ccccc3C(=O)N4C)cc2)CC1] | MS (ESI) m/z 430 (M + H)+ |
| V-2 | 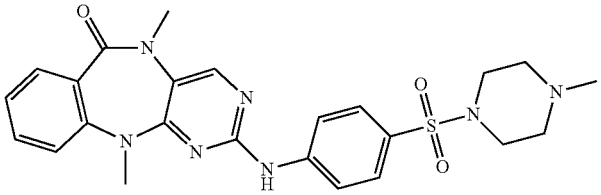 [SMILES: CN1CCN(S(=O)(=O)c2ccc(Nc3ncc4c(n3)N(C)c3ccccc3C(=O)N4C)cc2)CC1] | MS (ESI) m/z 494 (M + H)+ |
| V-3 | 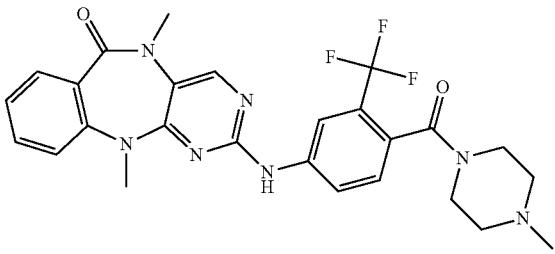 [SMILES: CN1CCN(C(=O)c2ccc(Nc3ncc4c(n3)N(C)c3ccccc3C(=O)N4C)cc2C(F)(F)F)CC1] | MS (ESI) m/z 526 (M + H)+ |
| V-4 | 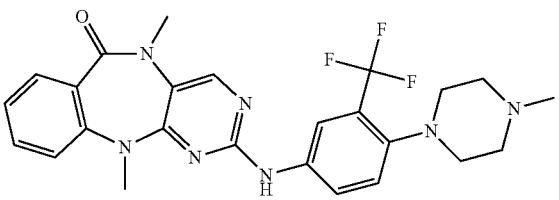 [SMILES: CN1CCN(c2ccc(Nc3ncc4c(n3)N(C)c3ccccc3C(=O)N4C)cc2C(F)(F)F)CC1] | MS (ESI) m/z 498 (M + H)+ |

TABLE 5-continued

Compounds of the Invention

| Compound ID | Structure | Spectroscopy |
|---|---|---|
| V-5 | 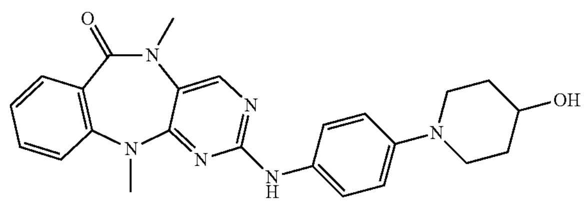 [SMILES: CN1C(=O)c2ccccc2N(C)c2nc(Nc3ccc(N4CCC(O)CC4)cc3)ncc21] | MS (ESI) m/z 431 (M + H)+ |
| V-6 | 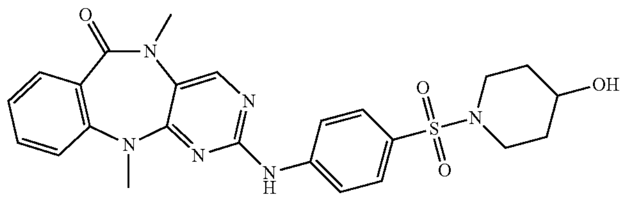 [SMILES: CN1C(=O)c2ccccc2N(C)c2nc(Nc3ccc(S(=O)(=O)N4CCC(O)CC4)cc3)ncc21] | MS (ESI) m/z 495 (M + H)+ |
| V-7 | 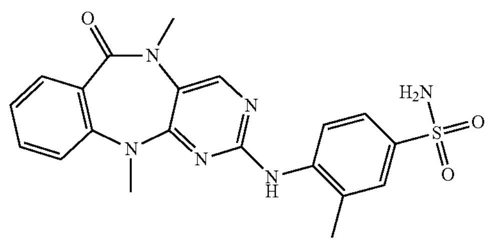 [SMILES: Cc1cc(S(N)(=O)=O)ccc1Nc1ncc2c(n1)N(C)c1ccccc1C(=O)N2C] | MS (ESI) m/z 425 (M + H)+ |
| V-8 | 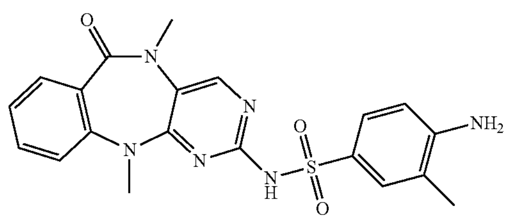 [SMILES: Cc1cc(S(=O)(=O)Nc2ncc3c(n2)N(C)c2ccccc2C(=O)N3C)ccc1N] | MS (ESI) m/z 425 (M + H)+ |
| V-9 | 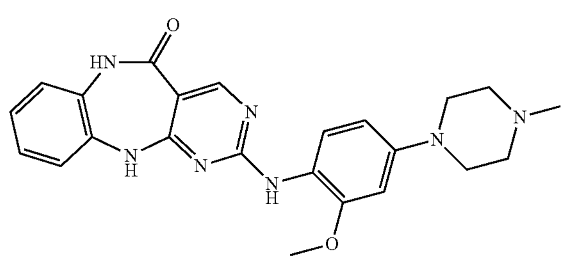 [SMILES: COc1cc(N2CCN(C)CC2)ccc1Nc1ncc2c(n1)Nc1ccccc1NC2=O] | MS (ESI) m/z 432 (M + H)+ |
| V-10 | 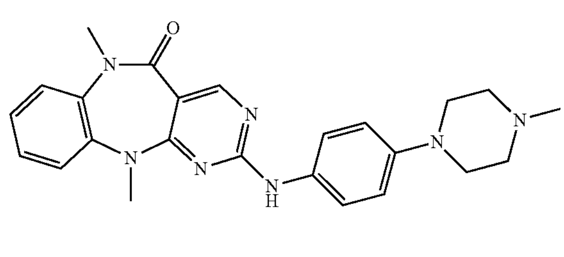 [SMILES: CN1CCN(c2ccc(Nc3ncc4c(n3)N(C)c3ccccc3N(C)C4=O)cc2)CC1] | MS (ESI) m/z 430 (M + H)+ |

TABLE 5-continued

Compounds of the Invention

| Compound ID | Structure | Spectroscopy |
|---|---|---|
| V-11 | 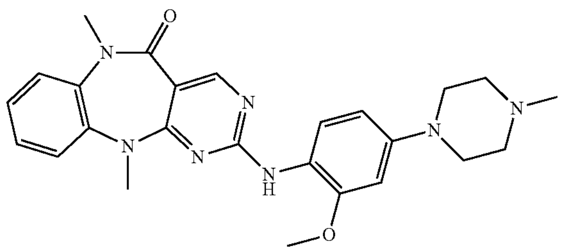 [SMILES: COc1cc(N2CCN(C)CC2)ccc1Nc1ncc2c(n1)N(C)c1ccccc1N(C)C2=O] | MS (ESI) m/z 460 (M + H)+ |
| V-12 | 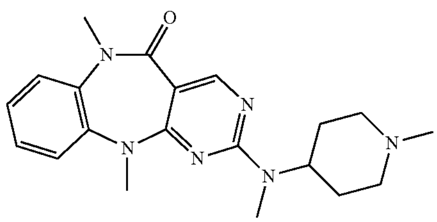 [SMILES: CN1CCC(N(C)c2ncc3c(n2)N(C)c2ccccc2N(C)C3=O)CC1] | MS (ESI) m/z 367 (M + H)+ |
| V-13 | 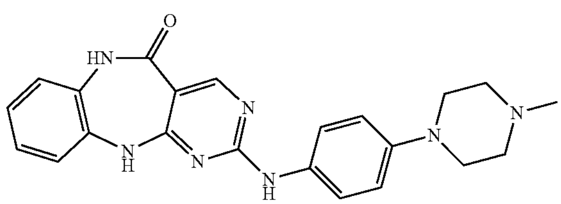 [SMILES: CN1CCN(c2ccc(Nc3ncc4c(n3)Nc3ccccc3NC4=O)cc2)CC1] | MS (ESI) m/z 402 (M + H)+ |
| V-14 | 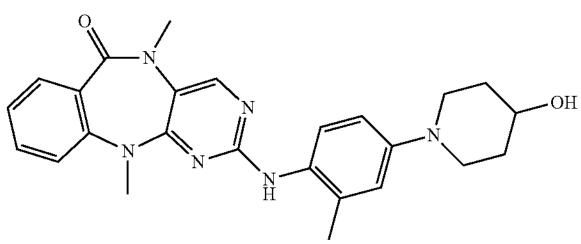 [SMILES: Cc1cc(N2CCC(O)CC2)ccc1Nc1ncc2c(n1)N(C)c1ccccc1C(=O)N2C] | MS (ESI) m/z 445 (M + H)+ |
| V-15 | 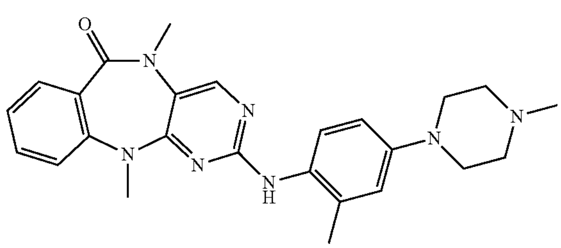 [SMILES: Cc1cc(N2CCN(C)CC2)ccc1Nc1ncc2c(n1)N(C)c1ccccc1C(=O)N2C] | MS (ESI) m/z 444 (M + H)+ |
| V-16 | 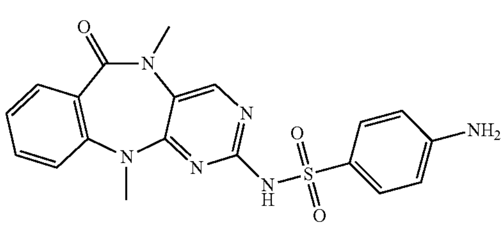 [SMILES: CN1C(=O)c2ccccc2N(C)c2nc(NS(=O)(=O)c3ccc(N)cc3)ncc21] | MS (ESI) m/z 411 (M + H)+ |

TABLE 5-continued

Compounds of the Invention

| Compound ID | Structure | Spectroscopy |
|---|---|---|
| V-17 | 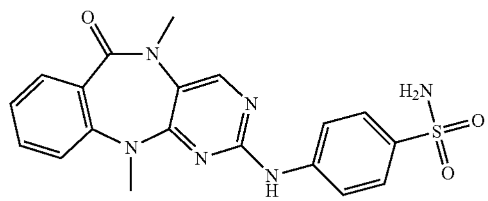 [SMILES: CN1C(=O)c2ccccc2N(C)c2nc(Nc3ccc(S(N)(=O)=O)cc3)ncc21] | MS (ESI) m/z 411 (M + H)+ |
| V-18 | 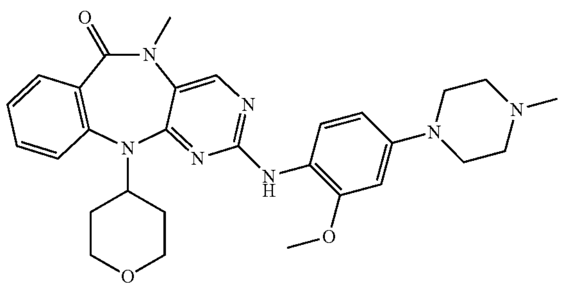 [SMILES: COc1cc(N2CCN(C)CC2)ccc1Nc1ncc2c(n1)N(C1CCOCC1)c1ccccc1C(=O)N2C] | MS (ESI) m/z 530 (M + H)+ |
| V-19 | 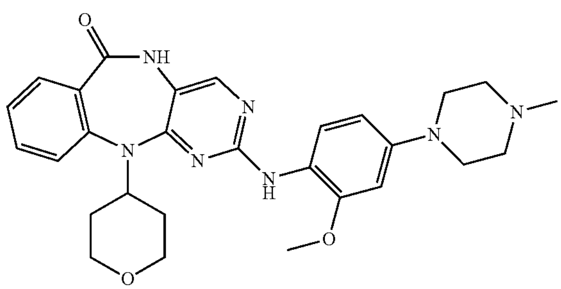 | MS (ESI) m/z 526 (M + H)+ |
| V-20 | 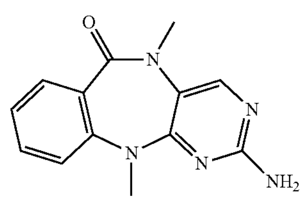 [SMILES: CN1C(=O)c2ccccc2N(C)c2nc(N)ncc21] | MS (ESI) m/z 256 (M + H)+ |
| V-21 | 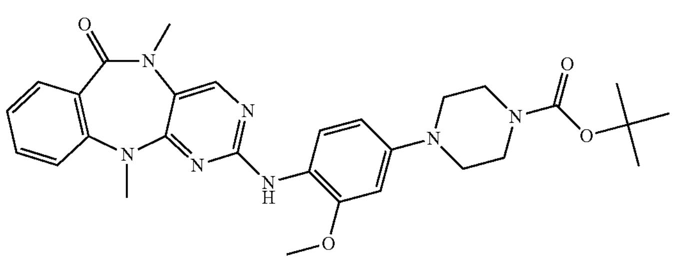 [SMILES: COc1cc(N2CCN(C(=O)OC(C)(C)C)CC2)ccc1Nc1ncc2c(n1)N(C)c1ccccc1C(=O)N2C] | MS (ESI) m/z 546 (M + H)+ |
| V-22 | 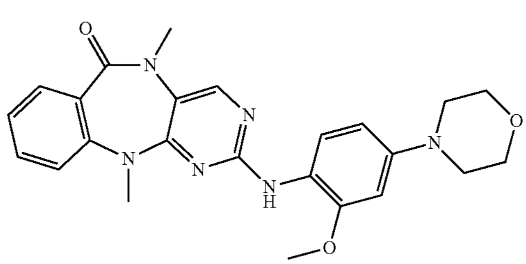 [SMILES: COc1cc(N2CCOCC2)ccc1Nc1ncc2c(n1)N(C)c1ccccc1C(=O)N2C] | MS (ESI) m/z 447 (M + H)+ |

TABLE 5-continued

Compounds of the Invention

| Compound ID | Structure | Spectroscopy |
|---|---|---|
| V-23 | 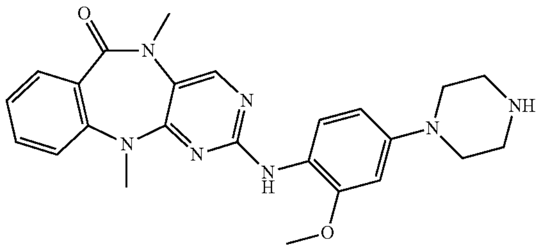 [SMILES: COc1cc(N2CCNCC2)ccc1Nc1ncc2c(n1)N(C)c1ccccc1C(=O)N2C] | MS (ESI) m/z 446 (M + H)+ |
| V-24 | 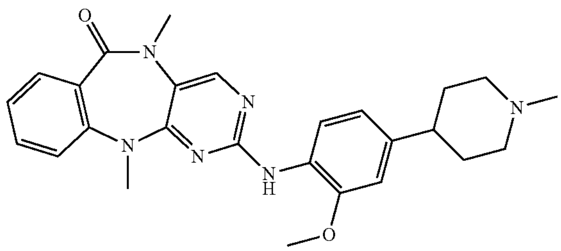 [SMILES: COc1cc(C2CCN(C)CC2)ccc1Nc1ncc2c(n1)N(C)c1ccccc1C(=O)N2C] | MS (ESI) m/z 459 (M + H)+ |
| V-25 | 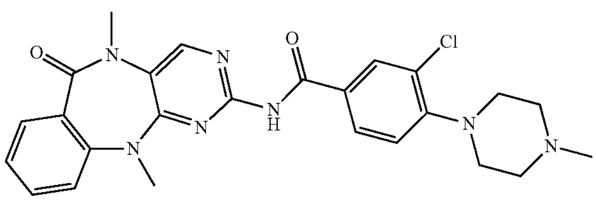 [SMILES: CN1CCN(c2ccc(C(=O)Nc3ncc4c(n3)N(C)c3ccccc3C(=O)N4C)cc2Cl)CC1] | MS (ESI) m/z 492 (M + H)+ |
| V-26 | 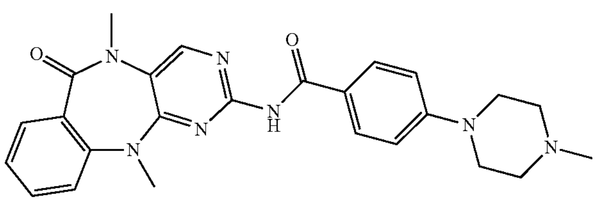 [SMILES: CN1CCN(c2ccc(C(=O)Nc3ncc4c(n3)N(C)c3ccccc3C(=O)N4C)cc2)CC1] | MS (ESI) m/z 458 (M + H)+ |
| V-27 | 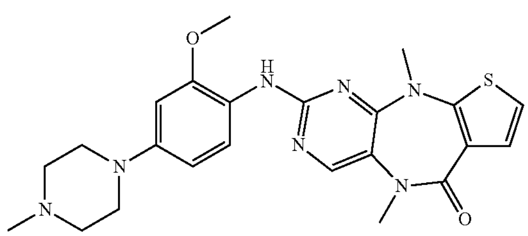 [SMILES: COc1cc(N2CCN(C)CC2)ccc1Nc1ncc2c(n1)N(C)c1sccc1C(=O)N2C] | $^1$H NMR (600 MHz, CDCl$_3$) δ 8.08 (s, 1H), 7.74 (d, J = 9.0 Hz, 1H), 7.20 (d, J = 5.4 Hz, 1H), 7.00 (d, J = 5.4 Hz, 1H), 6.76 (d, J = 2.4 Hz, 1H), 6.66 (dd, J = 9.0, 2.4 Hz, 1H), 3.90 (s, 3H), 3.88-3.85 (m, 2H), 3.64-3.60 (m, 2H), 3.51 (s, 3H), 3.36 (s, 3H), 3.28-3.26 (m, 2H), 3.12-3.06 (m, 2H), 2.98 (s, 3H). MS (ESI) m/z 466 (M + H)+ |
| V-28 | 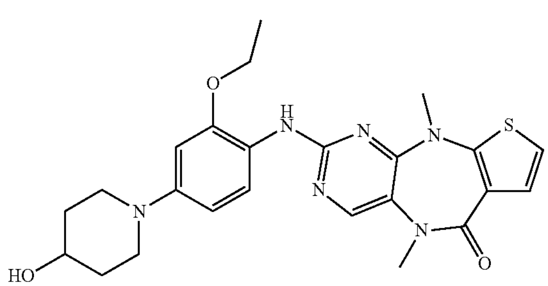 [SMILES: CCOc1cc(N2CCC(O)CC2)ccc1Nc1ncc2c(n1)N(C)c1sccc1C(=O)N2C] | MS (ESI) m/z 481 (M + H)+ |

Example 7

Mps1 (TTK) Cellular Assay—Mitotic Escape Assay

Hela (or U2OS cells) were plated at roughly 30-35% cell density. After 24 hours the medium* was removed and fresh medium supplemented with 2.5 mM thymidine was added to arrest cells at the G1/S transition. After 24 hours in thymidine block the medium was removed, the cells were washed 3× with PBS and replaced with medium supplemented with 330 nM nocodazole (Noc). The cells were incubated with nocodazole for 16-18 hours to produce a mitotic arrest. The medium was then removed carefully and replaced with medium supplemented with 330 nM nocodazole and test compound at the desired concentration (with the final concentration of DMSO below 0.2%). After 2 hours, the cells were harvested, lysed in RIPA buffer, and the levels of cyclin B or phosphorylated Histone 3 (Ser10) determined by western blotting. Alternatively, cells were treated on coverslips, fixed, and phosphorylated Histone 3 levels determined by immunofluorescence. See FIG. 1.

*Hela/U2OS medium—Dulbecco's Modified Eagle's Medium (DMEM, Sigma), 10% fetal bovine serum, 1% penicillin/streptomycin

Example 8

Plk1 Cellular Assay—Mitotic Arrest Assay

Figure 2:
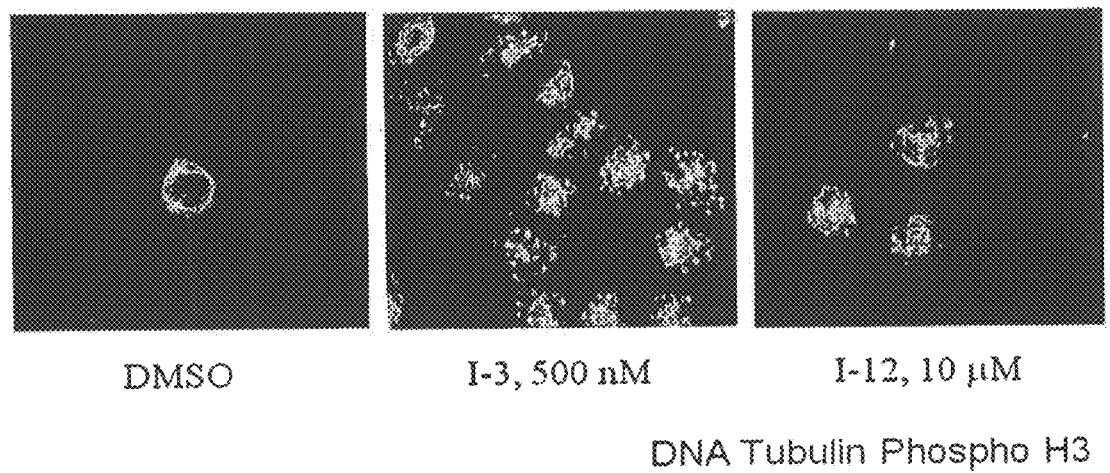
FIG. 2. Plk1 inhibitors I-3 and I-12 induce mitotic arrest. Using immunofluorescence microscopy the cells were located by their DNA stain (Hoechst) and were then scored for phospho H3 positivity. Cells that are arrested in mitosis are phospho H3 positive. Chemical inhibition of Plk1 has been shown to cause a mitotic arrest and thus an increase in phospho H3 signal. Compounds were ranked for their Plk1 activity based on the percentage of cells exhibiting a mitotic arrest phenotype as exemplified by high phospho H3 positivity.
Figure 3:
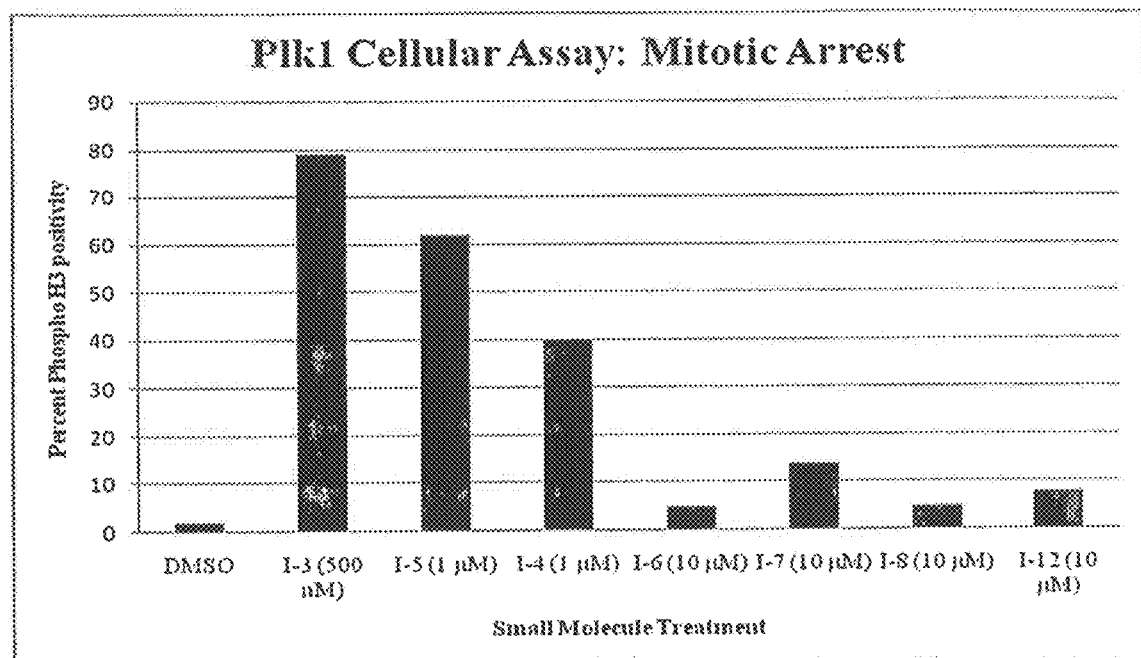
FIG. 3. Compounds I-3, I-4, I-5 induce a strong mitotic arrest while compounds I-6, I-7, I-8, and I-12 do not. Results quantitated from Plk1 Mitotic Arrest assay as described in FIG. 2.

Hela cells were plated at roughly 80% cell density on poly-lysine coated glass coverslips. After 24 hours the medium* was removed and fresh medium supplemented with test compounds was added. Twenty-four hours post-treatment the medium was removed, the coverslips were washed once with phosphate-buffered saline (PBS), pH 7.4 and the cells fixed for 10 minutes at room temperature using the following fixative solution: 100 mM K-Pipes, pH 6.8, 10 mM EGTA, 1 mM $MgCl_2$, 0.2% Triton X-100, 3% formaldehyde. The coverslips were washed 3× with Tris-buffered saline solution (50 mM Tris-HCl pH 7.4, 150 mM NaCl) containing 0.1% Triton X-100 (TBST). The samples were blocked using 2% bovine serum albumin (BSA) in TBST. The samples were then incubated with a phosphorylation-specific antibody against histone 3 (phospho H3) serine-10 (Upstate, 1:500-1:1000) in blocking solution. Cells can also optionally be stained for tubulin as well using appropriate antibodies. After a 2-hr. incubation at room temperature (or 4° C. overnight), the samples were washed 3× with TBST. The samples were then incubated with an appropriate secondary antibody in blocking solution for 1-2 hrs at room temperature (or 4° C. overnight). The samples were washed 3× with TBST and then incubated with Hoechst 33342 stain (Invitrogen, 1:1000-1:2000) in TBST for 15 minutes at room temperature. The samples were washed 3× with TBST and mounted onto glass slides using Prolong Gold Antifade Reagent (Invitrogen). See FIGS. 2 and 3.

*Hela/U2OS medium—Dulbecco's Modified Eagle's Medium (DMEM, Sigma), 10% fetal bovine serum, 1% penicillin/streptomycin

Example 9

Figure 4:
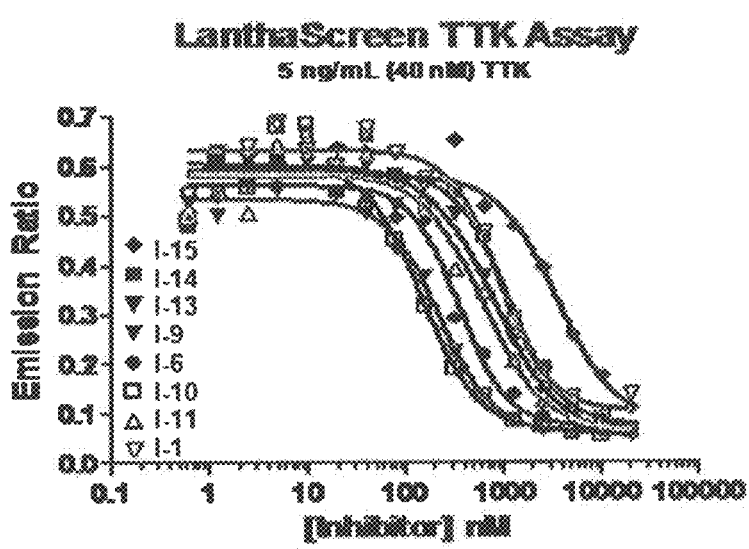
FIG. 4. Dose-response curves for inhibitors in a Mps1 biochemical kinase assay. Results were obtained using Invitrogen's Mps1 (TTK) LanthaScreen Activity Assay.
Figure 5:
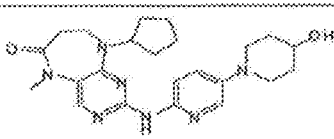
FIG. 5. $IC_{50}$ values for inhibition of Mps1 kinase activity. The $IC_{50}$ values for the compounds shown above were calculated from the raw data in the previous figure. Staurosporine was used as a reference compound ($IC_{50}$ on Mps1 kinase activity=1388 nM).
Figure 5:
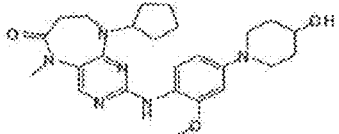
Figure 5:
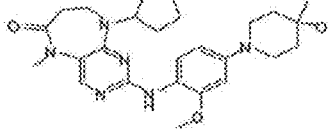
Figure 5:
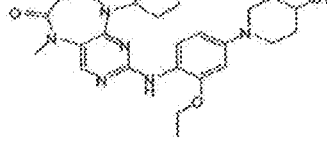
Figure 5:
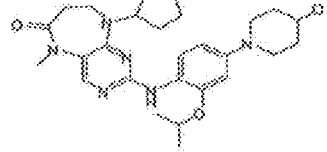
Figure 5:
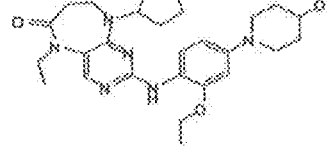
Figure 5:
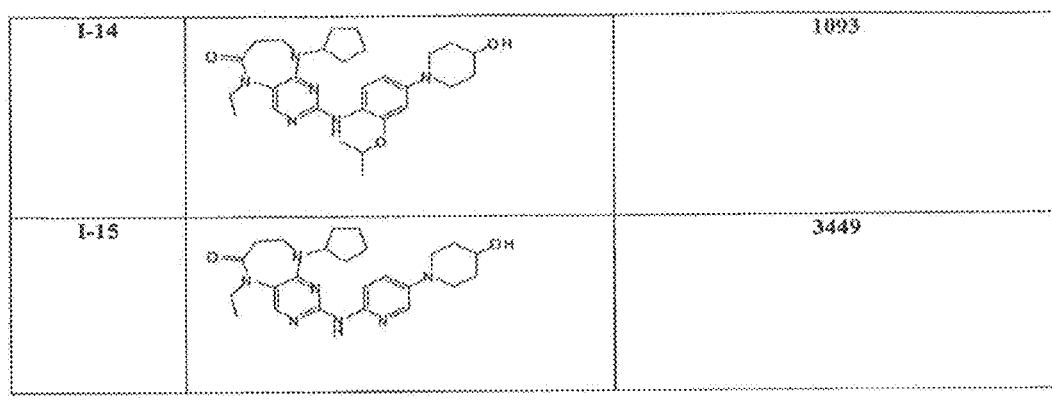
Figure 6:
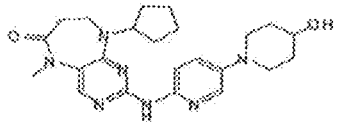
FIG. 6. In vitro Plk1 binding assay: Ambit $K_d$ values in nanomolar. $K_d$ values generated by Ambit binding assay over a concentration range of the compound.
Figure 6:
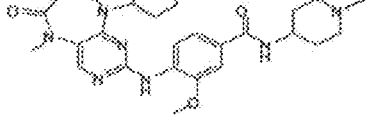
Figure 6:
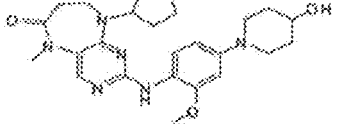
Figure 6:
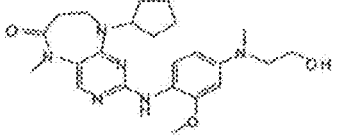
Figure 6:
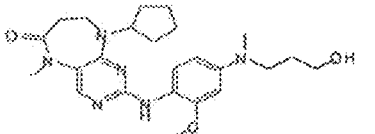
Figure 6:
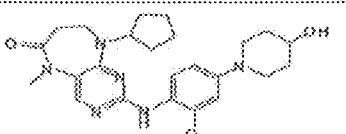
Figure 6:
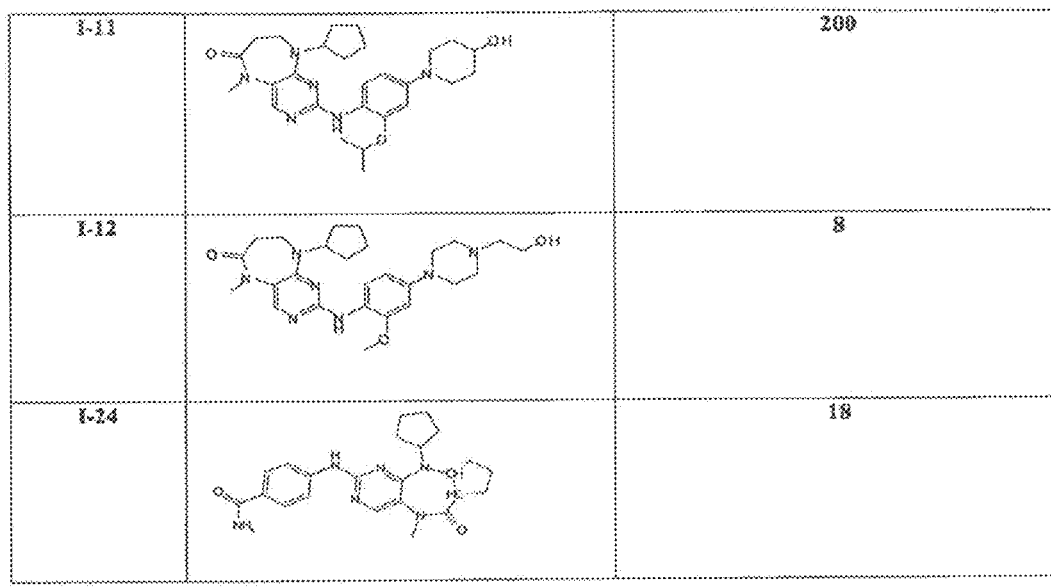
Figure 7:
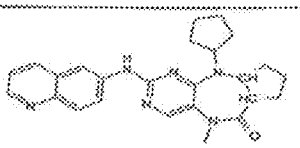
FIG. 7. In vitro Erk5 binding assay: Ambit $K_d$ values in nanomolar. $K_d$ values generated by Ambit binding assay over a concentration range of the compound.
Figure 7:
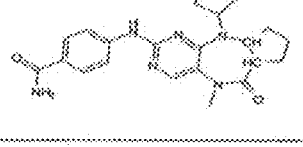
Figure 7:
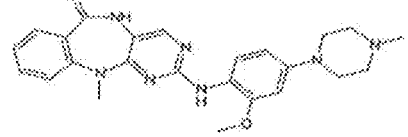
Figure 7:
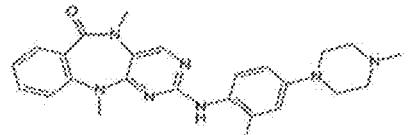
Figure 7:
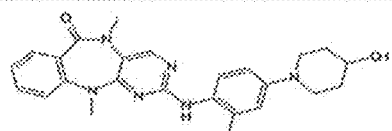
Figure 7:
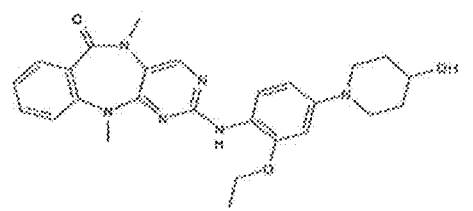
Figure 7:

In Vitro Mps1 Kinase Assay—Invitrogen Mps1 (TTK) LanthaScreen Activity Assay Kinase reactions were carried out at room temperature with the following components: 1× kinase reaction buffer, 5 μg/mL (40 nM) Mps1 kinase, 200 nM AF-647 E4Y substrate, and 1 μM ATP ($K_{m,app}$<1 μM). After one hour a preparation of EDTA (20 mM) and Eu-PY20 Tb-labeled antibody (4 nM) in TR-FRET dilution buffer was added. The final concentration of EDTA and Eu-PY20 in the reaction mixture is 10 mM and 2 nM respectively. The reaction mixture was incubated at room temperature for 30 minutes before being read on a plate reader configured for LanthaScreen™ TR-FRET. Kinase reactions were run over several concentrations of inhibitor to obtain dose-dependent curves as seen in FIGS. 4, 5 and 6.

Incorporation by Reference

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

Equivalents

Those skilled in the art will recognize, or be able to ascertain using no more than routine experimentation, many equivalents of the specific embodiments of the invention described herein. Such equivalents are intended with be encompassed by the following claims.

What is claimed is:
1. A compound of formula (G):

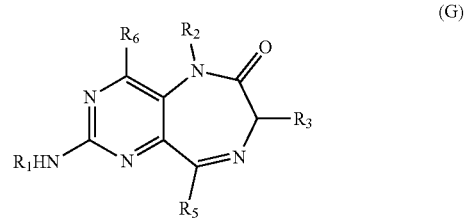

or a pharmaceutically acceptable salt thereof,
wherein,
$R_1$ is alkyl, alkenyl, or alkynyl, or $R_1$ is aryl, arylalkyl, heteroaryl, heterocycloalkyl, or cycloalkyl, wherein $R_1$ is substituted with 0-4 substituents, selected from halo, nitro, cyano, hydroxyl, amino, $NH(R_A)$, $N(R_A)(R_A)$, $CO_2H$, $C(O)R_A$, $C(O)NH_2$, $C(O)NH(R_A)$, $C(O)N(R_A)$$(R_A)$, alkyl, aryl, arylalkyl, alkoxy, heteroaryl, heterocyclic, and carbocyclic, wherein each $R_A$ is independently selected from alkyl, carbocyclic, aryl, heteroaryl, and heterocyclic;
$R_2$ is hydrogen or an optionally substituted alkyl group by replacement of one, two, or three or more of the hydrogen atoms in the alkyl group with a substituent selected from the group consisting of;
F, Cl, Br, I, OH, protected hydroxy, $NO_2$, CN,
$NH_2$, NH—$C_1$-$C_{12}$-alkyl, NH $C_2$-$C_{12}$-alkenyl, NH—$C_2$-$C_{12}$-alkenyl, NH—$C_3$-$C_{12}$-cycloalkyl, NH-aryl, NH-heteroaryl, NH-heterocycloalkyl, -dialkylamino, -diarylamino, -diheteroarylamino,
O—$C_1$-$C_{12}$-alkyl, O—$C_2$-$C_{12}$-alkenyl, O—$C_2$-$C_{12}$-alkenyl, O—$C_3$-$C_{12}$-cycloalkyl, O-aryl, O-heteroaryl, O-heterocycloalkyl, C(O)—C$_1$-C$_{12}$-alkyl, C(O)—C$_2$-C$_{12}$-alkenyl, C(O)—C$_2$-C$_{12}$-alkenyl, C(O)—C$_3$-C$_{12}$-cycloalkyl, C(O)-aryl, C(O)-heteroaryl, C(O)-heterocycloalkyl, CONH$_2$, CONH—C$_1$-C$_{12}$-alkyl, CONH—C$_2$-C$_{12}$-alkenyl, CONH—C$_2$-C$_{12}$-alkenyl, CONH—C$_3$-C$_{12}$-cycloalkyl, CONH-aryl, CONH-heteroaryl, CONH heterocycloalkyl, OCO$_2$—C$_1$-C$_{12}$-alkyl, OCO$_2$—C$_2$-C$_{12}$-alkenyl, OCO$_2$—C$_2$-C$_{12}$-alkenyl, OCO$_2$—C$_3$-C$_{12}$-cycloalkyl, OCO$_2$-aryl, OCO$_2$-heteroaryl, OCO$_2$-heterocycloalkyl, OCONH$_2$, OCONH—C$_1$-C$_{12}$-alkyl, OCONH—C$_2$-C$_{12}$-alkenyl, OCONH—C$_2$-C$_{12}$-alkenyl, OCONH—C$_3$-C$_{12}$-cycloalkyl, OCONH-aryl, OCONH-heteroaryl, OCONH-heterocycloalkyl, NHC(O)—C$_1$-C$_{12}$-alkyl, NHC(O)—C$_2$-C$_{12}$-alkenyl, NHC(O)—C$_2$-C$_{12}$-alkenyl, NHC(O)—C$_3$-C$_{12}$-cycloalkyl, NHC(O)-aryl, NHC(O)-heteroaryl, NHC(O)-heterocycloalkyl, NHCO$_2$—C$_1$-C$_{12}$-alkyl, NHCO$_2$—C$_2$-C$_{12}$-alkenyl, NHCO$_2$—C$_2$-C$_{12}$-alkenyl, NHCO$_2$—C$_3$-C$_{12}$-cycloalkyl, NHCO$_2$-aryl, NHCO$_2$-heteroaryl, NHCO$_2$-heterocycloalkyl, NHC(O)NH$_2$, NHC(O)NH—C$_1$-C$_{12}$-alkyl, NHC(O)NH—C$_2$-C$_{12}$-alkenyl, NHC(O)NH—C$_2$-C$_{12}$-alkenyl, NHC(O)NH—C$_3$-C$_{12}$-cycloalkyl, NHC(O)NH-aryl, NHC(O)NH-heteroaryl, NHC(O)NH-heterocycloalkyl, NHC(S)NH$_2$, NHC(S)NH—C$_1$-C$_{12}$-alkyl, NHC(S)NH—C$_2$-C$_{12}$-alkenyl, NHC(S)NH—C$_2$-C$_{12}$-alkenyl, NHC(S)NH-C$_3$-C$_{12}$-cycloalkyl, NHC(S)NH-aryl, NHC(S)NH-heteroaryl, NHC(S)NH-heterocycloalkyl, NHC(NH)NH$_2$, NHC(NH)NH—C$_1$-C$_{12}$-alkyl, NHC(NH)NH—C$_2$-C$_{12}$-alkenyl, NHC(NH)NH—C$_2$-C$_{12}$-alkenyl, NHC(NH)NH—C$_3$-C$_{12}$-cycloalkyl, NHC(NH)NH-aryl, NHC(NH)NH-heteroaryl, NHC(NH)NH-heterocycloalkyl, NHC(NH)—C$_1$-C$_{12}$-alkyl, NHC(NH)—C$_2$-C$_{12}$-alkenyl, NHC(NH)-C$_2$-C$_{12}$-alkenyl, NHC(NH)—C$_3$-C$_{12}$-cycloalkyl, NHC(NH)-aryl, NHC(NH)-heteroaryl, NHC(NH)-heterocycloalkyl, C(NH)NH—C$_1$-C$_{12}$-alkyl, C(NH)NH—C$_2$-C$_{12}$-alkenyl, C(NH)NH—C$_2$-C$_{12}$-alkenyl, C(NH)NH—C$_3$-C$_{12}$-cycloalkyl, C(NH)NH-aryl, C(NH)NH-heteroaryl, C(NH)NH-heterocycloalkyl, S(O)—C$_1$-C$_{12}$-alkyl, S(O)—C$_2$-C$_{12}$-alkenyl, S(O)—C$_2$-C$_{12}$-alkenyl, S(O)—C$_3$-C$_{12}$-cycloalkyl, S(O)-aryl, S(O)-heteroaryl, S(O)-heterocycloalkyl SO$_2$NH$_2$, SO$_2$NH—C$_1$-C$_{12}$-alkyl, SO$_2$NH—C$_2$-C$_{12}$-alkenyl, —SO$_2$NH—C$_2$-C$_{12}$-alkenyl, SO$_2$NH—C$_3$-C$_{12}$-cycloalkyl, SO$_2$NH-aryl, SO$_2$NH-heteroaryl, SO$_2$NH-heterocycloalkyl, NHSO$_2$—C$_1$-C$_{12}$-alkyl, NHSO$_2$—C$_2$-C$_{12}$-alkenyl, NHSO$_2$—C$_2$-C$_{12}$-alkenyl, NHSO$_2$—C$_3$-C$_{12}$-cycloalkyl, NHSO$_2$-aryl, NHSO$_2$-heteroaryl, NHSO$_2$-heterocycloalkyl, and, CH$_2$NH$_2$, CH$_2$SO$_2$CH$_3$, -aryl, -arylalkyl, -heteroaryl, -heteroarylalkyl, -heterocycloalkyl, C$_3$-C$_{12}$-cycloalkyl, -polyalkoxyalkyl, -polyalkoxy, -methoxymethoxy, -methoxyethoxy, SH, S—C$_1$-C$_{12}$-alkyl, S—C$_2$-C$_{12}$-alkenyl, S—C$_2$-C$_{12}$-alkenyl, S—C$_3$-C$_{12}$-cycloalkyl, S-aryl, S-heteroaryl, and S-heterocycloalkyl;

R$_3$ is hydrogen or R$_3$ is alkyl, alkenyl, aryl, arylalkyl, heteroaryl, heterocycloalkyl, or cycloalkyl, each of which may be optionally substituted by replacement of one, two, or three or more of the hydrogen atoms with the substituent of R$_2$;

R$_5$ is hydrogen, or R$_5$ is alkyl, alkenyl, aryl aralkyl, heteroaryl, heterocycloalkyl, cycloalkyl or carbocyclic, each of which may be optionally substituted by replacement of one, two, or three or more of the hydrogen atoms with the substituent of R$_2$; and R$_6$ is hydrogen or optionally substituted alkyl by replacement of one, two, or three or more of the hydrogen atoms with the substituent of R$_2$.

2. A pharmaceutical composition comprising the compound of claim 1, or the pharmaceutically acceptable salt thereof, and a pharmaceutically acceptable carrier.

3. A kit comprising the compound of claim 1 or the pharmaceutically acceptable salt thereof, and instructions for use in treating cancer.

4. The compound of claim 1, wherein R$_5$ is optionally substituted phenyl or optionally substituted cyclopentyl by replacement of one, two, or three or more of the hydrogen atoms with the substituent of R$_2$, and R$_1$ is optionally substituted phenyl, wherein R$_1$ is substituted with 0-4 substituents, selected from the group consisting of alkoxy, hydroxy,

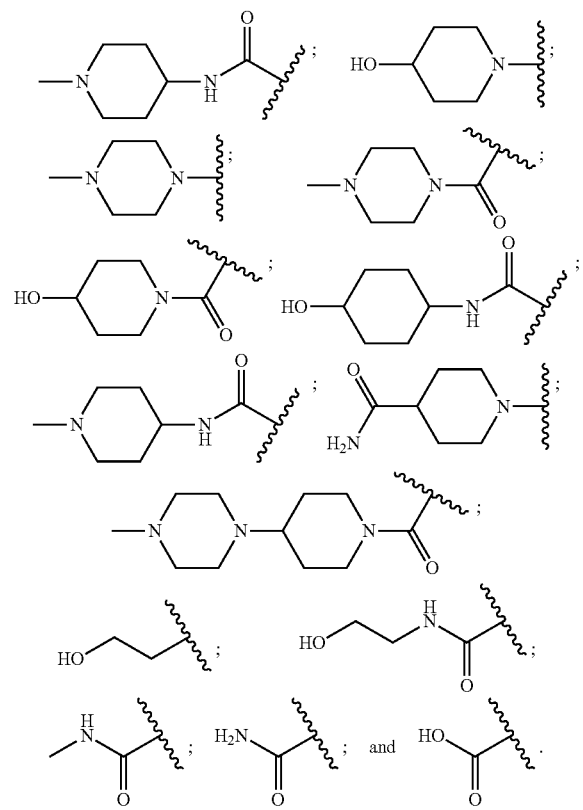

5. The pharmaceutical composition of claim 2, further comprising at least one additional therapeutic agent selected from the group consisting of Aricept18, Rivastigmine, L-DOPA/carbidopa, entacapone, ropinrole, pramipexole, bromocriptine, pergolide, trihexephendyl, amantadine, beta interferon, glatiramer acetate, mitoxantrone, albuterol, Montelukast sodium, zyprexa, risperdal, seroquel, haloperidol, corticosteroids, azathioprine, cyclophosphamide, sulfasalazine, cyclosporin, tacrolimus, rapamycin, mycophenolate mofetil, interferons, corticosteroids, cyclophophamide, azathioprine, sulfasalazine, interferons, riluzole, beta-blockers, ACE inhibitors, diuretics, nitrates, and statins, cholestyramine, gamma globulin, cyclosporine, cyclosporin G, FK-506, rapamycin, cyclophosphamide, azathioprine, methotrexate, brequinar, leflunomide, mizoribine, mycophenolic acid, mycophenolate mofetil, and 15-deoxyspergualin.

6. A compound selected from the group consisting of:
2-(2-methoxy-4-(4-methylpiperazin-1-yl)phenylamino)-5-methyl -9-phenyl-5H-pyrimido[5,4-e][1,4]diazepin-6(7H)-one;
3-methoxy-4-(5-methyl-6-oxo-9-phenyl-6,7-dihydro-5H-pyrimido[5,4-e][1,4]diazepin-2-ylamino)-N-(1-methylpiperidin-4-yl)benzamide;
4-(9-cyclopentyl-7-ethyl-5-methyl-6-oxo-6,7-dihydro-5H-pyrimido[5,4-e][1,4]diazepin-2-ylamino)-3-hydroxy-N-(1-methylpiperidin-4-yl)benzamide;
4-(7-ethyl-5-methyl-6-oxo-9-phenyl-6,7-dihydro-5H-pyrimido[5,4-e][1,4]diazepin-2-ylamino)-3-methoxy-N-(1-methylpiperidin-4-yl)benzamide; and
4-(9-cyclopentyl-5-methyl-6-oxo-6,7-dihydro-5H-pyrimido[5,4-e][1,4]diazepin-2-ylamino)-3-methoxy-N-(1-methylpiperidin-4-yl)benzamide, or a pharmaceutically acceptable salt thereof.

* * * * *